US011124502B2

(12) United States Patent
Fleury et al.

(10) Patent No.: US 11,124,502 B2
(45) Date of Patent: *Sep. 21, 2021

(54) NEPRILYSIN INHIBITORS

(71) Applicant: THERAVANCE BIOPHARMA R&D IP, LLC, South San Francisco, CA (US)

(72) Inventors: Melissa Fleury, Brisbane, CA (US); Adam D. Hughes, Half Moon Bay, CA (US)

(73) Assignee: THERAVANCE BIOPHARMA R&D IP, LLC, South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/739,525

(22) Filed: Jan. 10, 2020

(65) Prior Publication Data

US 2020/0283422 A1 Sep. 10, 2020

Related U.S. Application Data

(63) Continuation of application No. 16/209,112, filed on Dec. 4, 2018, now Pat. No. 10,570,120, which is a continuation of application No. 15/841,749, filed on Dec. 14, 2017, now Pat. No. 10,189,823, which is a continuation of application No. 15/497,508, filed on Apr. 26, 2017, now Pat. No. 9,873,685, which is a continuation of application No. 14/812,095, filed on Jul. 29, 2015, now Pat. No. 9,670,186, which is a continuation of application No. 13/961,269, filed on Aug. 7, 2013, now Pat. No. 9,126,956.

(60) Provisional application No. 61/774,163, filed on Mar. 7, 2013, provisional application No. 61/680,804, filed on Aug. 8, 2012.

(51) Int. Cl.

| C07D 405/12 | (2006.01) |
|---|---|
| A61K 31/415 | (2006.01) |
| A61K 31/4192 | (2006.01) |
| A61K 31/42 | (2006.01) |
| A61K 31/421 | (2006.01) |
| A61K 45/06 | (2006.01) |
| C07D 231/14 | (2006.01) |
| C07D 231/20 | (2006.01) |
| C07D 261/18 | (2006.01) |
| C07D 263/38 | (2006.01) |
| C07D 249/04 | (2006.01) |

(52) U.S. Cl.
CPC .......... *C07D 405/12* (2013.01); *A61K 31/415* (2013.01); *A61K 31/4192* (2013.01); *A61K 31/42* (2013.01); *A61K 31/421* (2013.01); *A61K 45/06* (2013.01); *C07D 231/14* (2013.01); *C07D 231/20* (2013.01); *C07D 249/04* (2013.01); *C07D 261/18* (2013.01); *C07D 263/38* (2013.01)

(58) Field of Classification Search
CPC .................................................. C07D 261/18
See application file for complete search history.

(56) References Cited

U.S. PATENT DOCUMENTS

| 4,189,604 A | 2/1980 | Umezawa et al. |
|---|---|---|
| 4,206,232 A | 6/1980 | Ondetti et al. |
| 4,374,829 A | 2/1983 | Harris et al. |
| 4,513,009 A | 4/1985 | Rogues et al. |
| 4,722,810 A | 2/1988 | Delaney et al. |
| 4,906,615 A | 3/1990 | Berger et al. |
| 4,929,641 A | 5/1990 | Haslanger et al. |
| 4,939,261 A | 7/1990 | Ksander |
| 4,975,444 A | 12/1990 | Danilewicz et al. |
| 5,021,430 A | 6/1991 | Ksander |
| 5,030,654 A | 7/1991 | Barnish et al. |
| 5,155,100 A | 10/1992 | Erion et al. |
| 5,208,255 A | 5/1993 | Duhamel et al. |
| 5,217,996 A | 6/1993 | Ksander |
| 5,294,632 A | 3/1994 | Erion et al. |
| 5,508,272 A | 4/1996 | Robl |

(Continued)

FOREIGN PATENT DOCUMENTS

WO 2011/088797 A1 7/2011

OTHER PUBLICATIONS

Ksander et al., "Dicarboxylic acid dipeptide neutral endopeptidase inhibitors", Journal of Medicinal Chemistry, 38(10): 1689-1700 (1995).

(Continued)

*Primary Examiner* — Kamal A Saeed
(74) *Attorney, Agent, or Firm* — Jeffrey A. Hagenah; Timothy R. Welch

(57) ABSTRACT

In one aspect, the invention relates to compounds having the formula:

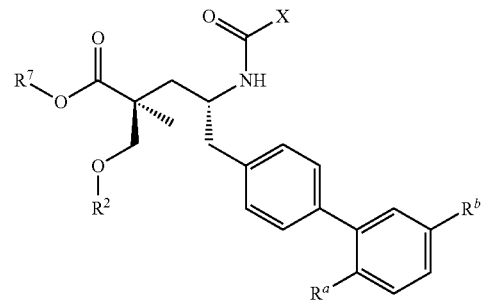

where X, $R^a$, $R^b$, $R^2$, and $R^7$ are as defined in the specification, or a pharmaceutically acceptable salt thereof. These compounds are prodrugs of compounds having neprilysin inhibition activity. In another aspect, the invention relates to pharmaceutical compositions comprising these compounds; methods of using these compounds; and processes and intermediates for preparing these compounds.

20 Claims, No Drawings

(56) References Cited

U.S. PATENT DOCUMENTS

| | | |
|---|---|---|
| 5,599,951 A | 2/1997 | Plaquevent et al. |
| 5,677,297 A | 10/1997 | Waldeck et al. |
| 5,977,075 A | 11/1999 | Ksander et al. |
| 6,602,866 B2 | 8/2003 | Flynn et al. |
| 6,660,756 B2 | 9/2003 | Challenger et al. |
| 8,449,890 B2 | 5/2013 | Fleury et al. |
| 8,481,044 B2 | 7/2013 | Fleury et al. |
| 8,513,244 B2 | 8/2013 | Gendron et al. |
| 8,563,512 B2 | 10/2013 | Smith et al. |
| 8,586,536 B2 | 11/2013 | Gendron et al. |
| 8,686,184 B2 | 4/2014 | Fleury et al. |
| 8,691,868 B2 | 4/2014 | Hughes et al. |
| 8,871,792 B2 | 10/2014 | Hughes et al. |
| 9,045,443 B2 | 6/2015 | Mammen et al. |
| 9,108,934 B2 | 8/2015 | Hughes et al. |
| 9,126,956 B2 | 9/2015 | Fleury et al. |
| 9,670,186 B2 | 6/2017 | Fleury et al. |
| 9,873,685 B2 | 1/2018 | Fleury et al. |
| 10,189,823 B2 | 1/2019 | Fleury et al. |
| 10,570,120 B2 | 2/2020 | Fleury et al. |
| 2010/0113801 A1 | 5/2010 | Hook et al. |
| 2010/0305131 A1 | 12/2010 | Coppola et al. |
| 2010/0305145 A1 | 12/2010 | Coppola et al. |
| 2011/0046397 A1 | 2/2011 | Hook et al. |
| 2011/0124695 A1 | 5/2011 | Iwaki et al. |
| 2012/0122844 A1 | 5/2012 | Foo |
| 2012/0122977 A1 | 5/2012 | Coppola et al. |
| 2012/0309724 A1 | 12/2012 | Fleury et al. |

OTHER PUBLICATIONS

Misawa et al., "Structure-based design of dipeptide derivatives for the human neutral endopeptidase", BioOrganic & Medicinal Chemistry, 19: 5935-5947 (2011).

PCT International Search Report for PCT/US2013/053956 dated Sep. 25, 2013.

NEPRILYSIN INHIBITORS

CROSS-REFERENCE TO RELATED APPLICATIONS

This application is a continuation of U.S. application Ser. No. 16/209,112, filed on Dec. 4, 2018, now U.S. Pat. No. 10,570,120; which is a continuation of U.S. application Ser. No. 15/841,749, filed on Dec. 14, 2017, now U.S. Pat. No. 10,189,823; which is a continuation of U.S. application Ser. No. 15/497,508, filed on Apr. 26, 2017, now U.S. Pat. No. 9,873,685; which is a continuation of U.S. application Ser. No. 14/812,095, filed on Jul. 29, 2015, now U.S. Pat. No. 9,670,186; which is a continuation of U.S. application Ser. No. 13/961,269, filed on Aug. 7, 2013, now U.S. Pat. No. 9,126,956; which claims the benefit of U.S. Provisional Application No. 61/680,804, filed on Aug. 8, 2012 and U.S. Provisional Application No. 61/774,163, filed on Mar. 7, 2013; the entire disclosures of which are incorporated herein by reference.

BACKGROUND OF THE INVENTION

Field of the Invention

The present invention relates to novel compounds having neprilysin-inhibition activity or which are metabolized in vivo to compounds having such activity. The invention also relates to pharmaceutical compositions comprising these compounds, processes and intermediates for preparing these compounds and methods of using these compounds to treat diseases such as hypertension, heart failure, pulmonary hypertension, and renal disease.

State of the Art

Commonly-assigned U.S. Patent Publication No. 2012/0213806, filed on Feb. 16, 2012 to Fleury et al., describes novel compounds that have activity as neprilysin inhibitors, the disclosure of which is incorporated herein by reference. In particular, compounds of the genus:

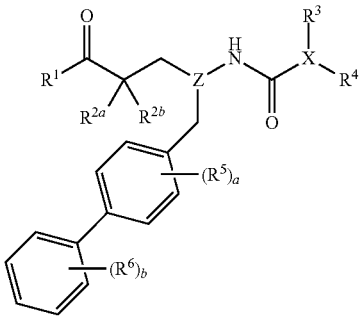

are described. Depending upon the variables, compounds within this genus can be referred to as being in the active form or as being a prodrug, which is metabolized in vivo to generate the active form of the compound.

In spite of these compounds however, there remains a need for compounds and prodrugs within this genus that have different metabolic and cleavage properties. For example, there remains a need for active compounds and/or prodrug compounds having improved oral absorption and for prodrug compounds that undergo rapid cleavage to form the active compound. This invention is directed to that need.

SUMMARY OF THE INVENTION

One aspect of the invention relates to a compound of formula I:

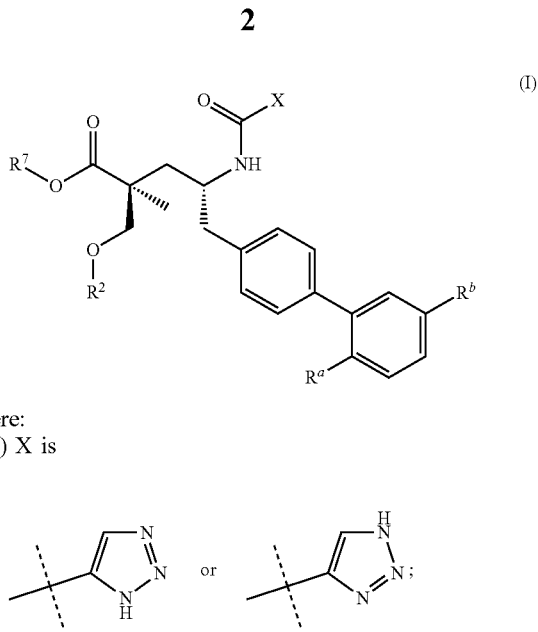

where:
(i) X is

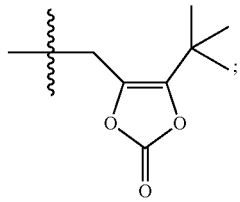 [SMILES: *Cc1oc(=O)oc1C(C)(C)C]

and
(a) $R^a$ and $R^b$ are H; $R^2$ is H; and $R^7$ is selected from $-CH_2CF_2CH_3$, $-CH_2CF_2CF_3$, $-(CH_2)_5CH_3$, $-(CH_2)_6CH_3$, and

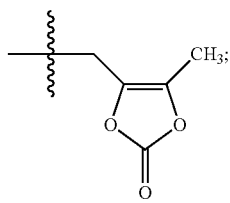 [SMILES: *Cc1oc(=O)oc1C]

or $R^2$ is $-C_{1-6}$alkyl or $-C(O)-C_{1-6}$alkyl, and $R^7$ is H; or
(b) $R^a$ is selected from $-CH_3$, $-OCH_3$, and Cl and $R^b$ is H; or $R^a$ is selected from H, $-CH_3$, Cl, and F, and $R^b$ is Cl; or $R^a$ is H and $R^b$ is selected from $-CH_3$ and $-CN$; $R^2$ is selected from H, $-C_{1-6}$alkyl, $-(CH_2)_{2-3}OR^e$, and $-(CH_2)_{2-3}NR^eR^e$; and $R^7$ is selected from H, $-C_{1-6}$alkyl, $-[(CH_2)_2O]_{1-3}CH_3$, $-CHR^cOC(O)-C_{1-4}$alkyl, $-CH_2OC(O)CHR^d-NH_2$, $-CH_2OC(O)CHR^d-NHC(O)O-C_{1-6}$alkyl, $-CHR^cOC(O)O-C_{2-4}$alkyl, $-CHR^cOC(O)O-$cyclohexyl, $-CH_2CH(NH_2)C(O)OCH_3$, $-C_{2-4}$alkylene-$N(CH_3)_2$, $-C_{0-6}$alkylenemorpholinyl, and (c) $R^a$ is H and $R^b$ is F; or $R^a$ is F and $R^b$ is H; $R^2$ is selected from H, $-C_{1-6}$alkyl, $-(CH_2)_{2-3}OR^e$, and $-(CH_2)_{2-3}NR^eR^e$; and $R^7$ is selected from $-C_{1-6}$alkyl, $-[(CH_2)_2O]_{1-3}CH_3$, $-CHR^cOC(O)-C_{1-4}$alkyl, $-CH_2OC(O)CHR^d-NH_2$, $-CH_2OC(O)CHR^d-NHC(O)O-C_{1-6}$alkyl, $-CHR^cOC(O)O-C_{2-4}$alkyl, $-CHR^cOC(O)O$-cyclohexyl, $-CH_2CH(NH_2)C(O)OCH_3$, $-C_{2-4}$alkylene-$N(CH_3)_2$, $-C_{0-6}$alkylenemorpholinyl, and

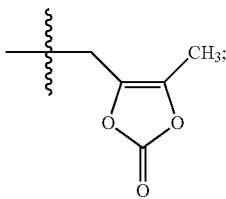 [SMILES: *Cc1oc(=O)oc1C]

or (ii) X is

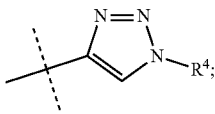

and (a) $R^a$ is Cl and $R^b$ is H; or $R^a$ is H and $R^b$ is selected from Cl, F, —CH$_3$, and —CN; or $R^a$ is F and $R^b$ is Cl; $R^2$ is selected from H, —C$_{1-6}$alkyl, —(CH$_2$)$_{2-3}$OR$^e$, and —(CH$_2$)$_{2-3}$NR$^e$R$^e$; $R^4$ is selected from —OH, —OCH$_3$, —OCH$_2$CH$_3$, and —C$_{1-4}$alkyl; and $R^7$ is selected from H, —C$_{1-6}$alkyl, —[(CH$_2$)$_2$O]$_{1-3}$CH$_3$, —CHR$^c$OC(O)—C$_{1-4}$alkyl, —CH$_2$OC(O)CHR$^d$—NH$_2$, —CH$_2$OC(O)CHR$^d$—NHC(O)O—C$_{1-6}$alkyl, —CHR$^c$OC(O)O—C$_{2-4}$alkyl, —CHR$^c$OC(O)O— cyclohexyl, —CH$_2$CH(NH$_2$)C(O)OCH$_3$, —C$_{2-4}$alkylene-N(CH$_3$)$_2$, —C$_{0-6}$alkylenemorpholinyl, and

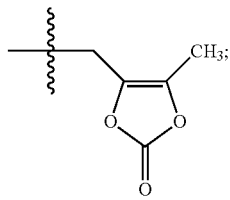 [SMILES: *Cc1oc(=O)oc1C]

or (b) $R^a$ is F and $R^b$ is H; $R^2$ is H; $R^4$ is —OH; and $R^7$ is selected from —C$_{1-6}$alkyl, —[(CH$_2$)$_2$O]$_{1-3}$CH$_3$, —CHR$^c$OC(O)—C$_{1-4}$alkyl, —CH$_2$OC(O)CHR$^d$—NH$_2$, —CH$_2$OC(O)CHR$^d$—NHC(O)O—C$_{1-6}$alkyl, —CHR$^c$OC(O)O—C$_{2-4}$alkyl, —CHR$^c$OC(O)O—cyclohexyl, —CH$_2$CH(NH$_2$)C(O)OCH$_3$, —C$_{2-4}$alkylene-N(CH$_3$)$_2$, —C$_{0-6}$alkylenemorpholinyl, and

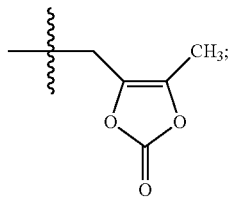 [SMILES: *Cc1oc(=O)oc1C]

or (iii) X is

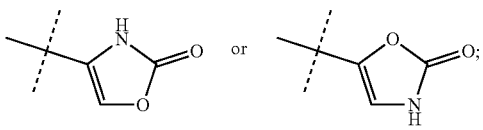

and (a) $R^a$ is Cl and $R^b$ is H; or $R^a$ is H and $R^b$ is selected from Cl, F, —CH$_3$, and —CN; or $R^a$ is F and $R^b$ is Cl; $R^2$ is selected from H, —C$_{1-6}$alkyl, —(CH$_2$)$_{2-3}$OR$^e$, and —(CH$_2$)$_{2-3}$NR$^e$R$^e$; and $R^7$ is selected from H, —C$_{1-6}$alkyl, —[(CH$_2$)$_2$O]$_{1-3}$CH$_3$, —CHR$^c$OC(O)—C$_{1-4}$alkyl, —CH$_2$OC(O)CHR$^d$—NH$_2$, —CH$_2$OC(O)CHR$^d$—NHC(O)O—C$_{1-6}$alkyl, —CHR$^c$OC(O)O—C$_{2-4}$alkyl, —CHR$^c$OC(O)O-cyclohexyl, —CH$_2$CH(NH$_2$)C(O)OCH$_3$, —C$_{2-4}$alkylene-N(CH$_3$)$_2$, —C$_{0-6}$alkylenemorpholinyl, and

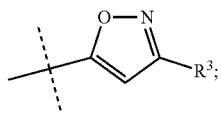

or (iv) X is R

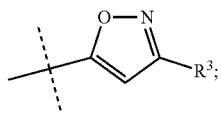

(a) $R^a$ and $R^b$ are H; $R^2$ is selected from —C$_{1-6}$alkyl, —(CH$_2$)$_{2-3}$OR$^e$, and —(CH$_2$)$_{2-3}$NR$^e$R$^e$; $R^3$ is selected from —OH, —OCH$_3$, —OCH$_2$CH$_3$, and —C$_{1-4}$alkyl; and $R^7$ is H; or (b) $R^a$ is selected from Cl and F and $R^b$ is H; or $R^a$ is H and $R^b$ is selected from Cl, F, —CH$_3$, and —CN; or $R^a$ is F and $R^b$ is Cl; $R^2$ is selected from H, —C$_{1-6}$alkyl, —(CH$_2$)$_{2-3}$OR$^e$, and —(CH$_2$)$_{2-3}$NR$^e$R$^e$; $R^3$ is selected from —OH, —OCH$_3$, —OCH$_2$CH$_3$, and —C$_{1-4}$alkyl; and $R^7$ is selected from H, —C$_{1-6}$alkyl, —[(CH$_2$)$_2$O]$_{1-3}$CH$_3$, —CHR$^c$OC(O)—C$_{1-4}$alkyl, —CH$_2$OC(O)CHR$^d$—NH$_2$, —CH$_2$OC(O)CHR$^d$—NHC(O)O—C$_{1-6}$alkyl, —CHR$^c$OC(O)O—C$_{2-4}$alkyl, —CHR$^c$OC(O)O-cyclohexyl, —CH$_2$CH(NH$_2$)C(O)OCH$_3$, —C$_{2-4}$alkylene-N(CH$_3$)$_2$, —C$_{0-6}$alkylenemorpholinyl, and

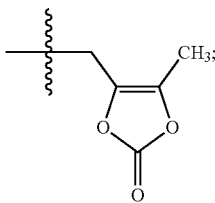 [SMILES: *Cc1oc(=O)oc1C]

or (v) X is

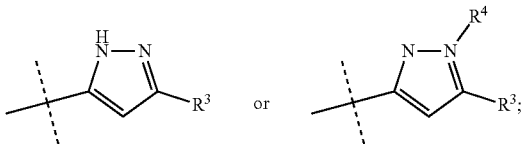

$R^a$ is selected from Cl and F and $R^b$ is H; or $R^a$ is H and $R^b$ is selected from Cl, F, —CH$_3$, and —CN; or $R^a$ is F and $R^b$ is Cl; $R^2$ is selected from H, —C$_{1-6}$alkyl, —(CH$_2$)$_{2-3}$OR$^e$, and —(CH$_2$)$_{2-3}$NR$^e$R$^e$; $R^3$ is selected from —OH, —OCH$_3$, —OCH$_2$CH$_3$, and —C$_{1-4}$alkyl; $R^4$ is selected from H, —C$_{1-6}$alkyl, and phenyl; and $R^7$ is selected from H, —C$_{1-6}$alkyl, —[(CH$_2$)$_2$O]$_{1-3}$CH$_3$, —CHR$^c$OC(O)—C$_{1-4}$alkyl, —CH$_2$OC(O)CHR$^d$—NH$_2$, —CH$_2$OC(O)CHR$^d$—NHC(O)O—C$_{1-6}$alkyl, —CHR$^c$OC(O)O—C$_{2-4}$alkyl, —CHR$^c$OC(O)O-cyclohexyl, —CH$_2$CH(NH$_2$)C(O)OCH$_3$, —C$_{2-4}$alkylene-N(CH$_3$)$_2$, —C$_{0-6}$alkylenemorpholinyl, and

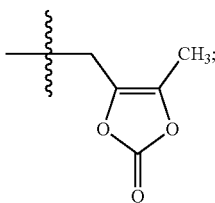 [SMILES: *Cc1oc(=O)oc1C]

or (vi) X is

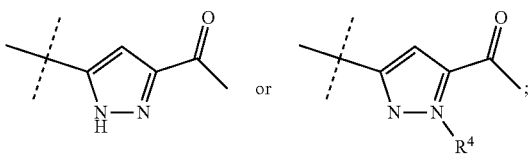

$R^a$ is selected from Cl and F and $R^b$ is H; or $R^a$ is H and $R^b$ is selected from Cl, F, —CH$_3$, and —CN; or $R^a$ is F and $R^b$ is Cl; $R^2$ is selected from H, —C$_{1-6}$alkyl, —(CH$_2$)$_{2-3}$OR$^e$, and —(CH$_2$)$_{2-3}$NR$^e$R$^e$; $R^4$ is selected from H, —C$_{1-6}$alkyl, and phenyl; and $R^7$ is selected from H, —C$_{1-6}$alkyl, —[(CH$_2$)$_2$O]$_{1-3}$CH$_3$, —CHR$^c$OC(O)—C$_{1-4}$alkyl, —CH$_2$OC(O)CHR$^d$—NH$_2$, —CH$_2$OC(O)CHR$^d$—NHC(O)O—C$_{1-6}$alkyl, —CHR$^c$OC(O)O—C$_{2-4}$alkyl, —CHR$^c$OC(O)O—cyclohexyl, —CH$_2$CH(NH$_2$)C(O)OCH$_3$, —C$_{2-4}$alkylene-N(CH$_3$)$_2$, —C$_{0-6}$alkylenemorpholinyl, and

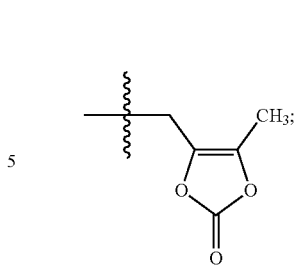

or (vii) X is

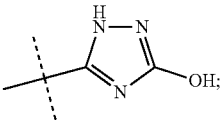

$R^a$ is selected from Cl and F and $R^b$ is H; or $R^a$ is H and $R^b$ is selected from Cl, F, —CH$_3$, and —CN; or $R^a$ is F and $R^b$ is Cl; $R^2$ is selected from H, —C$_{1-6}$alkyl, —(CH$_2$)$_{2-3}$OR$^e$, and —(CH$_2$)$_{2-3}$NR$^e$R$^e$; and $R^7$ is selected from H, —C$_{1-6}$alkyl, —[(CH$_2$)$_2$O]$_{1-3}$CH$_3$, —CHR$^c$OC(O)—C$_{1-4}$alkyl, —CH$_2$OC(O)CHR$^d$—NH$_2$, —CH$_2$OC(O)CHR$^d$—NHC(O)O—C$_{1-6}$alkyl, —CHR$^c$OC(O)O—C$_{2-4}$alkyl, —CHR$^c$OC(O)O-cyclohexyl, —CH$_2$CH(NH$_2$)C(O)OCH$_3$, —C$_{2-4}$alkylene-N(CH$_3$)$_2$, —C$_{0-6}$alkylenemorpholinyl, and

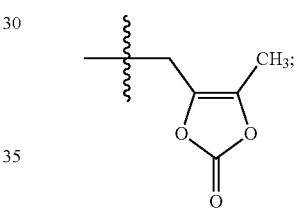

or (viii) X is

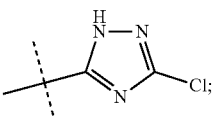

$R^a$ is selected from Cl and F and $R^b$ is H; or $R^a$ is H and $R^b$ is selected from Cl, F, —CH$_3$, and —CN; or $R^a$ is F and $R^b$ is Cl; $R^2$ is selected from H, —C$_{1-6}$alkyl, —(CH$_2$)$_{2-3}$OR$^e$, and —(CH$_2$)$_{2-3}$NR$^e$R$^e$; and $R^7$ is selected from H, —C$_{1-6}$alkyl, —[(CH$_2$)$_2$O]$_{1-3}$CH$_3$, —CHR$^c$OC(O)—C$_{1-4}$alkyl, —CH$_2$OC(O)CHR$^d$—NH$_2$, —CH$_2$OC(O)CHR$^d$—NHC(O)O—C$_{1-6}$alkyl, —CHR$^c$OC(O)O—C$_{2-4}$alkyl, —CHR$^c$OC(O)O-cyclohexyl, —CH$_2$CH(NH$_2$)C(O)OCH$_3$, —C$_{2-4}$alkylene-N(CH$_3$)$_2$, —C$_{0-6}$alkylenemorpholinyl, and

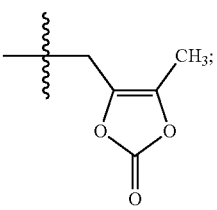

where each $R^c$ is independently H or —C$_{1-3}$alkyl; each $R^d$ is independently H, —CH$_3$, —CH(CH$_3$)$_2$, phenyl, or benzyl;

and each $R^e$ is independently H or —$CH_3$; or a pharmaceutically acceptable salt thereof.

The present invention provides compounds which are metabolized in vivo to compounds that have been found to possess neprilysin (NEP) enzyme inhibition activity. Accordingly, compounds of the invention are expected to be useful and advantageous as therapeutic agents for treating patients suffering from a disease or disorder that is treated by inhibiting the NEP enzyme or by increasing the levels of its peptide substrates. Thus, one aspect of the invention relates to a method of treating hypertension, heart failure, or renal disease, comprising administering to a patient a therapeutically effective amount of a compound of the invention.

Another aspect of the invention relates to pharmaceutical compositions comprising a pharmaceutically acceptable carrier and a compound of the invention.

Yet another aspect of the invention relates to processes and intermediates useful for preparing compounds of the invention. Another aspect of the invention relates to a process of preparing a pharmaceutically acceptable salt of a compound of formula I, comprising contacting a compound of formula I in free acid or base form with a pharmaceutically acceptable base or acid. In other aspects, the invention relates to products prepared by any of the processes described herein, as well as novel intermediates used in such process.

Yet another aspect of the invention relates to the use of a compound of formula I or a pharmaceutically acceptable salt thereof, for the manufacture of a medicament, especially for the manufacture of a medicament useful for treating hypertension, heart failure, or renal disease. Another aspect of the invention relates to use of a compound of the invention for inhibiting a NEP enzyme in a mammal. Still another aspect of the invention relates to the use of a compound of the invention as a research tool. Other aspects and embodiments of the invention are disclosed herein.

DETAILED DESCRIPTION OF THE INVENTION

When describing the compounds, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group which may be linear or branched. Unless otherwise defined, such alkyl groups typically contain from 1 to 10 carbon atoms and include, for example, —$C_{1-6}$alkyl, meaning an alkyl group having from 1 to 6 carbon atoms where the carbon atoms are in any acceptable configuration. Representative alkyl groups include, by way of example, methyl, ethyl, n-propyl, isopropyl, n-butyl, s-butyl, isobutyl, t-butyl, n-pentyl, n-hexyl, and the like.

As used herein, the phrase "of the formula" or "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

As used herein, the term "prodrug" is intended to mean an inactive (or significantly less active) precursor of a drug that is converted into its active form in the body under physiological conditions, for example, by normal metabolic processes. Such compounds may not necessarily possess pharmacological activity at NEP, but may be administered orally or parenterally and thereafter metabolized in the body to form a compound that is pharmacologically active at NEP.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate, or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising a NEP enzyme, an "effective amount" may be the amount needed to inhibit the enzyme.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, i.e., preventing the reoccurrence of the disease or medical condition or prophylactic treatment of a patient that is pre-disposed to the disease or medical condition; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition, as well as test subjects in which the crystalline compound is being evaluated or being used in an assay, for example an animal model.

All other terms used herein are intended to have their ordinary meaning as understood by those of ordinary skill in the art to which they pertain.

The compounds of the invention contain one or more chiral centers and therefore, these compounds may be prepared and used in various stereoisomeric forms. In some embodiments, in order to optimize the therapeutic activity of the compounds of the invention, e.g., to treat hypertension, it may be desirable that the carbon atoms have a particular (R,R), (S,S), (S,R), or (R,S) configuration or are enriched in a stereoisomeric form having such configuration. In other embodiments, the compounds of the invention are present as racemic mixtures. Accordingly, the invention also relates to racemic mixtures, pure stereoisomers (e.g., enantiomers and diastereoisomers), stereoisomer-enriched mixtures, and the like unless otherwise indicated. When a chemical structure is depicted herein without any stereochemistry, it is understood that all possible stereoisomers are encompassed by such structure. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual stereoisomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds of the invention are included within the scope of the invention unless otherwise specified. For example, although a formula is depicted as:

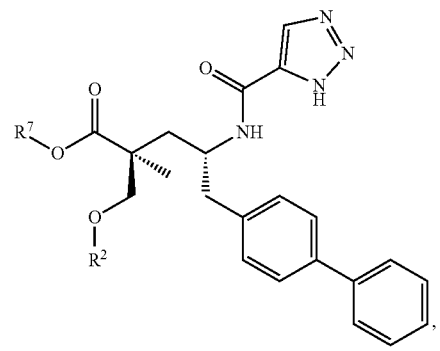

it is understood that the compound may also exist in a tautomeric form such as:

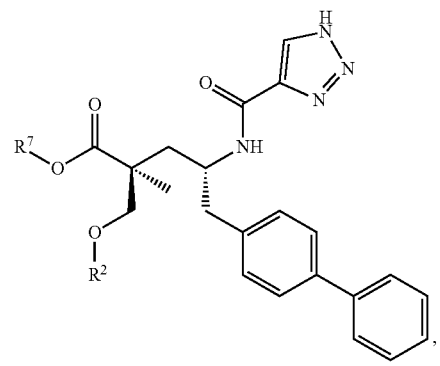

and that both forms are covered by the invention. It is also understood that one tautomer may be predominant.

The compounds of the invention, as well as those compounds used in their synthesis, may also include isotopically-labeled compounds, that is, where one or more atoms have been enriched with atoms having an atomic mass different from the atomic mass predominately found in nature. Examples of isotopes that may be incorporated into the compounds of formula I, for example, include, but are not limited to, $^2$H, $^3$H, $^{13}$C, $^{14}$C, 15 $^{15}$N, $^{18}$O, $^{17}$O, $^{35}$S, $^{36}$Cl, and $^{18}$F. Of particular interest are compounds of formula I enriched in tritium or carbon-14 which can be used, for example, in tissue distribution studies; compounds of the invention enriched in deuterium especially at a site of metabolism resulting, for example, in compounds having greater metabolic stability; and compounds of formula I enriched in a positron emitting isotope, such as $^{11}$C, $^{18}$F, $^{15}$O and $^{13}$N, which can be used, for example, in Positron Emission Topography (PET) studies.

The nomenclature used herein to name the compounds of the invention is illustrated in the Examples herein. This nomenclature has been derived using the commercially available AutoNom software (MDL, San Leandro, Calif.).

U.S. Patent Publication No. 2012/0213806 specifically discloses (2S,4R)-5-biphenyl-4-yl-2-hydroxymethyl-2-methyl-4-[(3H-[1,2,3]triazole-4-carbonyl)amino]-pentanoic acid, which is represented by formula I' (where R$^a$ and R$^b$ are H):

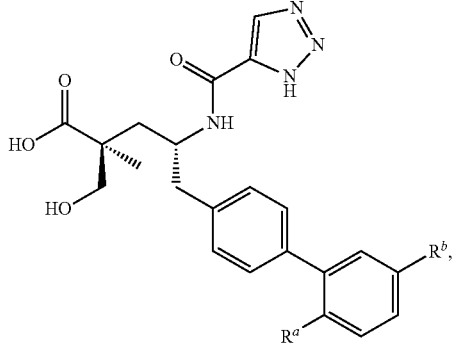

(I')

Compounds such as this can exist in a tautomer form, for example, as (2S,4R)-5-biphenyl-4-yl-2-hydroxymethyl-2-methyl-4-[(1H-[1,2,3]triazole-4-carbonyl)amino]pentanoic acid. In one embodiment, this compound is referred to as the active form and is administered as a prodrug, which is metabolized in vivo to form the compound of formula I'. U.S. Patent Publication No. 2012/0213806 also discloses certain prodrugs of the compound of formula I' such as the ethyl ester, propyl ester, isopropyl ester, butyl ester, isobutyl ester, 3-methylbutyl ester, pentyl ester, medoxomil ester, 2-morpholin-4-ylethyl ester, 2-morpholin-4-yl-2-oxo-ethyl ester, 2-methoxyethyl ester, 2-(2-methoxyethoxy)ethyl ester, 2-methanesulfonylethyl ester, 2-dimethylaminoethyl ester, 2-piperidin-1-ylethyl ester, indan-5-yl ester, oxetan-3-yl ester, dimethylcarbamoylmethyl ester, methoxycarbonylmethyl ester, acetoxymethyl ester, butyryloxymethyl ester, benzyloxycarbonylmethyl ester, 2-(2-oxopyrrolidin-1-yl) ethyl ester, ethoxycarbonyloxymethyl ester, benzyl ester, (S)-2-amino-3-methyl-butyryloxymethyl ester, (S)-2-methoxycarbonylamino-3-methyl-butyryloxymethyl ester, (R)-1-cyclohexyloxycarbonyloxyethyl ester, (S)-1-cyclohexyloxycarbonyloxyethyl ester; and 5-methyl-2-oxo-[1,3] dioxol-4-ylmethyl ester prodrugs.

One aspect of the invention relates to other prodrugs and variants of the compound of formula I'. These compounds are compounds of formula I, where X is:

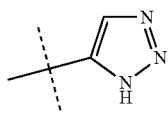 or 

These compounds are represented by formula IIa or IIb:

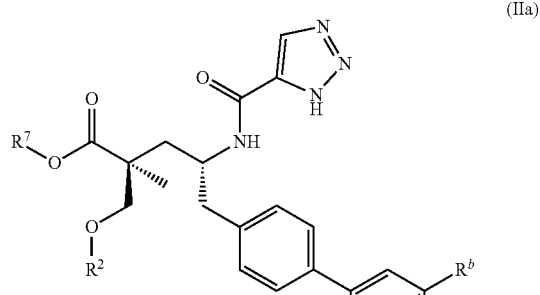

(IIa)

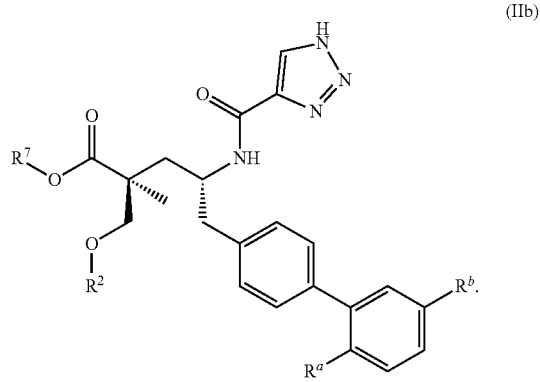

(IIb)

In one embodiment of the compounds of formula IIa and IIb, R$^a$ and R$^b$ are H; R$^2$ is H; and R$^7$ is selected from —CH$_2$CF$_2$CH$_3$, —CH$_2$CF$_2$CF$_3$, —(CH$_2$)$_5$CH$_3$, —(CH$_2$)$_6$CH$_3$, and

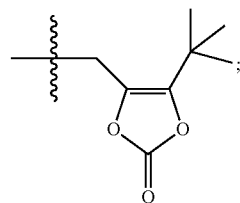 [SMILES: *Cc1oc(=O)oc1C(C)(C)C]

or R$^2$ is —C$_{1-6}$alkyl or —C(O)—C$_{1-6}$alkyl, and R$^7$ is H. In one specific embodiment, R$^2$ is H and R$^7$ is selected from —CH$_2$CF$_2$CH$_3$, —CH$_2$CF$_2$CF$_3$, —(CH$_2$)$_5$CH$_3$, —(CH$_2$)$_6$CH$_3$, and

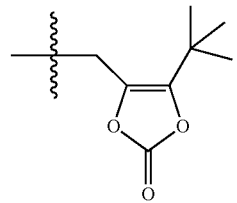 [SMILES: *Cc1oc(=O)oc1C(C)(C)C]

or
R$^2$ selected from —CH$_3$, —CH$_2$CH$_3$, —C(O)CH$_3$, —C(O)CH(CH$_3$)$_2$, and —C(O)CH$_2$CH(CH$_3$)$_2$; and R$^7$ is H.

In another embodiment of the compounds of formula IIa and IIb, R$^a$ is selected from —CH$_3$, —OCH$_3$, and Cl and R$^b$ is H; or R$^a$ is selected from H, —CH$_3$, Cl, and F, and R$^b$ is Cl; or R$^a$ is H and R$^b$ is selected from —CH$_3$ and —CN; R$^2$ is selected from H, —$C_{1-6}$alkyl, —$(CH_2)_{2-3}OR^e$, and —$(CH_2)_{2-3}NR^eR^e$; and $R^7$ is selected from H, —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$-cyclohexyl —$CH_2CH(NH_2)C(O)OCH_3$, —$C_{2-4}$alkylene-N$(CH_3)_2$, —$C_{0-6}$alkylenemorpholinyl, and

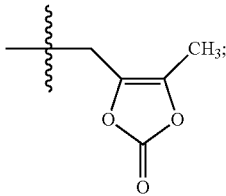

where each $R^c$ is independently H or —$C_{1-3}$alkyl; each $R^d$ is independently H, —$CH_3$, —$CH(CH_3)_2$, phenyl, or benzyl; and each $R^e$ is independently H or —$CH_3$. In one specific embodiment, $R^a$ is selected from —$CH_3$, —$OCH_3$, and Cl and $R^b$ is H; or $R^a$ is selected from H, —$CH_3$, Cl, and F, and $R^b$ is Cl; or $R^a$ is H and $R^b$ is selected from —$CH_3$ and —CN; $R^2$ is selected from H, —$C_{1-6}$alkyl (e.g., —$CH_3$, —$CH_2CH_3$, —$CH(CH_3)$, or —$(CH_2)_4CH_3$), and —$(CH_2)_{2-3}OR^e$ where $R^e$ is H (e.g., —$(CH_2)_2OH$ and —$(CH_2)_3OH$) or —$CH_3$ (e.g., —$(CH_2)_2OCH_3$); and $R^7$ is H.

U.S. Patent Publication No. 2012/0213806 also discloses compounds of formula I', where $R^a$ is H and $R^b$ is F, (2S,4R)-5-(3'-fluorobiphenyl-4-yl)-2-hydroxymethyl-2-methyl-4-[(3H-[1,2,3]triazole-4-carbonyl)amino]pentanoic acid, and where $R^a$ is F and $R^b$ is H, (2S,4R)-5-(2'-fluorobiphenyl-4-yl)-2-hydroxymethyl-2-methyl-4-[(3H-[1,2,3]triazole-4-carbonyl)amino]pentanoic acid. Thus, another aspect of the invention relates to prodrugs of such compounds. Therefore, in another embodiment of the compounds of formula IIa and IIb, $R^a$ is H and $R^b$ is F; or $R^a$ is F and $R^b$ is H; $R^2$ is selected from H, —$C_{1-6}$alkyl, —$(CH_2)_{2-3}OR^e$, and —$(CH_2)_{2-3}NR^eR^e$; and $R^7$ is selected from —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$-cyclohexyl, —$CH_2CH(NH_2)C(O)OCH_3$, —$C_{2-4}$alkylene-N$(CH_3)_2$, —$C_{0-6}$alkylenemorpholinyl, and

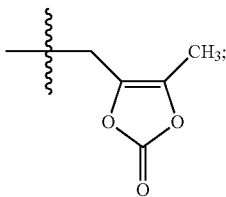

where each $R^c$ is independently H or —$C_{1-3}$alkyl; each $R^d$ is independently H, —$CH_3$, —$CH(CH_3)_2$, phenyl, or benzyl; and each $R^e$ is independently H or —$CH_3$.

Another aspect of the invention relates to compounds of formula I, where X is:

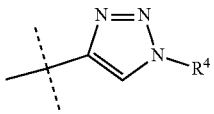

These compounds are represented by formula III:

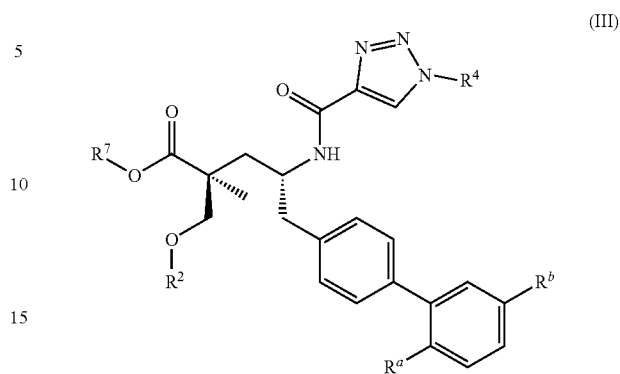

In one embodiment of the compounds of formula III, $R^a$ is Cl and $R^b$ is H; or $R^a$ is H and $R^b$ is selected from Cl, F, —$CH_3$, and —CN; or $R^a$ is F and $R^b$ is Cl; $R^2$ is selected from H, —$C_{1-6}$alkyl, —$(CH_2)_{2-3}OR^e$, and —$(CH_2)_{2-3}NR^eR^e$; $R^4$ is selected from —OH, —$OCH_3$, —$OCH_2CH_3$, and —$C_{1-4}$alkyl; and $R^7$ is selected from H, —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$-cyclohexyl, —$CH_2CH(NH_2)C(O)OCH_3$, —$C_{2-4}$alkylene-N$(CH_3)_2$, —$C_{0-6}$alkylenemorpholinyl, and

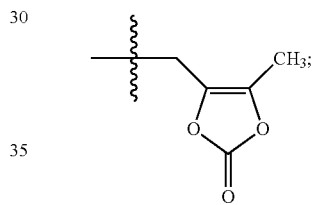

where each $R^c$ is independently H or —$C_{1-3}$alkyl; each $R^d$ is independently H, —$CH_3$, —$CH(CH_3)_2$, phenyl, or benzyl; and each $R^e$ is independently H or —$CH_3$. In one specific embodiment, $R^a$ is F, $R^b$ is Cl, $R^2$ is H, $R^4$ is —$OCH_3$ or —$OCH_2CH_3$, and $R^7$ is H.

U.S. Patent Publication No. 2012/0213806 discloses a compound of formula III, where $R^a$ is F, $R^b$ is H, $R^2$ is H, and $R^7$ is H, (2S,4R)-5-(2'-fluorobiphenyl-4-yl)-2-hydroxymethyl-4-[(1-hydroxy-1H-[1,2,3]triazole-4-carbonyl)amino]-2-methylpentanoic acid. Thus, another aspect of the invention relates to prodrugs of this compound. Therefore, in another embodiment of the compounds of formula III, $R^a$ is F and $R^b$ is H; $R^2$ is H; $R^4$ is —OH; and $R^7$ is selected from —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$-cyclohexyl, —$CH_2CH(NH_2)C(O)OCH_3$, —$C_{2-4}$alkylene-N$(CH_3)_2$, —$C_{0-6}$alkylenemorpholinyl, and

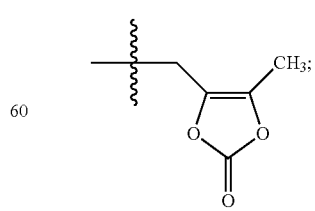

where each $R^c$ is independently H or —$C_{1-3}$alkyl; and each $R^d$ is independently H, —$CH_3$, —$CH(CH_3)_2$, phenyl, or benzyl.

Another aspect of the invention relates to compounds of formula I, where X is:

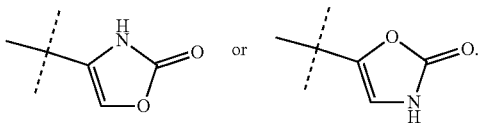

These compounds are represented by formula IVa or IVb:

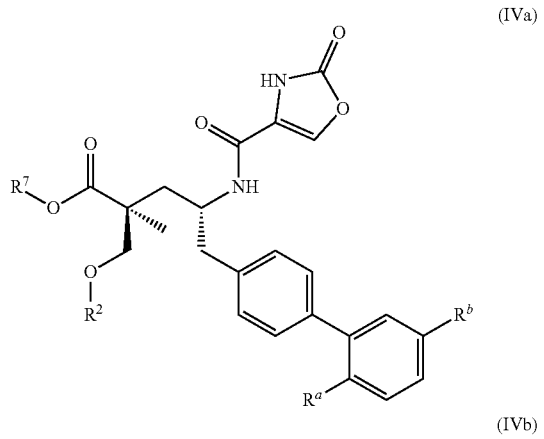
(IVa)

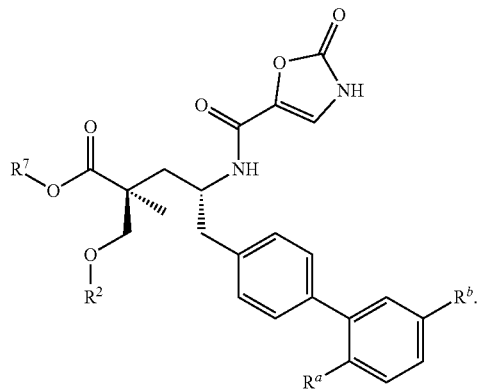
(IVb)

In one embodiment of the compounds of formula IVa and IVb, $R^a$ is Cl and $R^b$ is H; or $R^a$ is H and $R^b$ is selected from Cl, F, —$CH_3$, and —CN; or $R^a$ is F and $R^b$ is Cl; $R^2$ is selected from H, —$C_{1-6}$alkyl, —$(CH_2)_{2-3}OR^e$, and —$(CH_2)_{2-3}NR^eR^e$; and $R^7$ is selected from H, —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$—cyclohexyl, —$CH_2CH(NH_2)C(O)OCH_3$, —$C_{2-4}$alkylene-N($CH_3$)$_2$, —$C_{0-6}$alkylenemorpholinyl, and

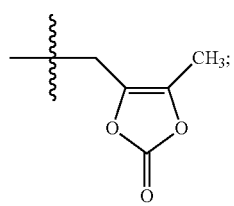

where each R is independently H or —$C_{1-3}$alkyl; each $R^d$ is independently H, —$CH_3$, —$CH(CH_3)_2$, phenyl, or benzyl; and each $R^e$ is independently H or —$CH_3$. In one specific embodiment, $R^a$ is F, $R^b$ is Cl, $R^2$ is H, and $R^7$ is H.

U.S. Patent Publication No. 2012/0213806 discloses a compound of formula IVa, where $R^a$ is F, $R^b$ is H, $R^2$ is H, and $R^7$ is H, (2S,4R)-5-(2'-fluorobiphenyl-4-yl)-2-hydroxymethyl-2-methyl-4-[(2-oxo-2,3-dihydrooxazole-4-carbonyl)amino]pentanoic acid, and a compound of formula IVb, where $R^a$ is F, $R^b$ is H, $R^2$ is H, and $R^7$ is H, (2S,4R)-5-(2'-fluorobiphenyl-4-yl)-2-hydroxymethyl-2-methyl-4-[(2-oxo-2,3-dihydrooxazole-5-carbonyl)amino]pentanoic acid. Thus, another aspect of the invention relates to prodrugs of these compounds. Therefore, in another embodiment of the compounds of formula IVa and IVb, $R^a$ is F and $R^b$ is H; $R^2$ is H; and $R^7$ is selected from —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$-cyclohexyl, —$CH_2CH(NH_2)C(O)OCH_3$, —$C_{2-4}$alkylene-N($CH_3$)$_2$, —$C_{0-6}$alkylenemorpholinyl, and

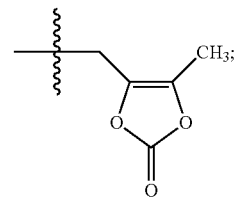

where each $R^c$ is independently H or —$C_{1-3}$alkyl; and each $R^d$ is independently H, —$CH_3$, —$CH(CH_3)_2$, phenyl, or benzyl.

U.S. Patent Publication No. 2012/0213806 specifically discloses (2S,4R)-5-biphenyl-4-yl-4-[(3-hydroxyisoxazole-5-carbonyl)amino]-2-hydroxymethyl-2-methylpentanoic acid, which is represented by formula V' (where $R^a$ and $R^b$ are H and $R^3$ is —OH):

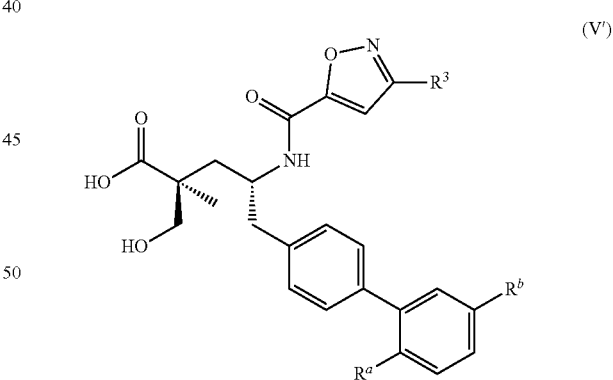
(V')

U.S. Patent Publication No. 2012/0213806 also discloses certain prodrugs of the compound of formula V' such as the ethyl ester. One aspect of the invention relates to other prodrugs and variants of the compound of formula V'. These compounds are compounds of formula I, where X is:

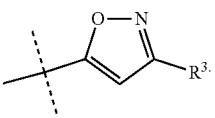

These compounds are represented by formula V:

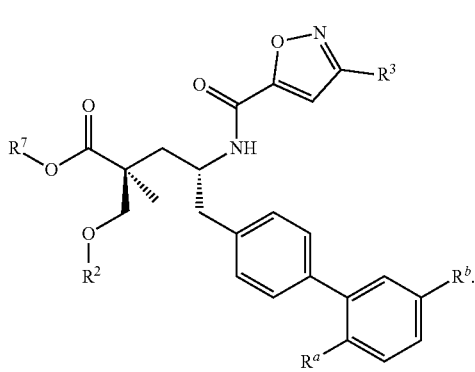

(V)

These compounds are represented by formula VIa or VIb:

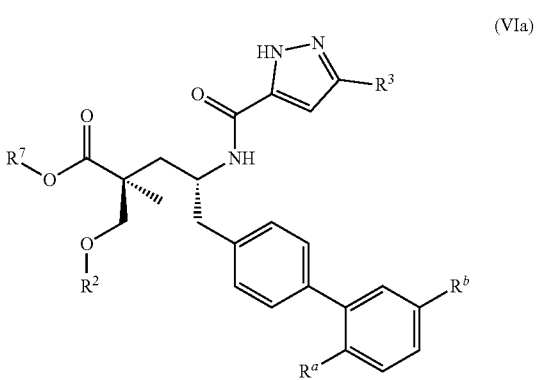

(VIa)

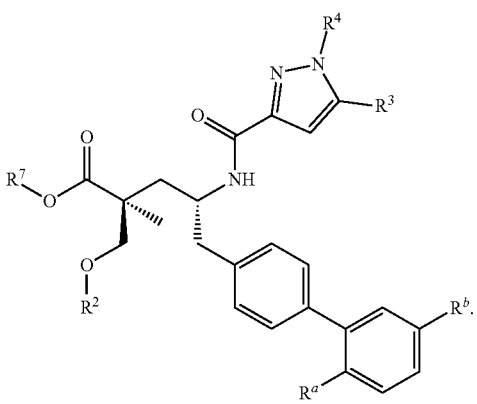

(VIb)

In one embodiment of the compounds of formula V, $R^a$ and $R^b$ are H; $R^2$ is selected from —$C_{1-6}$alkyl, —$(CH_2)_{2-3}OR^e$, and —$(CH_2)_{2-3}NR^eR^e$; $R^3$ is selected from —OH, —$OCH_3$, —$OCH_2CH_3$, and —$C_{1-4}$alkyl; and $R^7$ is H; where each $R^e$ is independently H or —$CH_3$. In one specific embodiment of the compounds of formula V, $R^a$ and $R^b$ are H, $R^2$ is —$CH_3$, $R^3$ is —OH or —$OCH_3$, and $R^7$ is H.

In another embodiment of the compounds of formula V, $R^a$ is selected from Cl and F and $R^b$ is H; or $R^a$ is H and $R^b$ is selected from Cl, F, —$CH_3$, and —CN; or $R^a$ is F and $R^b$ is Cl; $R^2$ is selected from H, —$C_{1-6}$alkyl, —$(CH_2)_{2-3}OR^e$, and —$(CH_2)_{2-3}NR^eR^e$; $R^3$ is selected from —OH, —$OCH_3$, —$OCH_2CH_3$, and —$C_{1-4}$alkyl; and $R^7$ is selected from H, —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$-cyclohexyl, —$CH_2CH(NH_2)C(O)OCH_3$, —$C_{2-4}$alkylene-$N(CH_3)_2$, —$C_{0-6}$alkylenemorpholinyl, and

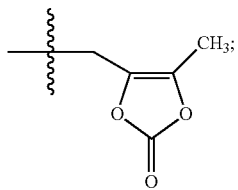

where each R is independently H or —$C_{1-3}$alkyl; each $R^d$ is independently H, —$CH_3$, —$CH(CH_3)_2$, phenyl, or benzyl; and each $R^e$ is independently H or —$CH_3$. In one specific embodiment of the compounds of formula V, $R^a$ is H, $R^b$ is Cl, $R^2$ is H, —$CH_3$, —$CH_2CH_3$ or —$(CH_2)_2OH$, $R^3$ is —OH or —$OCH_3$, and $R^7$ is H; or $R^a$ is F, $R^b$ is Cl, $R^2$ is H or —$C_{1-6}$alkyl (e.g., —$CH_3$ or —$CH_2CH_3$), $R^3$ is —OH, —$OCH_3$ or —$C_{1-4}$alkyl (e.g., —$CH_2CH_3$, —$(CH_2)_2CH_3$, or —$CH_2CH(CH_3)_2$), and $R^7$ is H.

Another aspect of the invention relates to compounds of formula I, where X is:

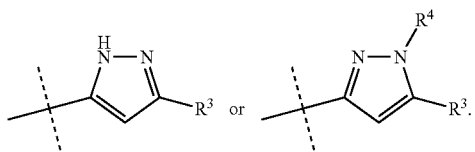

In one embodiment of the compounds of formula VI, $R^a$ is selected from Cl and F and $R^b$ is H; or $R^a$ is H and $R^b$ is selected from Cl, F, —$CH_3$, and —CN; or $R^a$ is F and $R^b$ is Cl; $R^2$ is selected from H, —$C_{1-6}$alkyl, —$(CH_2)_{2-3}OR^e$, and —$(CH_2)_{2-3}NR^eR^e$; $R^3$ is selected from —OH, —$OCH_3$, —$OCH_2CH_3$, and —$C_{1-4}$alkyl; $R^4$ is selected from H, —$C_{1-6}$alkyl, and phenyl; and $R^7$ is selected from H, —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$-cyclohexyl, —$CH_2CH(NH_2)C(O)OCH_3$, —$C_{2-4}$alkylene-$N(CH_3)_2$, —$C_{0-6}$alkylenemorpholinyl, and where each $R^c$ is independently H or —$C_{1-3}$alkyl; each $R^d$ is independently H, —$CH_3$, —$CH(CH_3)_2$, phenyl, or benzyl; and each $R^e$ is independently H or —$CH_3$. In one specific embodiment of the compounds of formula VIa and VIb, $R^a$ is H or F; $R^b$ is Cl; $R^2$ is H or —$C_{1-6}$alkyl (e.g., —$CH_3$); $R^3$ is —$OCH_3$, —$OCH_2CH_3$ or —$C_{1-4}$alkyl (e.g., —$CH(CH_3)_2$ or —$CH_2CH(CH_3)_2$)); $R^4$, if present, is H; and $R^7$ is H.

Another aspect of the invention relates to compounds of formula I, where X is:

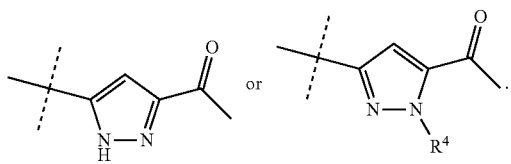

These compounds are represented by formula VIIa or VIIb:

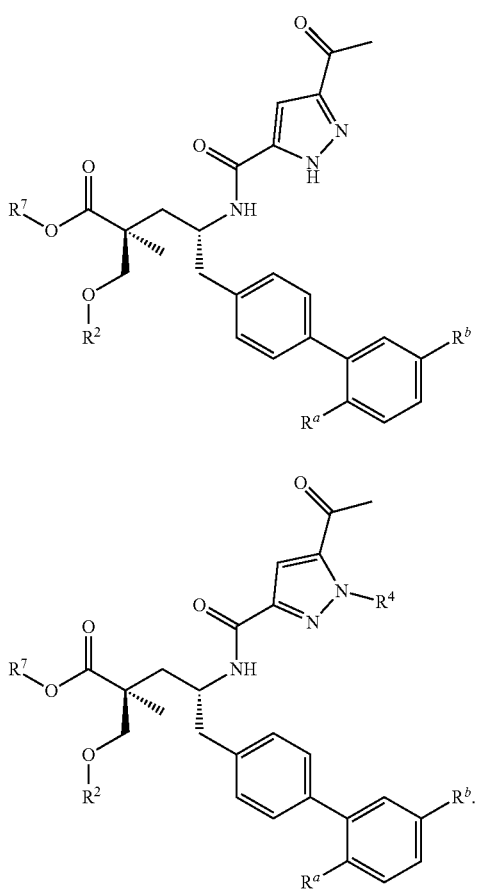

In one embodiment of the compounds of formula VII, $R^a$ is selected from Cl and F and $R^b$ is H; or $R^a$ is H and $R^b$ is selected from Cl, F, —$CH_3$, and —CN; or $R^a$ is F and $R^b$ is Cl; $R^2$ is selected from H, —$C_{1-6}$alkyl, —$(CH_2)_{2-3}OR^e$, and —$(CH_2)_{2-3}NR^eR^e$; $R^4$ is selected from H, —$C_{1-6}$alkyl, and phenyl; and $R^7$ is selected from H, —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$-cyclohexyl, —$CH_2CH(NH_2)C(O)OCH_3$, —$C_{2-4}$alkylene-N$(CH_3)_2$, —$C_{0-6}$alkylenemorpholinyl, and

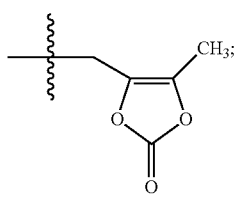

where each $R^c$ is independently H or —$C_{1-3}$alkyl; each $R^d$ is independently H, —$CH_3$, —$CH(CH_3)_2$, phenyl, or benzyl; and each $R^e$ is independently H or —$CH_3$. In one specific embodiment of the compounds of formula VIIa and VIIb, $R^a$ is F, $R^b$ is Cl, $R^2$ is H or —$C_{1-6}$alkyl (e.g., —$CH_3$ or —$CH_2CH_3$), $R^4$, if present, is H, and $R^7$ is H.

Another aspect of the invention relates to compounds of formula I, where X is:

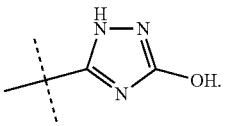

These compounds are represented by formula VIII:

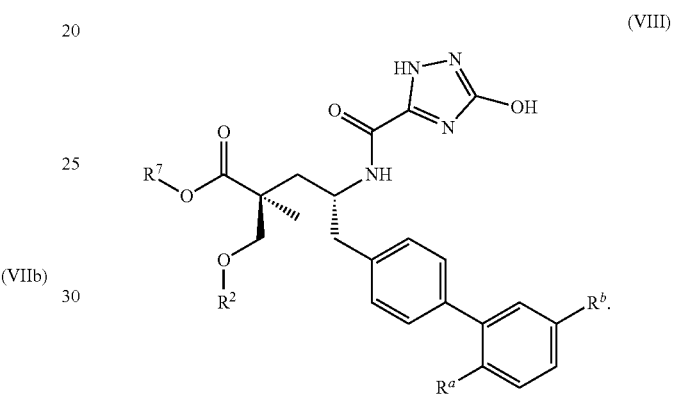

In one embodiment of the compounds of formula VIII, $R^a$ is selected from Cl and F and $R^b$ is H; or $R^a$ is H and $R^b$ is selected from Cl, F, —$CH_3$, and —CN; or $R^a$ is F and $R^b$ is Cl; $R^2$ is selected from H, —$C_{1-6}$alkyl, —$(CH_2)_{2-3}OR^e$, and —$(CH_2)_{2-3}NR^eR^e$; and $R^7$ is selected from H, —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$—cyclohexyl, —$CH_2CH(NH_2)C(O)OCH_3$, —$C_{2-4}$alkylene-N$(CH_3)_2$, —$C_{0-6}$alkylenemorpholinyl, and

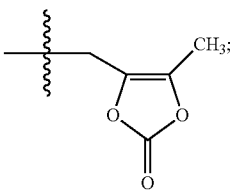

where each $R^c$ is independently H or —$C_{1-3}$alkyl; each $R^d$ is independently H, —$CH_3$, —$CH(CH_3)_2$, phenyl, or benzyl; and each $R^e$ is independently H or —$CH_3$.

Another aspect of the invention relates to compounds of formula I, where X is:

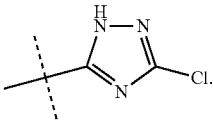

These compounds are represented by formula IX:

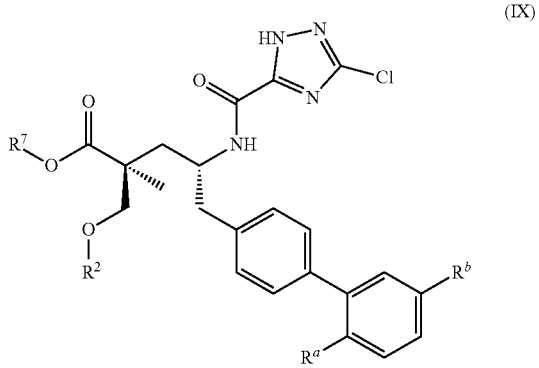

In one embodiment of the compounds of formula IX, $R^a$ is selected from Cl and F and $R^b$ is H; or $R^a$ is H and $R^b$ is selected from Cl, F, —$CH_3$, and —CN; or $R^a$ is F and $R^b$ is Cl; $R^2$ is selected from H, —$C_{1-6}$alkyl, —$(CH_2)_{2-3}OR^e$, and —$(CH_2)_{2-3}NR^eR^e$; and $R^7$ is selected from H, —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$— cyclohexyl, —$CH_2CH(NH_2)C(O)OCH_3$, —$C_{2-4}$alkylene-$N(CH_3)_2$, —$C_{0-6}$alkylenemorpholinyl, and

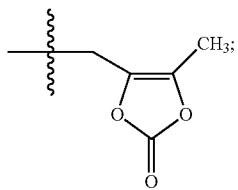

where each $R^c$ is independently H or —$C_{1-3}$alkyl; each $R^d$ is independently H, —$CH_3$, —$CH(CH_3)_2$, phenyl, or benzyl; and each $R^e$ is independently H or —$CH_3$.

General Synthetic Procedures

Compounds of the invention can be prepared from readily available starting materials using the following general methods, the procedures set forth in the Examples, or by using other methods, reagents, and starting materials that are known to those of ordinary skill in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (for example, reaction temperatures, times, mole ratios of reactants, solvents, pressures, etc.) are given, other process conditions can also be used unless otherwise stated. In some instances, reactions were conducted at room temperature and no actual temperature measurement was taken. It is understood that room temperature can be taken to mean a temperature within the range commonly associated with the ambient temperature in a laboratory environment, and will typically be in the range of about 18° C. to about 30° C. In other instances, reactions were conducted at room temperature and the temperature was actually measured and recorded. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, Protecting Groups in Organic Synthesis, Fourth Edition, Wiley, New York, 2006, and references cited therein.

Carboxy-protecting groups are suitable for preventing undesired reactions at a carboxy group, and examples include, but are not limited to, methyl, ethyl, t-butyl, benzyl (Bn), p-methoxybenzyl (PMB), 9-fluorenylmethyl (Fm), trimethylsilyl (TMS), t-butyldimethylsilyl (TBDMS), diphenylmethyl (benzhydryl, DPM) and the like. Amino-protecting groups are suitable for preventing undesired reactions at an amino group, and examples include, but are not limited to, t-butoxycarbonyl (BOC), trityl (Tr), benzyloxycarbonyl (Cbz), 9-fluorenylmethoxycarbonyl (Fmoc), formyl, trimethylsilyl (TMS), t-butyldimethylsilyl (TBDMS), and the like. Hydroxyl-protecting groups are suitable for preventing undesired reactions at a hydroxyl group, and examples include, but are not limited to $C_{1-6}$alkyls, silyl groups including tri$C_{1-6}$alkylsilyl groups, such as trimethylsilyl (TMS), triethylsilyl (TES), and tert-butyldimethylsilyl (TBDMS); esters (acyl groups) including $C_{1-6}$alkanoyl groups, such as formyl, acetyl, and pivaloyl, and aromatic acyl groups such as benzoyl; arylmethyl groups such as benzyl (Bn), p-methoxybenzyl (PMB), 9-fluorenylmethyl (Fm), and diphenylmethyl (benzhydryl, DPM); and the like.

Standard deprotection techniques and reagents are used to remove the protecting groups, and may vary depending upon which group is used. For example, sodium or lithium hydroxide is commonly used when the carboxy-protecting group is methyl, an acid such as TFA or HCl (e.g., 4.0 M HCl in 1,4-dioxane) is commonly used when the carboxy-protecting group is ethyl or t-butyl, and $H_2$/Pd/C may be used when the carboxy-protecting group is benzyl. A BOC amino-protecting group can be removed using an acidic reagent such as TFA in DCM or HCl in 1,4-dioxane, while a Cbz amino-protecting group can be removed by employing catalytic hydrogenation conditions such as $H_2$ (1 atm) and 10% Pd/C in an alcoholic solvent ("$H_2$/Pd/C"). $H_2$/Pd/C is commonly used when the hydroxyl-protecting group is benzyl, while NaOH is commonly used when the hydroxyl-protecting group is an acyl group.

Leaving groups are functional groups or atoms that can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

Suitable bases for use in these schemes include, by way of illustration and not limitation, potassium carbonate, calcium carbonate, sodium carbonate, triethylamine (Et₃N), pyridine, 1,8-diazabicyclo-[5.4.0]undec-7-ene (DBU), N,N-diisopropylethylamine (DIPEA), 4-methylmorpholine, sodium hydroxide, potassium hydroxide, potassium t-butoxide, and metal hydrides.

Suitable inert diluents or solvents for use in these schemes include, by way of illustration and not limitation, tetrahydrofuran (THF), acetonitrile (MeCN), N,N-dimethylformamide (DMF), N,N-dimethylacetamide (DMA), dimethyl sulfoxide (DMSO), toluene, dichloromethane (DCM), chloroform (CHCl₃), carbon tetrachloride (CCl₄), 1,4-dioxane, methanol, ethanol, water, diethyl ether, acetone, and the like.

Suitable carboxylic acid/amine coupling reagents include benzotriazol-1-yloxytris(dimethylamino)phosphonium hexafluorophosphate (BOP), benzotriazol-1-yloxytripyrrolidinophosphonium hexafluorophosphate (PyBOP), N,N,N',N'-tetramethyl-O-(7-azabenzotriazol-1-yl)uronium hexafluorophosphate (HATU), 1,3-dicyclohexylcarbodiimide (DCC), N-(3-dimethylaminopropyl)-N'-ethylcarbodiimide (EDC), carbonyldiimidazole (CDI), 1-hydroxybenzotriazole (HOBt), and the like. Coupling reactions are conducted in an inert diluent in the presence of a base such as DIPEA, and are performed under conventional amide bond-forming conditions.

All reactions are typically conducted at a temperature within the range of about −78 C to 100° C., for example at room temperature. Reactions may be monitored by use of thin layer chromatography (TLC), high performance liquid chromatography (HPLC), and/or LCMS until completion. Reactions may be complete in minutes, or may take hours, typically from 1-2 hours and up to 48 hours. Upon completion, the resulting mixture or reaction product may be further treated in order to obtain the desired product. For example, the resulting mixture or reaction product may be subjected to one or more of the following procedures: concentrating or partitioning (for example, between EtOAc and water or between 5% THF in EtOAc and 1M phosphoric acid); extraction (for example, with EtOAc, CHCl₃, DCM, chloroform); washing (for example, with saturated aqueous NaCl, saturated aqueous NaHCO₃, Na₂CO₃ (5%), CHCl₃ or 1M NaOH); drying (for example, over MgSO₄, over Na₂SO₄, or in vacuo); filtering; crystallizing (for example, from EtOAc and hexanes); being concentrated (for example, in vacuo); and/or purification (e.g., silica gel chromatography, flash chromatography, preparative HPLC, reverse phase-HPLC, or crystallization).

By way of illustration, compounds of formula I, as well as their salts, can be prepared as shown in Schemes I-IV.

Scheme I

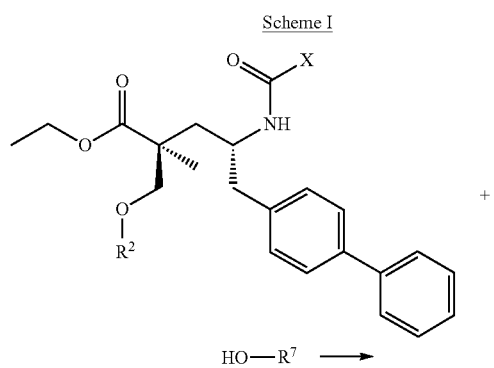

HO—R⁷ ⟶

+

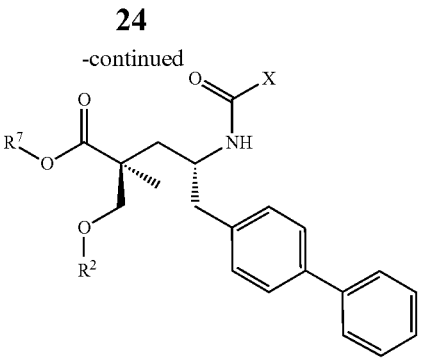

Scheme I is a transesterification reactions. Generally, this reaction involves reacting the ester with heat, the desired alcohol (HO-R⁷) and a suitable acid catalyst, for example hydrochloric acid. The HO—R⁷ alcohols are either commercially available or can be prepared by techniques that are known in the art or described herein. Exemplary HO—R⁷ groups include HO—CH₂CF₂CH₃, HO—CH₂CF₂CF₃, and

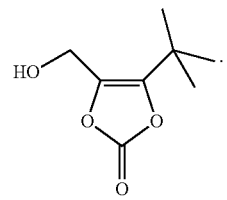

Scheme II

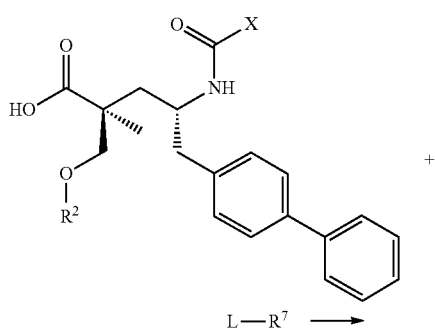

L—R⁷ ⟶

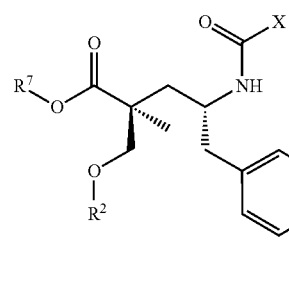

Scheme II is a nucleophilic substitution reaction, where L is a suitable leaving group. Generally, this reaction is conducted in the presence of a suitable base such as triethylamine in a suitable inert diluent or solvent such as acetone. The L-R⁷ compound is either commercially available or can be prepared by techniques that are known in the art or described herein.

Scheme III

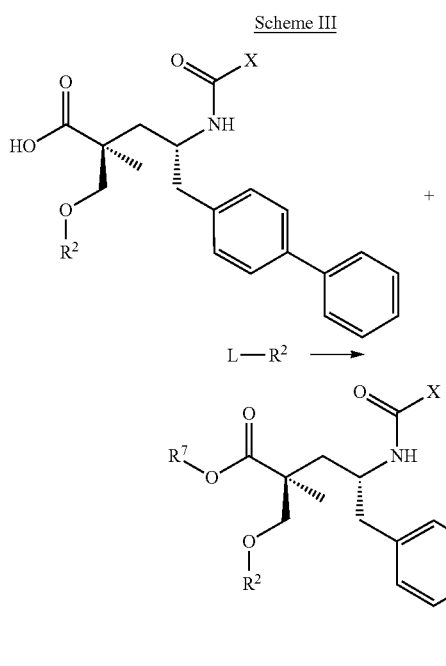

Scheme III is a nucleophilic substitution reaction, where L is a suitable leaving group. Generally, this reaction is conducted in the presence of a suitable base such as N,N-diisopropylethylamine in a suitable inert diluent or solvent such as dichloromethane. The L-R² compound is either commercially available or can be prepared by techniques that are known in the art or described herein. Exemplary L-R² compounds include Cl—C(O)—CH₃, Cl—C(O)—CH(CH₃)₂, and Cl—C(O)—CH₂CH(CH₃)₂.

Scheme IV

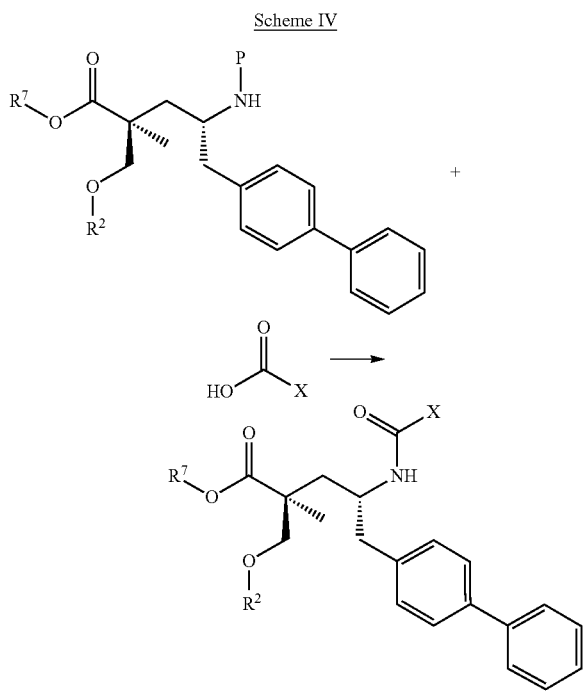

Scheme IV is a coupling reaction, where P is H or a suitable amino-protecting group. When P is an amino protecting group, the process further comprises deprotecting the compound, before or in situ with the coupling step. Exemplary coupling reagents include HATU and HOBt with EDC. Generally, this reaction is conducted in the presence of a base such as DIPEA or 4-methylmorpholine, and an inert diluent or solvents such as DMF or DMA. The carboxylic acid starting materials are generally commercially available or can be prepared using procedures that are known in the art.

By way of illustration, compounds of formulas II-X, as well as their salts, can be prepared as shown in Scheme V.

Scheme V

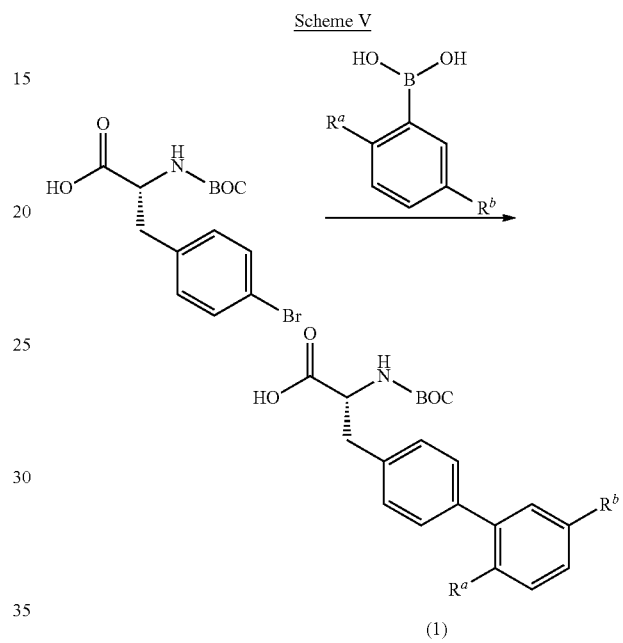

(R)-3-(4-bromophenyl)-2-t-butoxycarbonylaminopropionic acid and the desired halophenylboronic acid are combined with a palladium catalyst in an inert diluent in the presence of an a suitable base such as potassium carbonate or sodium carbonate. Exemplary halophenylboronic acids are 2-fluorophenylboronic acid, 3-fluorophenylboronic acid, 2-chlorophenylboronic acid, 3-chlorophenylboronic acid, and 2-fluoro-5-chlorophenylboronic acid. Exemplary palladium catalysts include 1,1-bis(diphenylphosphino) ferrocene palladium chloride, dichlorobis(triphenylphosphine) palladium (II), bis(tri-t-butylphosphine) palladium(0), and tetrakis(triphenylphosphine) palladium(0).

Compound 1 is then converted to Compound 5 (where P is H or a suitable amino-protecting group) by a several step process, which is detailed in the Examples section.

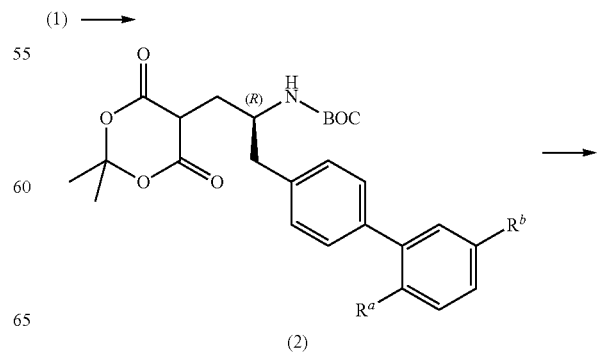

-continued

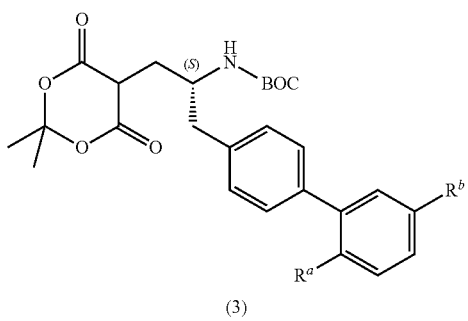

(3)

(3) →

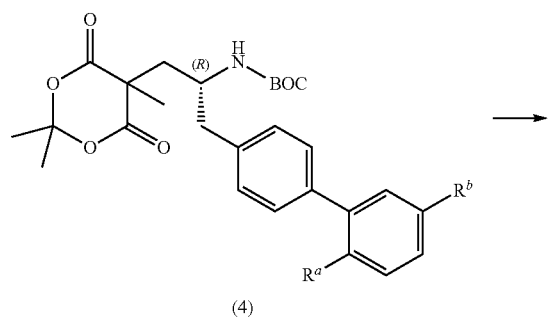

(4)

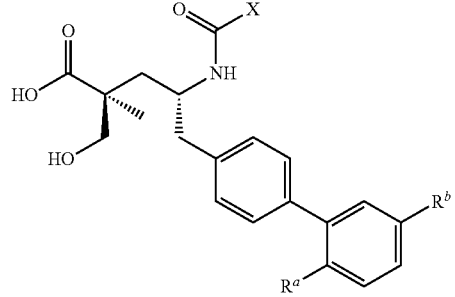

(5)

Finally, Compound 5 is coupled with the desired X group as described above in Scheme IV:

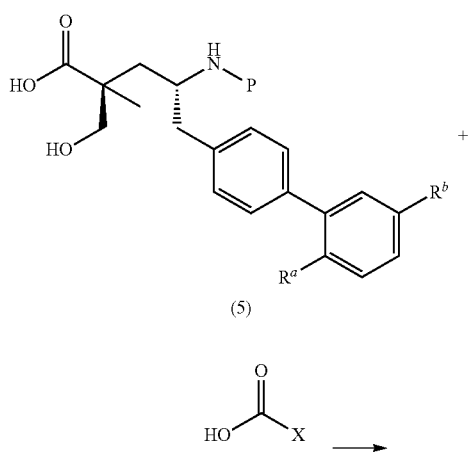

-continued

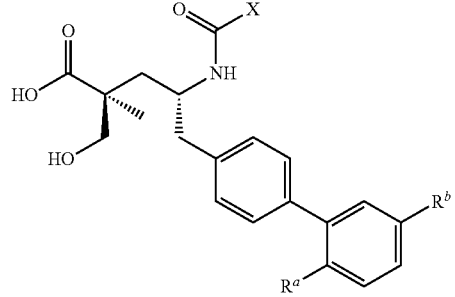

Further details regarding specific reaction conditions and other procedures for preparing representative compounds of the invention or intermediates thereof are described in the Examples set forth below.

UTILITY

The compound of formula I' has activity as a neprilysin inhibitor, and is expected to have therapeutic utility as a neprilysin inhibitor. Prodrugs of this compound, once metabolized in vivo, are expected to have the same utility. Thus, when discussing the activity of the compounds of the invention, it is understood that these prodrugs have the expected activity once metabolized.

Exemplary assays include by way of illustration and not limitation, assays that measure NEP inhibition. Useful secondary assays include assays to measure ACE inhibition and aminopeptidase P (APP) inhibition (e.g., as described in Sulpizio et al. (2005) *JPET* 315:1306-1313). A pharmacodynamic assay to assess the in vivo inhibitory potencies for ACE and NEP in anesthetized rats is described in Seymour et al. (1985) *Hypertension* 7(Suppl I):I-35-I-42 and Wigle et al. (1992) *Can. J Physiol. Pharmacol.* 70:1525-1528), where ACE inhibition is measured as the percent inhibition of the angiotensin I pressor response and NEP inhibition is measured as increased urinary cyclic guanosine 3',5'-monophosphate (cGMP) output.

There are also many in vivo assays that can be used. The conscious spontaneously hypertensive rat (SHR) model is a renin dependent hypertension model. See for example, Intengan et al. (1999) *Circulation* 100(22):2267-2275 and Badyal et al. (2003) *Indian Journal of Pharmacology* 35:349-362. The conscious desoxycorticosterone acetate-salt (DOCA-salt) rat model is a volume dependent hypertension model that is useful for measuring NEP activity. See for example, Trapani et al. (1989) *J Cardiovasc. Pharmacol.* 14:419-424, Intengan et al. (1999) *Hypertension* 34(4):907-913, and Badyal et al. (2003) supra). The DOCA-salt model is particularly useful for evaluating the ability of a test compound to reduce blood pressure as well as to measure a test compound's ability to prevent or delay a rise in blood pressure. The Dahl salt-sensive (DSS) hypertensive rat model is a model of hypertension that is sensitive to dietary salt (NaCl), and is described, for example, in Rapp (1982) *Hypertension* 4:753-763. The rat monocrotaline model of pulmonary arterial hypertension described, for example, in Kato et al. (2008) *J. Cardiovasc. Pharmacol.* 51(1):18-23, is a reliable predictor of clinical efficacy for the treatment of pulmonary arterial hypertension. Heart failure animal models include the DSS rat model for heart failure and the aorto-caval fistula model (AV shunt), the latter of which is described, for example, in Norling et al. (1996) *J. Amer. Soc. Nephrol.* 7:1038-1044. Other animal models, such as the hot plate, tail-flick and formalin tests, can be used to measure the analgesic properties of a compound, as well as the spinal nerve ligation (SNL) model of neuropathic pain. See, for example, Malmberg et al. (1999) *Current Protocols in Neuroscience* 8.9.1-8.9.15. Other properties and utilities of the compounds can be demonstrated using various in vitro and in vivo assays well known to those skilled in the art.

The compounds of the invention are expected to be useful for the treatment and/or prevention of medical conditions responsive to NEP inhibition. Thus it is expected that patients suffering from a disease or disorder that is treated by inhibiting the NEP enzyme or by increasing the levels of its peptide substrates, can be treated by administering a therapeutically effective amount of a compound of the invention. For example, by inhibiting NEP, the compound is expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. Thus, the compounds are expected to have other physiological actions, for example, on the renal, central nervous, reproductive and gastrointestinal systems.

Cardiovascular Diseases

By potentiating the effects of vasoactive peptides like the natriuretic peptides and bradykinin, compounds of the invention are expected to find utility in treating and/or preventing medical conditions such as cardiovascular diseases. See, for example, Roques et al. (1993) *Pharmacol. Rev.* 45:87-146 and Dempsey et al. (2009) *Amer. J. of Pathology* 174(3):782-796. Cardiovascular diseases of particular interest include hypertension and heart failure. Hypertension includes, by way of illustration and not limitation: primary hypertension, which is also referred to as essential hypertension or idiopathic hypertension; secondary hypertension; hypertension with accompanying renal disease; severe hypertension with or without accompanying renal disease; pulmonary hypertension, including pulmonary arterial hypertension; and resistant hypertension. Heart failure includes, by way of illustration and not limitation: congestive heart failure; acute heart failure; chronic heart failure, for example with reduced left ventricular ejection fraction (also referred to as systolic heart failure) or with preserved left ventricular ejection fraction (also referred to as diastolic heart failure); and acute and chronic decompensated heart failure, with or without accompanying renal disease. Thus, one embodiment of the invention relates to a method for treating hypertension, particularly primary hypertension or pulmonary arterial hypertension, comprising administering to a patient a therapeutically effective amount of a compound of the invention.

For treatment of primary hypertension, the therapeutically effective amount is typically the amount that is sufficient to lower the patient's blood pressure. This would include both mild-to-moderate hypertension and severe hypertension. When used to treat hypertension, the compound may be administered in combination with other therapeutic agents such as aldosterone antagonists, angiotensin-converting enzyme inhibitors and dual-acting angiotensin-converting enzyme/neprilysin inhibitors, angiotensin-converting enzyme 2 (ACE2) activators and stimulators, angiotensin-II vaccines, anti-diabetic agents, anti-lipid agents, anti-thrombotic agents, $AT_1$ receptor antagonists and dual-acting $AT_1$ receptor antagonist/neprilysin inhibitors, $\beta_1$-adrenergic receptor antagonists, dual-acting β-adrenergic receptor antagonist/$\alpha_1$-receptor antagonists, calcium channel blockers, diuretics, endothelin receptor antagonists, endothelin converting enzyme inhibitors, neprilysin inhibitors, natriuretic peptides and their analogs, natriuretic peptide clearance receptor antagonists, nitric oxide donors, non-steroidal anti-inflammatory agents, phosphodiesterase inhibitors (specifically PDE-V inhibitors), prostaglandin receptor agonists, renin inhibitors, soluble guanylate cyclase stimulators and activators, and combinations thereof. In one particular embodiment of the invention, a compound of the invention is combined with an $AT_1$ receptor antagonist, a diuretic, a calcium channel blocker, or a combination thereof, and used to treat primary hypertension. In another particular embodiment of the invention, a compound of the invention is combined with an $AT_1$ receptor antagonist, and used to treat hypertension with accompanying renal disease.

For treatment of pulmonary arterial hypertension, the therapeutically effective amount is typically the amount that is sufficient to lower the pulmonary vascular resistance. Other goals of therapy are to improve a patient's exercise capacity. For example, in a clinical setting, the therapeutically effective amount can be the amount that improves a patient's ability to walk comfortably for a period of 6 minutes (covering a distance of approximately 20-40 meters). When used to treat pulmonary arterial hypertension the compound may be administered in combination with other therapeutic agents such as α-adrenergic antagonists, $\beta_1$-adrenergic receptor antagonists, $\beta_2$-adrenergic receptor agonists, angiotensin-converting enzyme inhibitors, anticoagulants, calcium channel blockers, diuretics, endothelin receptor antagonists, PDE-V inhibitors, prostaglandin analogs, selective serotonin reuptake inhibitors, and combinations thereof. In one particular embodiment of the invention, a compound of the invention is combined with a PDE-V inhibitor or a selective serotonin reuptake inhibitor and used to treat pulmonary arterial hypertension.

Another embodiment of the invention relates to a method for treating heart failure, in particular congestive heart failure (including both systolic and diastolic congestive heart failure), comprising administering to a patient a therapeutically effective amount of a compound of the invention. Typically, the therapeutically effective amount is the amount that is sufficient to lower blood pressure and/or improve renal functions. In a clinical setting, the therapeutically effective amount can be the amount that is sufficient to improve cardiac hemodynamics, like for instance reduction in wedge pressure, right atrial pressure, filling pressure, and vascular resistance. In one embodiment, the compound is administered as an intravenous dosage form. When used to treat heart failure, the compound may be administered in combination with other therapeutic agents such as adenosine receptor antagonists, advanced glycation end product breakers, aldosterone antagonists, $AT_1$ receptor antagonists, $\beta_1$-adrenergic receptor antagonists, dual-acting β-adrenergic receptor antagonist/$\alpha_1$-receptor antagonists, chymase inhibitors, digoxin, diuretics, endothelin converting enzyme (ECE) inhibitors, endothelin receptor antagonists, natriuretic peptides and their analogs, natriuretic peptide clearance receptor antagonists, nitric oxide donors, prostaglandin analogs, PDE-V inhibitors, soluble guanylate cyclase activators and stimulators, and vasopressin receptor antagonists. In one particular embodiment of the invention, a compound of the invention is combined with an aldosterone antagonist, a $\beta_1$-adrenergic receptor antagonist, an $AT_1$ receptor antagonist, or a diuretic, and used to treat congestive heart failure.

Diarrhea

As NEP inhibitors, compounds of the invention are expected to inhibit the degradation of endogenous enkephalins and thus such compounds may also find utility for the treatment of diarrhea, including infectious and secretory/watery diarrhea. See, for example, Baumer et al. (1992) Gut 33:753-758; Farthing (2006) *Digestive Diseases* 24:47-58; and Marcais-Collado (1987) *Eur. J Pharmacol.* 144(2): 125-132. When used to treat diarrhea, compounds of the invention may be combined with one or more additional antidiarrheal treatments.

Renal Diseases

By potentiating the effects of vasoactive peptides like the natriuretic peptides and bradykinin, compounds of the invention are expected to enhance renal function (see Chen et al. (1999) *Circulation* 100:2443-2448; Lipkin et al. (1997) *Kidney Int.* 52:792-801; and Dussaule et al. (1993) *Clin. Sci.* 84:31-39) and find utility in treating and/or preventing renal diseases. Renal diseases of particular interest include diabetic nephropathy, chronic kidney disease, proteinuria, and particularly acute kidney injury or acute renal failure (see Sharkovska et al. (2011) *Clin. Lab.* 57:507-515 and Newaz et al. (2010) *Renal Failure* 32:384-390). When used to treat renal disease, the compound may be administered in combination with other therapeutic agents such as angiotensin-converting enzyme inhibitors, $AT_1$ receptor antagonists, and diuretics.

Preventative Therapy

By potentiating the effects of the natriuretic peptides, compounds of the invention are also expected to be useful in preventative therapy, due to the antihypertrophic and anti-fibrotic effects of the natriuretic peptides (see Potter et al. (2009) *Handbook of Experimental Pharmacology* 191:341-366), for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

Glaucoma

By potentiating the effects of the natriuretic peptides, compounds of the invention are expected to be useful to treat glaucoma. See, for example, Diestelhorst et al. (1989) *International Ophthalmology* 12:99-101. When used to treat glaucoma, compounds of the invention may be combined with one or more additional anti-glaucoma agents.

Pain Relief

As NEP inhibitors, compounds of the invention are expected to inhibit the degradation of endogenous enkephalins and thus such compounds may also find utility as analgesics. See, for example, Roques et al. (1980) *Nature* 288:286-288 and Thanawala et al. (2008) *Current Drug Targets* 9:887-894. When used to treat pain, compounds of the invention may be combined with one or more additional antinociceptive drugs such as aminopeptidase N or dipeptidyl peptidase III inhibitors, non-steroidal anti-inflammatory agents, monoamine reuptake inhibitors, muscle relaxants, NMDA receptor antagonists, opioid receptor agonists, $5\text{-HT}_{1D}$ serotonin receptor agonists, and tricyclic antidepressants.

Other Utilities

Due to their NEP inhibition properties, compounds of the invention are also expected to be useful as antitussive agents, as well as find utility in the treatment of portal hypertension associated with liver cirrhosis (see Sansoe et al. (2005) *J. Hepatol.* 43:791-798), cancer (see Vesely (2005) *J. Investigative Med.* 53:360-365), depression (see Noble et al. (2007) *Exp. Opin. Ther. Targets* 11:145-159), menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the compounds of the invention are expected to be useful in treating female sexual dysfunction (see Pryde et al. (2006) *J. Med. Chem.* 49:4409-4424), which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, compounds of the invention may be combined with one or more of the following secondary agents: PDE-V inhibitors, dopamine agonists, estrogen receptor agonists and/or antagonists, androgens, and estrogens. Due to their NEP inhibition properties, compounds of the invention are also expected to have anti-inflammatory properties, and are expected to have utility as such, particularly when used in combination with statins.

Recent studies suggest that NEP plays a role in regulating nerve function in insulin-deficient diabetes and diet induced obesity. Coppey et al. (2011) *Neuropharmacology* 60:259-266. Therefore, due to their NEP inhibition properties, compounds of the invention are also expected to be useful in providing protection from nerve impairment caused by diabetes or diet induced obesity.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Research Tools

Since the compounds of the invention are metabolized in vivo to compounds having activity as neprilysin inhibitors, they are also useful as a research tools for investigating or studying biological systems or samples having a NEP enzyme, for example to study diseases where the NEP enzyme or its peptide substrates plays a role. Accordingly, one aspect of the invention relates to a method of using a compound of the invention as a research tool, comprising conducting a biological assay using a compound of the invention. Any suitable biological system or sample having a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, NEP enzyme activity in a mammal is inhibited by administering a NEP-inhibiting amount of a compound of the invention. These compounds can also be used as research tools by conducting biological assays using such compounds.

When used as a research tool, a biological system or sample comprising a NEP enzyme is typically contacted with a NEP enzyme-inhibiting amount of a compound of the invention. After the biological system or sample is exposed to the compound, the effects of inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the crystalline compound to a mammal, for example by i.p., p.o, i.v., s.c., or inhaled administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as enzyme activity assays and measuring enzyme substrate or product mediated changes in functional assays. The assay results can be used to determine the activity level as well as the amount of compound necessary to achieve the desired result, that is, a NEP enzyme-inhibiting amount. Typically, the determining step will involve determining the effects of inhibiting the NEP enzyme.

Additionally, the compounds of the invention can be used as research tools for evaluating other chemical compounds, and thus are also useful in screening assays to discover, for example, new compounds having NEP-inhibiting activity. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a NEP enzyme inhibition assay. In this manner, the compounds of the invention are used as standards in an assay to allow comparison of the results obtained with a test compound and with the compound of the invention to identify those test compounds that have about equal or superior activity, if any. For example, $pK_i$ data for a test compound or a group of test compounds is compared to the $pK_i$ data for a compound of the invention to identify those test compounds that have the desired properties, for example, test compounds having a $pK_i$ value about equal or superior to the compound of the invention, if any. This aspect of the invention includes, as separate embodiments, both the generation of comparison data (using the appropriate assays) and the analysis of test data to identify test compounds of interest.

Still another aspect of the invention relates to a method of studying a biological system or sample comprising a NEP enzyme, the method comprising: (a) contacting the biological system or sample with a compound of the invention; and (b) determining the effects caused by the compound on the biological system or sample.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compounds of the invention may be administered, for example orally, in multiple doses per day (for example, two, three, or four times daily), in a single daily dose or a single weekly dose. It will be understood that any form of the compounds of the invention, (that is, free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts, solvates and prodrugs of that compound.

The pharmaceutical compositions of the invention typically contain a therapeutically effective amount of a compound of the invention. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in micro-encapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's airstream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages, or dimerization of thiols that may be present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more $\alpha$-D-glucopyranose units linked at the 1,4 positions by a linkages as in amylase, $\beta$-cyclodextrin or cycloheptaamylose. Exemplary cyclodextrins include cyclodextrin derivatives such as hydroxypropyl and sulfobutyl ether cyclodextrins such as hydroxypropyl-$\beta$-cyclodextrin and sulfobutyl ether $\beta$-cyclodextrin. Exemplary buffers for such formulations include carboxylic acid-based buffers such as citrate, lactate and maleate buffer solutions.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Secondary Agents

The compounds of the invention may be useful as the sole treatment of a disease or may be combined with one or more additional therapeutic agents in order to obtain the desired therapeutic effect. Thus, in one embodiment, pharmaceutical compositions of the invention contain other drugs that are co-administered with a compound of the invention. For example, the composition may further comprise one or more drugs (also referred to as "secondary agents(s)"). Such therapeutic agents are well known in the art, and include adenosine receptor antagonists, $\alpha$-adrenergic receptor antagonists, $\beta_1$-adrenergic receptor antagonists, $\beta_2$-adrenergic receptor agonists, dual-acting $\beta$-adrenergic receptor antagonist/$\alpha_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, anti-diabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof. Specific examples of these agents are detailed herein.

Accordingly, in yet another aspect of the invention, a pharmaceutical composition comprises a compound of the invention, a second active agent, and a pharmaceutically acceptable carrier. Third, fourth etc. active agents may also be included in the composition. In combination therapy, the amount of compound of the invention that is administered, as well as the amount of secondary agents, may be less than the amount typically administered in monotherapy.

Compounds of the invention may be physically mixed with the second active agent to form a composition containing both agents; or each agent may be present in separate and distinct compositions which are administered to the patient simultaneously or at separate times. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (for example, one hour later or three hours later). It is also contemplated that the secondary agent may be administered more than 24 hours after administration of the compound of the invention. Alternatively, the combination may be administered by different routes of administration, that is, one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with a compound of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, compounds of the invention are administered in combination with an adenosine receptor antagonist, representative examples of which include, but are not limited to, naxifylline, rolofylline, SLV-320, theophylline, and tonapofylline.

In one embodiment, compounds of the invention are administered in combination with an α-adrenergic receptor antagonist, representative examples of which include, but are not limited to, doxazosin, prazosin, tamsulosin, and terazosin.

Compounds of the invention may also be administered in combination with a $β_1$-adrenergic receptor antagonist ("$β_1$-blockers"). Representative Pi-blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, μmolol, toliprolol, xibenolol, and combinations thereof. In one particular embodiment, the $β_1$-antagonist is selected from atenolol, bisoprolol, metoprolol, propranolol, sotalol, and combinations thereof. Typically, the Pi-blocker will be administered in an amount sufficient to provide from about 2-900 mg per dose.

In one embodiment, compounds of the invention are administered in combination with a $β_2$-adrenergic receptor agonist, representative examples of which include, but are not limited to, albuterol, bitolterol, fenoterol, formoterol, indacaterol, isoetharine, levalbuterol, metaproterenol, pirbuterol, salbutamol, salmefamol, salmeterol, terbutaline, vilanterol, and the like Typically, the $β_2$-adrenergic receptor agonist will be administered in an amount sufficient to provide from about 0.05-500 μg per dose.

In one embodiment, compounds of the invention are administered in combination with an advanced glycation end product (AGE) breaker, examples of which include, by way of illustration and not limitation, alagebrium (or ALT-711), and TRC4149.

In another embodiment, compounds of the invention are administered in combination with an aldosterone antagonist, representative examples of which include, but are not limited to, eplerenone, spironolactone, and combinations thereof. Typically, the aldosterone antagonist will be administered in an amount sufficient to provide from about 5-300 mg per day.

In one embodiment, compounds of the invention are administered in combination with an aminopeptidase N or dipeptidyl peptidase III inhibitor, examples of which include, by way of illustration and not limitation, bestatin and PC18 (2-amino-4-methylsulfonyl butane thiol, methionine thiol).

Compounds of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltipril, pentopril, perindopril, quinapril, quinaprilat, ramipril, ramiprilat, saralasin acetate, spirapril, temocapril, trandolapril, zofenopril, and combinations thereof.

In a particular embodiment, the ACE inhibitor is selected from: benazepril, captopril, enalapril, lisinopril, ramipril, and combinations thereof. Typically, the ACE inhibitor will be administered in an amount sufficient to provide from about 1-150 mg per day. In another embodiment, compounds of the invention are administered in combination with a dual-acting angiotensin-converting enzyme/neprilysin (ACE/NEP) inhibitor, examples of which include, but are not limited to: AVE-0848 ((4S,7S,12bR)-7-[3-methyl-2(S)-sulfanylbutyramido]-6-oxo-1,2,3,4,6,7,8,12b-octahydropyrido[2,1-a][2]-benzazepine-4-carboxylic acid); AVE-7688 (ilepatril) and its parent compound; BMS-182657 (2-[2-oxo-3(S)-[3-phenyl-2(S)-sulfanylpropionamido]-2,3,4,5-tetrahydro-1H-1-benzazepin-1-yl]acetic acid); CGS-35601 (N-[1-[4-methyl-2(S)-sulfanylpentanamido]cyclopentyl-carbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4a,7α(R*), 12b]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(S)-(mercaptomethyl)-3(R)-phenylbutyl]-L-alanine); sampatrilat; SA-898 ((2R,4R)—N-[2-

(2-hydroxyphenyl)-3-(3-mercaptopropionyl)thiazolidin-4-ylcarbonyl]-L-phenylalanine); Sch-50690 (N-[1 (S)-carboxy-2-[N2-(methanesulfonyl)-L-lysylamino]ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

In one embodiment, compounds of the invention are administered in combination with an angiotensin-converting enzyme 2 (ACE2) activator or stimulator.

In one embodiment, compounds of the invention are administered in combination with an angiotensin-II vaccine, examples of which include, but are not limited to ATR12181 and CYT006-AngQb.

In one embodiment, compounds of the invention are administered in combination with an anticoagulant, representative examples of which include, but are not limited to: coumarins such as warfarin; heparin; and direct thrombin inhibitors such as argatroban, bivalirudin, dabigatran, and lepirudin.

In yet another embodiment, compounds of the invention are administered in combination with an anti-diabetic agent. Representative anti-diabetic agents include injectable drugs as well as orally effective drugs, and combinations thereof. Examples of injectable drugs include, but are not limited to, insulin and insulin derivatives. Examples of orally effective drugs include, but are not limited to: biguanides such as metformin; glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In another embodiment, compounds of the invention are administered in combination with antidiarrheal treatments. Representative treatment options include, but are not limited to, oral rehydration solutions (ORS), loperamide, diphenoxylate, and bismuth subsalicylate.

In yet another embodiment, a compound of the invention is administered in combination with an anti-glaucoma agent. Representative anti-glaucoma agents include, but are not limited to: α-adrenergic agonists such as brimonidine; $\beta_1$-adrenergic receptor antagonists; topical Pi-blockers such as betaxolol, levobunolol, and μmolol; carbonic anhydrase inhibitors such as acetazolamide, brinzolamide, or dorzolamide; cholinergic agonists such as cevimeline and DMXB-anabaseine; epinephrine compounds; miotics such as pilocarpine; and prostaglandin analogs.

In yet another embodiment, compounds of the invention are administered in combination with an anti-lipid agent. Representative anti-lipid agents include, but are not limited to: cholesteryl ester transfer protein inhibitors (CETPs) such as anacetrapib, dalcetrapib, and torcetrapib; statins such as atorvastatin, fluvastatin, lovastatin, pravastatin, rosuvastatin and simvastatin; and combinations thereof.

In one embodiment, compounds of the invention are administered in combination with an anti-thrombotic agent. Representative anti-thrombotic agents include, but are not limited to: aspirin; anti-platelet agents such as clopidogrel, prasugrel, and ticlopidine; heparin; and combinations thereof.

In one embodiment, compounds of the invention are administered in combination with an $AT_1$ receptor antagonist, also known as angiotensin II type 1 receptor blockers (ARBs). Representative ARBs include, but are not limited to, abitesartan, azilsartan (e.g., azilsartan medoxomil), benzyllosartan, candesartan, candesartan cilexetil, elisartan, embusartan, enoltasosartan, eprosartan, EXP3174, fonsartan, forasartan, glycyllosartan, irbesartan, isoteoline, losartan, medoxomil, milfasartan, olmesartan (e.g., olmesartan medoxomil), opomisartan, pratosartan, ripisartan, saprisartan, saralasin, sarmesin, TAK-591, tasosartan, telmisartan, valsartan, zolasartan, and combinations thereof. In a particular embodiment, the ARB is selected from azilsartan medoxomil, candesartan cilexetil, eprosartan, irbesartan, losartan, olmesartan medoxomil, saprisartan, tasosartan, telmisartan, valsartan, and combinations thereof. Exemplary salts and/or prodrugs include candesartan cilexetil, eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

Compounds of the invention may also be administered in combination with a dual-acting agent, such as an $AT_1$ receptor antagonist/neprilysin inhibitor (ARB/NEP) inhibitor, examples of which include, but are not limited to, compounds described in U.S. Publication Nos. 2008/0269305 and 2009/0023228, both to Allegretti et al. filed on Apr. 23, 2008, such as the compound, 4'-{2-ethoxy-4-ethyl-5-[((S)-2-mercapto-4-methylpentanoylamino)-methyl]imidazol-1-ylmethyl}-3'-fluorobiphenyl-2-carboxylic acid.

Compounds of the invention may also be administered in combination with multifunctional angiotensin receptor blockers as described in Kurtz & Klein (2009) *Hypertension Research* 32:826-834.

In one embodiment, compounds of the invention are administered in combination with a bradykinin receptor antagonist, for example, icatibant (HOE-140). It is expected that this combination therapy may present the advantage of preventing angioedema or other unwanted consequences of elevated bradykinin levels.

In one embodiment, compounds of the invention are administered in combination with a calcium channel blocker. Representative calcium channel blockers include, but are not limited to, amlodipine, anipamil, aranipine, bamidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexiline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof. Typically, the calcium channel blocker will be administered in an amount sufficient to provide from about 2-500 mg per dose.

In one embodiment, compounds of the invention are administered in combination with a chymase inhibitor, such as TPC-806 and 2-(5-formylamino-6-oxo-2-phenyl-1,6-dihydropyrimidine-1-yl)-N-[{3,4-dioxo-1-phenyl-7-(2-pyridyloxy)}-2-heptyl]acetamide (NK3201).

In one embodiment, compounds of the invention are administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosemide, bumetanide, butazolamide, chloraminophenamide, clofenamide, clopamide, clorexolone, disulfamide, ethoxzolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and Na⁺ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compounds of the invention may also be administered in combination with an endothelin converting enzyme (ECE) inhibitor, examples of which include, but are not limited to, phosphoramidon, CGS 26303, and combinations thereof.

In a particular embodiment, compounds of the invention are administered in combination with an endothelin receptor antagonist. Representative endothelin receptor antagonists include, but are not limited to: selective endothelin receptor antagonists that affect endothelin A receptors, such as avosentan, ambrisentan, atrasentan, BQ-123, clazosentan, darusentan, sitaxentan, and zibotentan; and dual endothelin receptor antagonists that affect both endothelin A and B receptors, such as bosentan, macitentan, tezosentan).

In yet another embodiment, a compound of the invention is administered in combination with one or more HMG-CoA reductase inhibitors, which are also known as statins. Representative statins include, but are not limited to, atorvastatin, fluvastatin, lovastatin, pitavastatin, pravastatin, rosuvastatin and simvastatin.

In one embodiment, compounds of the invention are administered in combination with a monoamine reuptake inhibitor, examples of which include, by way of illustration and not limitation, norepinephrine reuptake inhibitors such as atomoxetine, buprorion and the buprorion metabolite hydroxybuprorion, maprotiline, reboxetine, and viloxazine; selective serotonin reuptake inhibitors (SSRIs) such as citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline; dual serotonin-norepinephrine reuptake inhibitors (SNRIs) such as bicifadine, duloxetine, milnacipran, nefazodone, and venlafaxine; and combinations thereof.

In another embodiment, compounds of the invention are administered in combination with a muscle relaxant, examples of which include, but are not limited to: carisoprodol, chlorzoxazone, cyclobenzaprine, diflunisal, metaxalone, methocarbamol, and combinations thereof.

In one embodiment, compounds of the invention are administered in combination with a natriuretic peptide or analog, examples of which include but are not limited to: carperitide, CD-NP (Nile Therapeutics), CU-NP, nesiritide, PL-3994 (Palatin Technologies, Inc.), ularitide, cenderitide, and compounds described in Ogawa et al (2004) *J. Biol. Chem.* 279:28625-31. These compounds are also referred to as natriuretic peptide receptor-A (NPR-A) agonists. In another embodiment, compounds of the invention are administered in combination with a natriuretic peptide clearance receptor (NPR-C) antagonist such as SC-46542, cANF (4-23), and AP-811 (Veale (2000) *Bioorg Med Chem Lett* 10:1949-52). For example, AP-811 has shown synergy when combined with the NEP inhibitor, thiorphan (Wegner (1995) *Clin. Exper. Hypert.* 17:861-876).

In another embodiment, compounds of the invention are administered in combination with a neprilysin (NEP) inhibitor. Representative NEP inhibitors include, but are not limited to: AHU-377; candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl)propionamide); SCH-32615 ((S)—N—[N-(1-carboxy-2-phenylethyl)-L-phenylalanyl]-β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino]cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl]cyclopentyl}propionic acid); 5-biphenyl-4-yl-4-(3-carboxypropionylamino)-2-methylpentanoic acid and 5-biphenyl-4-yl-4-(3-carboxypropionylamino)-2-methylpentanoic acid ethyl ester (WO 2007/056546); daglutril [(3S,2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from AHU-377, candoxatril, candoxatrilat, CGS-24128, phosphoramidon, SCH-32615, SCH-34826, SQ-28603, thiorphan, and combinations thereof. In a particular embodiment, the NEP inhibitor is a compound such as daglutril or CGS-26303 ([N-[2-(biphenyl-4-yl)-1(S)-(1H-tetrazol-5-yl)ethyl]amino]methylphosphonic acid), which have activity both as inhibitors of the endothelin converting enzyme (ECE) and of NEP. Other dual acting ECE/NEP compounds can also be used. The NEP inhibitor will be administered in an amount sufficient to provide from about 20-800 mg per day, with typical daily dosages ranging from 50-700 mg per day, more commonly 100-600 or 100-300 mg per day.

In one embodiment, compounds of the invention are administered in combination with a nitric oxide donor, examples of which include, but are not limited to nicorandil; organic nitrates such as pentaerythritol tetranitrate; and sydnonimines such as linsidomine and molsidomine.

In yet another embodiment, compounds of the invention are administered in combination with a non-steroidal anti-inflammatory agent (NSAID). Representative NSAIDs include, but are not limited to: acemetacin, acetyl salicylic acid, alclofenac, alminoprofen, amfenac, amiprilose, aloxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lomoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In one embodiment, compounds of the invention are administered in combination with an N-methyl d-aspartate (NMDA) receptor antagonist, examples of which include, by way of illustration and not limitation, including amantadine, dextromethorphan, dextropropoxyphene, ketamine, ketobemidone, memantine, methadone, and so forth.

In still another embodiment, compounds of the invention are administered in combination with an opioid receptor agonist (also referred to as opioid analgesics). Representative opioid receptor agonists include, but are not limited to: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid receptor agonist is selected from codeine, dihydrocodeine, hydrocodone, hydromorphone, morphine, oxycodone, oxymorphone, tramadol, and combinations thereof.

In a particular embodiment, compounds of the invention are administered in combination with a phosphodiesterase (PDE) inhibitor, particularly a PDE-V inhibitor. Representative PDE-V inhibitors include, but are not limited to, avanafil, lodenafil, mirodenafil, sildenafil (Revatio®), tadalafil (Adcirca®), vardenafil (Levitra®), and udenafil.

In another embodiment, compounds of the invention are administered in combination with a prostaglandin analog (also referred to as prostanoids or prostacyclin analogs). Representative prostaglandin analogs include, but are not limited to, beraprost sodium, bimatoprost, epoprostenol, iloprost, latanoprost, tafluprost, travoprost, and treprostinil, with bimatoprost, latanoprost, and tafluprost being of particular interest.

In yet another embodiment, compounds of the invention are administered in combination with a prostaglandin receptor agonist, examples of which include, but are not limited to, bimatoprost, latanoprost, travoprost, and so forth.

Compounds of the invention may also be administered in combination with a renin inhibitor, examples of which include, but are not limited to, aliskiren, enalkiren, remikiren, and combinations thereof.

In another embodiment, compounds of the invention are administered in combination with a selective serotonin reuptake inhibitor (SSRI). Representative SSRIs include, but are not limited to: citalopram and the citalopram metabolite desmethyl-citalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof.

In one embodiment, compounds of the invention are administered in combination with a $5\text{-HT}_{1D}$ serotonin receptor agonist, examples of which include, by way of illustration and not limitation, triptans such as almotriptan, avitriptan, eletriptan, frovatriptan, naratriptan rizatriptan, sumatriptan, and zolmitriptan.

In one embodiment, compounds of the invention are administered in combination with a sodium channel blocker, examples of which include, by way of illustration and not limitation, carbamazepine, fosphenytoin, lamotrigine, lidocaine, mexiletine, oxcarbazepine, phenytoin, and combinations thereof.

In one embodiment, compounds of the invention are administered in combination with a soluble guanylate cyclase stimulator or activator, examples of which include, but are not limited to ataciguat, riociguat, and combinations thereof.

In one embodiment, compounds of the invention are administered in combination with a tricyclic antidepressant (TCA), examples of which include, by way of illustration and not limitation, amitriptyline, amitriptylinoxide, butriptyline, clomipramine, demexiptiline, desipramine, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, quinupramine, and combinations thereof.

In one embodiment, compounds of the invention are administered in combination with a vasopressin receptor antagonist, examples of which include, by way of illustration and not limitation, conivaptan and tolvaptan.

Combined secondary therapeutic agents may also be helpful in further combination therapy with compounds of the invention. For example, compounds of the invention can be combined with a diuretic and an ARB, or a calcium channel blocker and an ARB, or a diuretic and an ACE inhibitor, or a calcium channel blocker and a statin. Specific examples include, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with the compounds of the invention. Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine.

The following formulations illustrate representative pharmaceutical compositions of the invention.

Exemplary Hard Gelatin Capsules for Oral Administration

A compound of the invention (50 g), 440 g spray-dried lactose and 10 g magnesium stearate are thoroughly blended. The resulting composition is then loaded into hard gelatin capsules (500 mg of composition per capsule). Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Alternately, a compound of the invention (30 g), a secondary agent (20 g), 440 g spray-dried lactose and 10 g magnesium stearate are thoroughly blended, and processed as described above.

Exemplary Gelatin Capsule Formulation for Oral Administration

A compound of the invention (100 mg) is thoroughly blended with polyoxyethylene sorbitan monooleate (50 mg) and starch powder (250 mg). The mixture is then loaded into a gelatin capsule (400 mg of composition per capsule). Alternately, a compound of the invention (70 mg) and a secondary agent (30 mg) are thoroughly blended with polyoxyethylene sorbitan monooleate (50 mg) and starch powder (250 mg), and the resulting mixture loaded into a gelatin capsule (400 mg of composition per capsule).

Alternately, a compound of the invention (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation for Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, a compound of the invention (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the compound of the invention per tablet).

Exemplary Suspension Formulation for Oral Administration

The following ingredients are mixed to form a suspension containing 100 mg of the compound of the invention per 10 mL of suspension:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Liquid Formulation for Oral Administration

A suitable liquid formulation is one with a carboxylic acid-based buffer such as citrate, lactate and maleate buffer solutions. For example, a compound of the invention (which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% NaHCO$_3$ solution, with or without cyclodextrin.

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 m. The micronized composition is then loaded into metered-dose inhaler cartridges containing pressurized 1,1,1,2-tetrafluoroethane in an amount sufficient to provide about 10 µg to about 500 µg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1 N NaOH. The solution is administered using a nebulizer device that provides about 10 µg to about 500 µg of the compound of the invention per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:

AcOH acetic acid
BOC t-butoxycarbonyl (—C(O)OC(CH$_3$)$_3$)
(BOC)$_2$O di-t-butyl dicarbonate
CPME cyclopentyl methyl ether
DCC 1,3-dicyclohexylcarbodiimide
DCM dichloromethane or methylene chloride
DIPEA N,N-diisopropylethylamine
DMAP 4-dimethylaminopyridine
DMF N,N-dimethylformamide
EDC 1-(3-dimethylaminopropyl)-3-ethylcarbodiimide
Et$_3$N triethylamine
EtOAc ethyl acetate
HATU N,N,N',N'-tetramethyl-O-(7-azabenzotriazol-1-yl)uronium hexafluorophosphate
HCTU (2-(6-chloro-1H-benzotriazole-1-yl)-1,1,3,3-tetramethylaminium hexafluorophosphate)
HOBt 1-hydroxybenzotriazole
MeCN acetonitrile
MeOH methanol
MTBE methyl t-butyl ether
Pd(dppf)$_2$Cl$_2$ 1,1-bis(diphenylphosphino)ferrocene palladium chloride
PE petroleum ether
THF tetrahydrofuran Unless noted otherwise, all materials, such as reagents, starting materials and solvents, were purchased from commercial suppliers (such as Sigma-Aldrich, Fluka Riedel-de Haen, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% H$_2$O/2% MeCN/1.0 mL/L TFA; solvent B was 90% MeCN/10% H$_2$O/1.0 mL/L TFA.

Reactions were worked up as described specifically in each preparation for example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers were done by Nuclear Overhauser effect spectroscopy (NOE). Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1:
1-Trityl-1H-1,2,3-triazole-4-carboxylic Acid

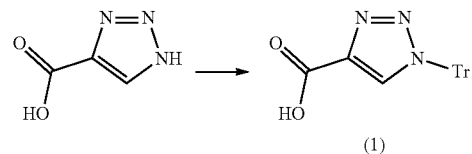

(1)

1H-1,2,3-Triazole-4-carboxylic acid (20.0 g, 177 mmol) was combined with DMF (200 mL, 2.6 mol) and pyridine (100 mL, 1.2 mol), and the resulting mixture was cooled to 0° C. Triphenylmethyl chloride (54 g, 190 mmol) was added in portions and the mixture was stirred at room temperature for 24 hours. The resulting slurry was filtered and the filter cake was washed with water (2×200 mL) and air-dried yield an off white solid (60 g). The solid was slurried in THF (800 mL) at room temperature for 4 hours, then filtered. The filtrate was then concentrated by rotary evaporation, yielding a thick oil. EtOAc (500 mL) was added and the volume was reduced to ~200 mL. The resulting thick slurry was filtered and dried to yield the title compound (35.5 g).

Preparation 2: (2S,4R)-5-Biphenyl-4-yl-4-t-butoxycarbonylamino-2-methyl-2-(tetrahydropyran-2-yloxymethyl)pentanoic Acid

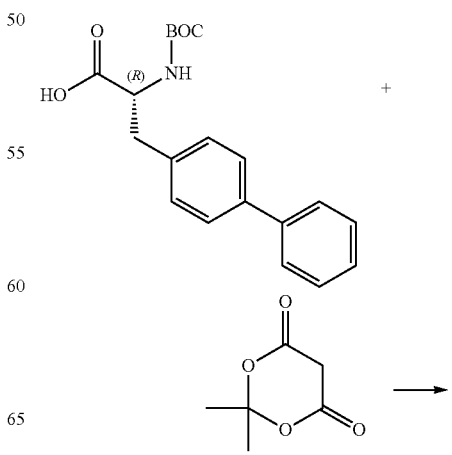

-continued

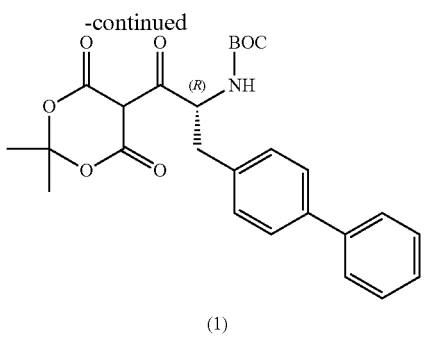

(1)

(R)-3-Biphenyl-4-yl-2-t-butoxycarbonylamino-propionic acid (5.0 g, 15 mmol) and 2,2-dimethyl-1,3-dioxane-4,6-dione (2.3 g, 16.1 mmol) were combined in DMAP (3.2 g, 26.4 mmol). Additional DMAP (2.0 g, 16.1 mmol) and DCM (50 mL) was added and the resulting mixture was stirred and cooled to −5° C. (nitrogen purge) for 30 minutes. EDCI (HCl; (3.1 g, 16.1 mmol) was added in portions, while maintaining the internal temperature below 0° C. with stirring. The mixture was then cooled to −5° C., stirred at that temperature for 3 hours, then left at −20° C. overnight. The mixture was then washed with 0.4 M aqueous KHSO₄ (80 mL) and saturated aqueous NaCl (20 mL), then dried over MgSO₄ overnight. The solids were filtered off and the filtrate was then evaporated to dryness to yield crude Compound 1 (3.2 g).

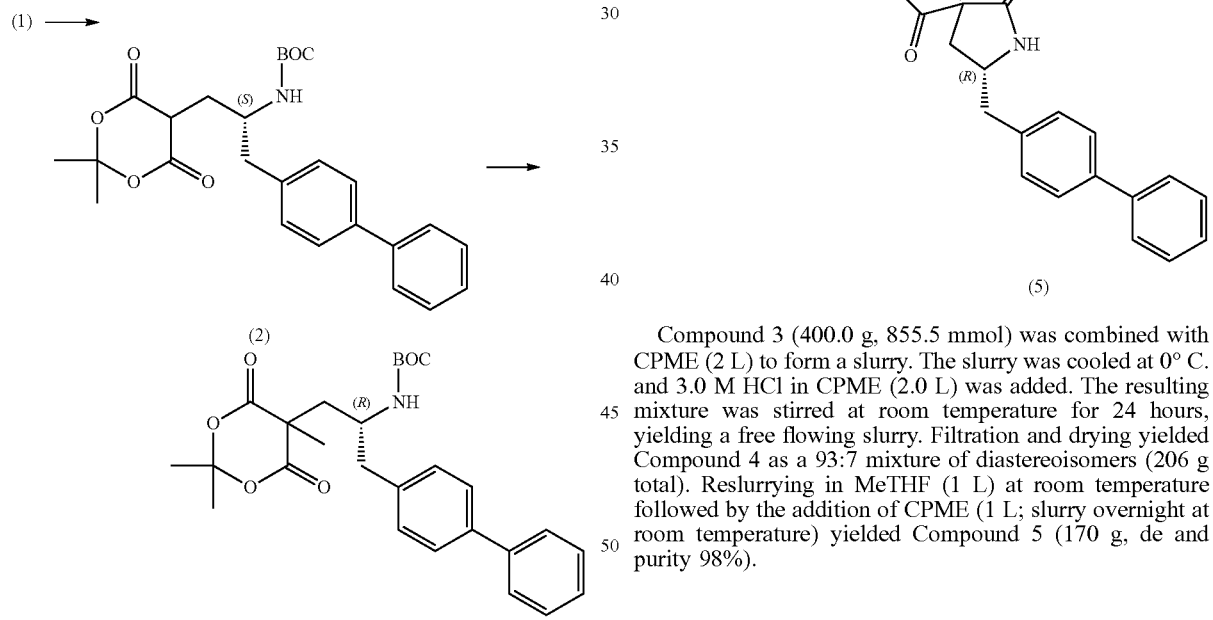

AcOH (8.6 mL) was added to a solution of crude Compound 1 (6.4 g, 14 mmol, 1.0 eq.) in anhydrous MeCN (90 mL) at −5° C. under nitrogen. The mixture was stirred at −5° C. for 30 minutes, then sodium borohydride (1.3 g, 34.5 mmol, 2.5 eq.) was added in small portions over 2 hours. After stirring for another 1 hour at −5° C., saturated aqueous NaCl and 1.7 M of NaCl in water (30 mL) was added. The layers were separated and the organic layer was washed with saturated aqueous NaCl (2×30 mL) and water (2×30 mL), dried under MgSO₄, filtered and evaporated. The resulting crude product was further purified by chromatography (5:1 heptane:EtOAc) to yield Compound 2 (1.1 g, purity 98.4%) as a light yellow solid.

Compound 2 (5.0 g, 11 mmol, 1.0 eq.) and K₂CO₃ (1.8 g, 13.2 mmol, 1.2 eq.) were dissolved in DMF (33.9 mL) and cooled to 0° C. with stirring under nitrogen. Methyl iodide (892 μL, 1.3 eq.) was added and the resulting mixture was stirred at 0° C. for 1 hour. The mixture was allowed to warm to room temperature (23° C.) and held overnight. Saturated aqueous NaCl (35 mL) and EtOAc (35 mL) were added, and the resulting mixture was stirred for 2 minutes. The layers were separated and the organic layer was evaporated. The residue was triturated with EtOAc (20 mL). The solid was filtered off and dried under vacuum. The filtrate was concentrated and triturated again with EtOAc to yield the Compound 3 (3.9 g), [(R)-2-biphenyl-4-yl-1-(2,2,5-trimethyl-4,6-dioxo-[1,3]dioxan-5-ylmethyl)ethyl]carbamic acid t-butyl ester.

Compound 3 (400.0 g, 855.5 mmol) was combined with CPME (2 L) to form a slurry. The slurry was cooled at 0° C. and 3.0 M HCl in CPME (2.0 L) was added. The resulting mixture was stirred at room temperature for 24 hours, yielding a free flowing slurry. Filtration and drying yielded Compound 4 as a 93:7 mixture of diastereoisomers (206 g total). Reslurrying in MeTHF (1 L) at room temperature followed by the addition of CPME (1 L; slurry overnight at room temperature) yielded Compound 5 (170 g, de and purity 98%).

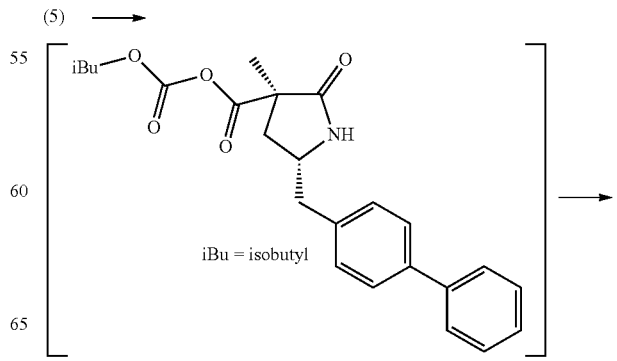

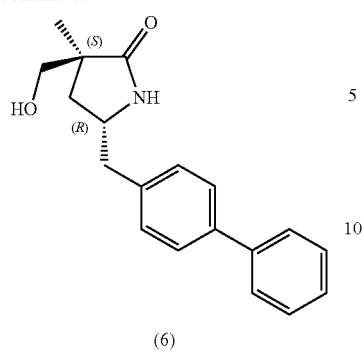

(6)

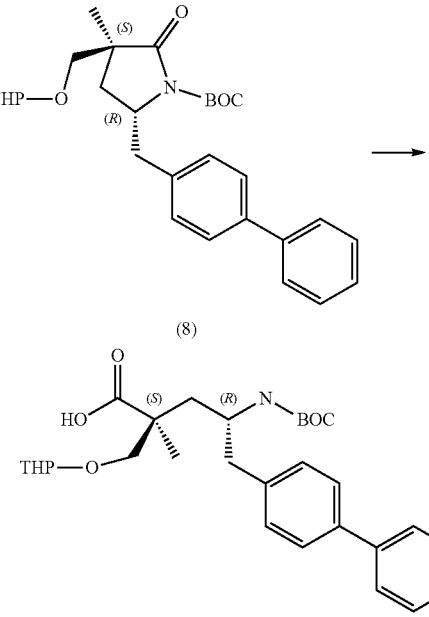

(8)

Compound 5 (25.0 g, 80.8 mmol) was combined with THF (500 mL) and NMM (25 mL, 230 mmol). The resulting mixture was cooled at 0° C. (jacket temp set at −5° C.) and isobutyl chloroformate (21.0 mL, 162 mmol) was added dropwise via addition funnel, while maintaining the internal temperature below 5° C.). The mixture was stirred at 0° C. for 20 minutes. Sodium borohydride (12.2 g, 323 mmol) dissolved in water (40 mL) was added dropwise and the mixture was stirred at 0° C. for 20 minutes (>98% conversion). The reaction was quenched with 1M aqueous HCl (300 mL) and the mixture was stirred at room temperature for 1 hour. Most of solvent was distilled off, leaving a white slurry. The slurry was stirred for 60 minutes and then filtered (small particles, slow filtration) to yield Compound 6 as a white solid (23 g, purity >98%).

Compound 7 (320.0 g, 843.2 mmol) was dissolved in THF (2.5 L) to yield a clear solution, which was purged with nitrogen. The solution was cooled at 0° C. and 1.0 M NaHMDS in THF (920 mL, 920 mmol) was added dropwise over 30 minutes. The mixture was stirred at 0° C. for 15 minutes then di-t-butyldicarbonate (202 g, 926 mmol) dissolved in THF (500 mL) was added dropwise over 1 hour, while maintaining the internal temperature below 5° C. The mixture was allowed to warm to room temperature (>99% conversion to Compound 8). The mixture was cooled to <5° C. followed by the addition of 1.0 M aqueous LiOH (2.5 L, 2.5 mol). The cooling bath was removed and the mixture was stirred overnight at 27° C. (~4% starting material remaining). The mixture was heated at 35° C. for 4 hours (>98% conversion), then cooled to 15° C. The mixture was diluted with EtOAc (3 L) and saturated aqueous NH$_4$Cl (0.37:0.63, NH$_4$Cl:water, 3 L). The phases were separated, and the organic layer was washed with saturated aqueous NH$_4$Cl (3 L) and saturated aqueous NaCl (3 L). The organic layer dried with Na$_2$SO$_4$ (1 kg), followed by solvent removal to yield the crude title compound (463 g) as a glassy sticky solid.

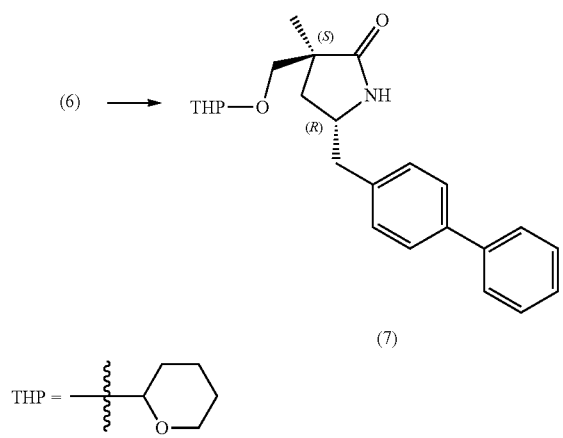

Compound 6 (300 g, 1.0 mol) and DCM (3.8 L) were combined and the resulting mixture was cooled at 0° C. Dihydropyran (185 mL, 2.0 mol) and p-toluenesulfonic acid (52.5 g, 305 mmol) were added and the mixture was stirred at room temperature for 2 hours. Aqueous saturated NaHCO$_3$ (10:90, NaHCO$_3$:water, 3 L) was added and the phases were separated. The organic layer was dried with Na$_2$SO$_4$ followed by solvent removal to approximately 500 mL. Into the crude product was added diisopropyl ether (2 L) and seed crystals. The resulting slurry was stirred overnight at room temperature. Filtration and drying yielded crystalline Compound 7 (320 g, purity >98%).

Preparation 3: (2S,4R)-5-Biphenyl-4-yl-2-methyl-2-(tetrahydropyran-2-yloxymethyl)-4-[(1-trityl-1H-1,2,3-triazole-4-carbonyl)amino]pentanoic Acid

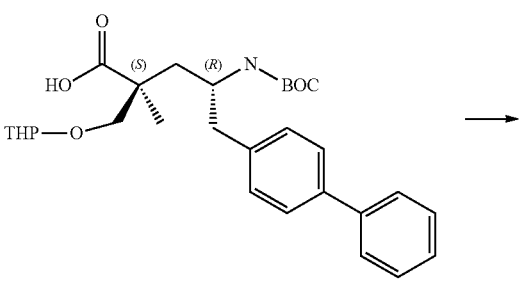

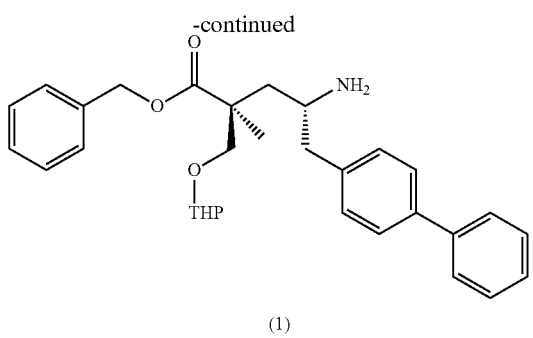

(1)

(2S,4R)-5-Biphenyl-4-yl-4-t-butoxycarbonylamino-2-methyl-2-(tetrahydropyran-2-yloxymethyl)pentanoic acid (10.0 g, 20.1 mmol) was combined with DMF (50 mL, 600 mmol), and stirred. $K_2CO_3$ (3.3 g, 24 mmol) was added and the resulting mixture was cooled to 0° C. Benzyl bromide (3.0 mL, 25 mmol) was added and the mixture was stirred from 0° C. to room temperature, and then overnight. 1.0 M HCl in water (250 mL, 250 mmol) and EtOAc (300 mL, 3.0 mol) were added. The phases were separated and the organic layer was washed with saturated aqueous NaCl (200 mL) and dried over $Na_2SO_4$, followed by solvent removal. DCM (50 mL) and 3.0 M HCl in CPME (100 mL, 300 mmol) were added and the resulting mixture was stirred at room temperature overnight. The volume was reduced by half by rotary evaporation, yielding a free-flowing slurry, which was filtered. The flask and filter cake were washed with CPME (20 mL) and dried. The residue was dissolved in DCM (50 mL, 800 mmol) and resulting suspension was cooled at 0° C. to 10° C. Dihydropyran (3.7 mL, 40.2 mmol) and p-toluenesulfonic acid (692 mg, 4.0 mmol) were added and the resulting mixture was stirred at 0° C. for 2 hours, then stirred overnight at a cool temperature. The volume was reduced to ~20 mL by rotary evaporation. MTBE was added (~30 mL) followed by seed crystals, yielding a thin slurry after 15 minutes of stirring. The volume was reduced by half and additional MTBE (20 mL) was added, while stirring at room temperature to yield a thick slurry. Additional MTBE (to 100 mL volume) was added and the mixture was stirred for 1 hour. Filtration and drying yielded Compound 1 (8.9 g) as an HCl salt.

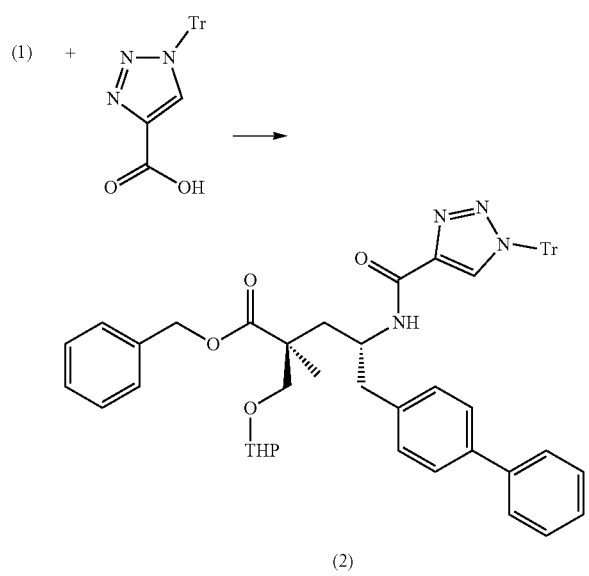

1-Trityl-1H-1,2,3-triazole-4-carboxylic acid (9.2 g, 26 mmol) was dissolved in THF (200 mL, 2.0 mol). DIPEA (9.0 mL, 52 mmol) was added and the resulting mixture was cooled to 0° C. HCTU (11 g, 26 mmol) was added in portions and mixture was stirred at 0° C. for 15 minutes. Compound 1 (HCl salt; 9.0 g, 17 mmol) was added and the resulting mixture was stirred from 0° C. to room temperature. The reaction was monitored and quenched with water (200 mL) after 90 minutes. EtOAc (200 mL) was added. The organic layer was washed with saturated aqueous NaCl (200 mL), dried over $Na_2SO_4$, and the solvent removed. The residue (15 g) was dissolved in DCM (100 mL), the solids were filtered off and the clear solution was purified (300 g SiG column; elution with 10-30% EtOAc in hexanes) to yield Compound 2 (7.5 g).

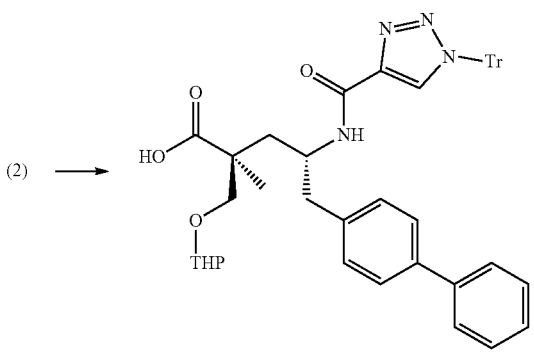

Compound 2 (0.20 g, 0.24 mmol) was combined with EtOAc (3 mL, 30 mmol). $NaHCO_3$ (50 mg, 0.6 mmol) was added and the resulting clear solution was purged with nitrogen. 10% Pd/C (0.05:0.45, Palladium:carbon black, 50 mg, 0.05 mmol) was added and the resulting mixture was purged with hydrogen and then hydrogenated overnight at room temperature. The solids were filtered off and the solvent was removed by rotary evaporation to yield the title compound.

Preparation 4: (2S. 4R)-5-Biphenyl-4-yl-2-methyl-2-(tetrahydropyran-2-yloxymethyl)-4-[(1H-1,2,3-triazole-4-carbonyl)amino]pentanoic Acid

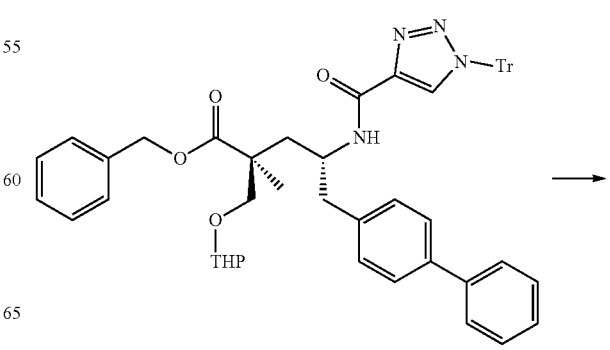

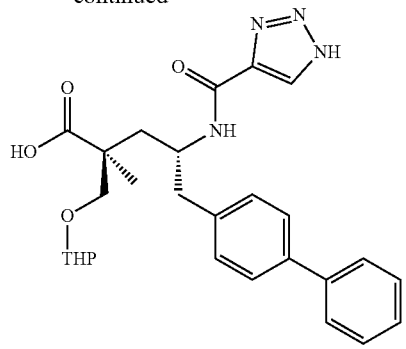

(2S,4R)-5-Biphenyl-4-yl-2-methyl-2-(tetrahydropyran-2-yloxymethyl)-4-[(1-trityl-1H-1,2,3-triazole-4-carbonyl)amino]pentanoic acid benzyl ester (7.5 g, 9.1 mmol) was combined with EtOAc (80 mL, 800 mmol). The resulting clear solution was purged with nitrogen and 10% Pd/C (0.05:0.45, Palladium:carbon black, 1.0 g, 0.94 mmol) was added. The resulting mixture was purged with hydrogen and then hydrogenated overnight at room temperature. The mixture was purged with nitrogen, the solids were filtered off, and the solvent was removed by rotary evaporation to yield the title compound (7 g).

Preparation 5: (R)-3-(4-Bromophenyl)-2-t-butoxycarbonylaminopropionic Acid

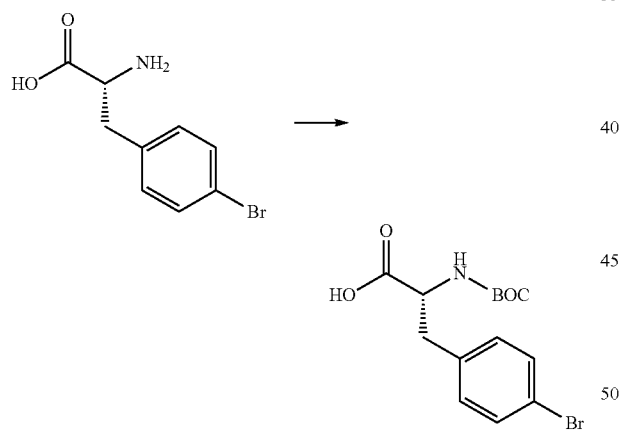

To a solution of (R)-2-amino-3-(4-bromophenyl)propionic acid (50 g, 0.2 mol) in MeCN (700 mL) was added a solution of NaOH (16.4 g, 0.4 mol) in water (700 mL) at −5° C. After stirring for 10 minutes, a solution of (BOC)$_2$O (44.7 g, 0.2 mol) in MeCN (100 mL) was added. The mixture was warmed to room temperature and stirred overnight. After evaporation of the MeCN, the residue was diluted with DCM (800 mL) and acidified with 1 M HCl to pH 2 at −5° C. The aqueous layer was extracted with DCM (3×200 mL). The combined organic layers were washed with saturated aqueous NaCl (500 mL), dried over anhydrous Na$_2$SO$_4$ and concentrated to yield the title compound as a white solid (64.2 g). LC-MS: [M+Na]:366, [2M+Na]:709.

Preparation 6: [(R)-1-(3'-Fluorobiphenyl-4-ylmethyl)-2-(2,2,5-trimethyl-4,6-dioxo-[1,3]dioxan-5-yl)ethyl]carbamic Acid t-Butyl Ester

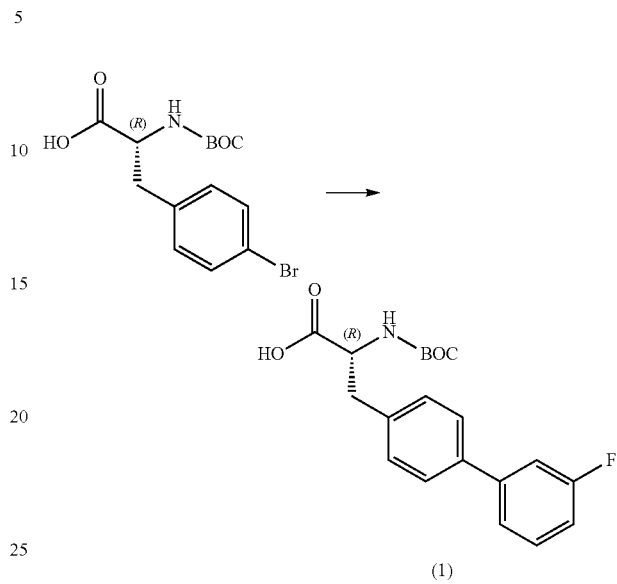

To a solution of (R)-3-(4-bromophenyl)-2-t-butoxycarbonylaminopropionic acid (64.2 g, 187 mmol) in 1,4-dioxane (500 mL) was added 3-fluorophenylboronic acid (31.3 g, 224 mmol) and Pd(dppf)$_2$Cl$_2$ (13.7 g, 19 mmol) at room temperature under nitrogen. After stirring for 10 minutes, a solution of K$_2$CO$_3$ (51.7 g, 374 mmol) in water (250 mL) was added. The mixture was heated to 100° C. and stirred overnight. After evaporation of the solvent, water (200 mL) was added. The aqueous layer was acidified with 1 M HCl to pH 2 and extracted with EtOAc (3×200 mL). The combined organic layers were washed with saturated aqueous NaCl (400 mL), dried over anhydrous Na$_2$SO$_4$, and concentrated to yield the crude product which was further purified by column chromatography (hexanes:EtOAc=4:1) to yield Compound 1 as a light yellow oil (45 g). LC-MS: [M+Na]: 382, [2M+Na]:741.

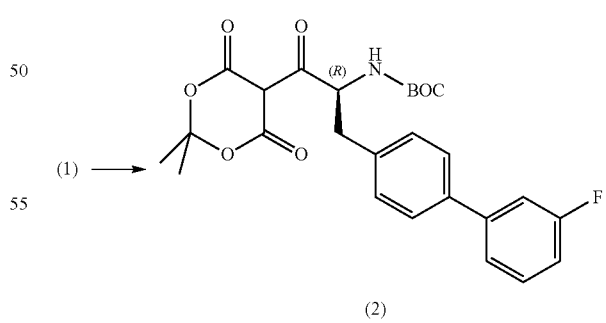

To a solution of Compound 1 (45 g, 125 mmol), Meldrum's acid (23.5 g, 163 mmol), and DMAP (26.0 g, 213 mmol) in anhydrous DCM (500 mL) was added a solution of DCC (33.3 g, 163 mmol) in anhydrous DCM (200 mL) over 1 hour at −5° C. under nitrogen. The mixture was stirred at −5° C. for 8 hours, then refrigerated overnight, during which tiny crystals of dicyclohexylurea precipitated. After filtration, the mixture was washed with 5% KHSO$_4$ (4×200 mL) and saturated aqueous NaCl (1×200 mL), then dried under refrigeration with anhydrous MgSO$_4$ overnight. The solution was evaporated to yield the crude Compound 2 as a light yellow oil (57.7 g). LC-MS: [M+Na]:508, [2M+Na]:993.

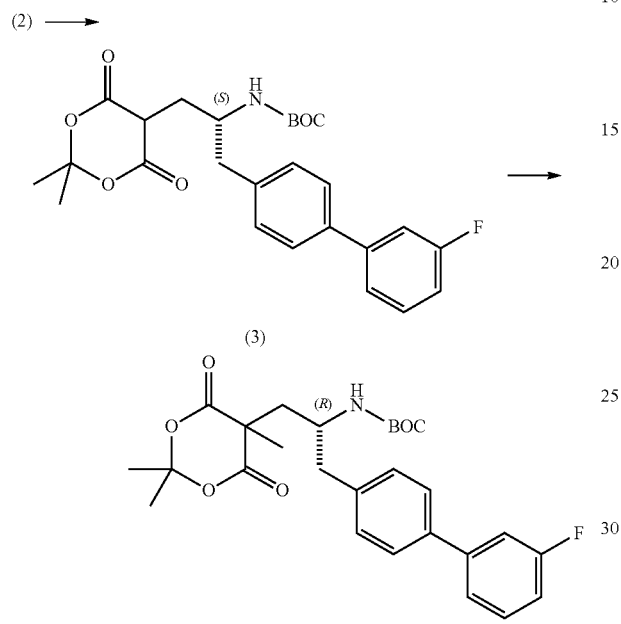

To a solution of Compound 2 (57.7 g, 119 mmol) in anhydrous DCM (1 L) was added AcOH (78.4 g, 1.3 mol) at −5° C. under nitrogen. The mixture was stirred at −5° C. for 0.5 hour, then NaBH$_4$ (11.3 g, 0.3 mol) was added in small portions over 1 hour. After stirring for an additional 1 hour at −5° C., saturated aqueous NaCl (300 mL) was added. The organic layer was washed with saturated aqueous NaCl (2×300 mL) and water (2×300 mL), dried over anhydrous MgSO$_4$, filtered and concentrated to yield the crude product, which was further purified by chromatography (hexanes:EtOAc=6:1) to yield Compound 3 as a light yellow oil (28 g). LC-MS: [M+Na]:494, [2M+Na]:965.

To a solution of Compound 3 (28 g, 60 mmol) in anhydrous DMF (250 mL) was added K$_2$CO$_3$ (9.9 g, 72 mmol) and methyl iodide (25.6 g, 180 mmol) at 0° C. under nitrogen. After stirring for 1 hour at 0° C., the mixture was warmed to room temperature and stirred overnight. The mixture was diluted with water (3 L) and extracted with EtOAc (3×300 mL). The combined organic layers were washed with saturated aqueous NaCl (500 mL), dried over anhydrous Na$_2$SO$_4$, and concentrated to give the crude product which was further purified by chromatography (hexanes:EtOAc=5:1) to yield the title compound as a light yellow solid (11.7 g). LC-MS: [M+Na]=508, [2M+Na]=993. $^1$H NMR (300 MHz, CD$_3$OD): δ7.52-7.49 (m, 2H), 7.41-7.39 (m, 2H), 7.32-7.27 (m, 3H), 7.07-7.01 (m, 1H), 6.21-6.18 (d, 1H), 3.79 (m, 1H), 2.78-2.61 (m, 2H), 2.35-2.20 (m, 2H), 1.76 (s, 6H), 1.59 (s, 3H), 2.21 (s, 1H), 1.28 (s, 9H).

Preparation 7: (2S,4R)-4-t-Butoxycarbonylamino-5-(3'-fluorobiphenyl-4-yl)-2-hydroxymethyl-2-methyl-pentanoic Acid (Compound 1) and (2S,4R)-4-Amino-5-(3'-fluorobiphenyl-4-yl)-2-hydroxymethyl-2-methyl-pentanoic Acid (Compound 2)

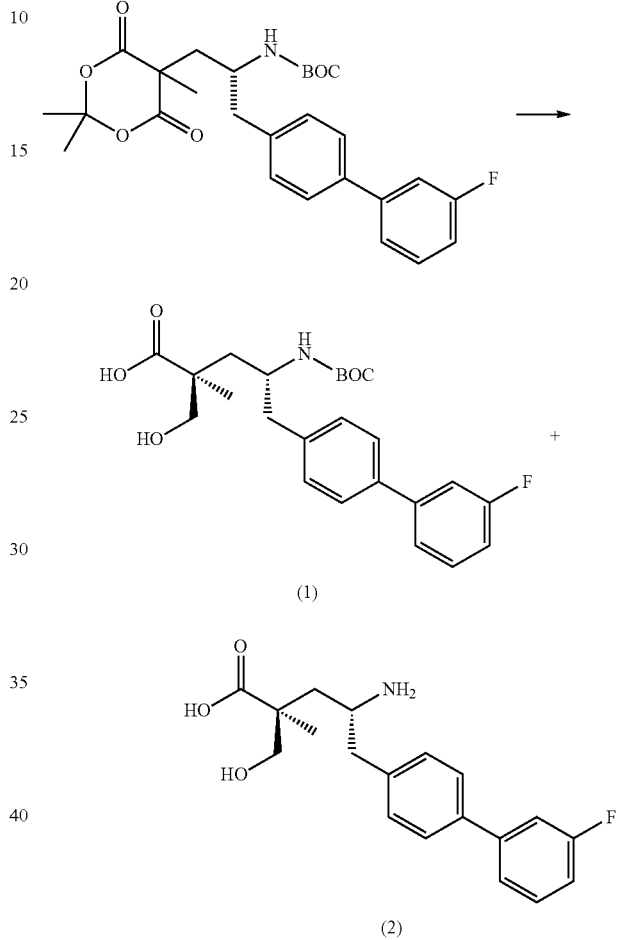

Distilled Water (181 mL) was purged 1 hour under nitrogen, then cannulated into a vessel containing 0.1 M of samarium diiodide in THF (800 mL). While maintaining an atmosphere of nitrogen, a similarly degassed solution of [(R)-1-(3'-fluorobiphenyl-4-ylmethyl)-2-(2,2,5-trimethyl-4,6-dioxo-[1,3]dioxan-5-yl)ethyl]carbamic acid t-butyl ester (4.9 g, 10.0 mmol, 1.0 eq.) and THF (20 mL) was added via canula. The resulting mixture was stirred for 15 minutes, then exposed to air. The solvent was evaporated, and EtOAc (200 mL), saturated aqueous NaCl (50 mL) and 10% citric acid (20 mL) were added. The mixture was stirred for 5 minutes, then both layers were extracted. The organic layer was dried over Na$_2$SO$_4$ and concentrated under vacuum. The crude product was purified by chromatography (330 g gold column, 1:1 ether:EtOAc with 0.5% AcOH) to yield title Compound 1 (1.5 g). A portion of Compound 1 was dissolved in 4M HCl in dioxane (6 mL) and MeCN (10 mL). The solvent was evaporated under vacuum to yield title Compound 2.

Preparation 8: [(R)-1-(4-Bromobenzyl)-2-(2,2,5-trimethyl-4,6-dioxo-[1,3]dioxan-5-yl)ethyl]carbamic Acid t-Butyl Ester

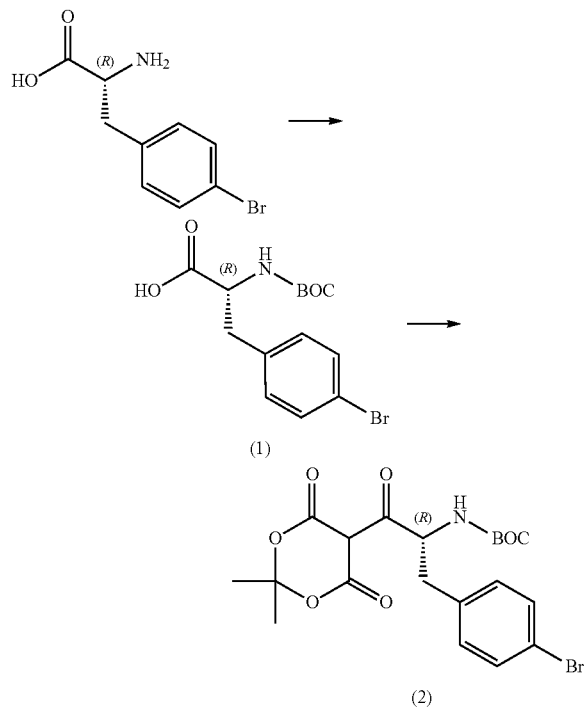

To a mixture of (R)-2-amino-3-(4-bromophenyl)propionic acid (100 g, 410 µmol) in MeCN (600 mL) was added dropwise a solution of NaOH (32.8 g, 820 µmol) in water (800 mL) at 0° C. The resulting solution was stirred for 30 minutes. A solution of (BOC)$_2$O (93.8 g, 430 µmol) in MeCN (200 mL) was added, and the resulting mixture was warmed to room temperature and stirred overnight. The MeCN was evaporated and the residue was diluted with DCM (1 L) and acidified with 2 M HCl to pH=2 at −5° C. The aqueous was extracted and the combined organic layers were washed with saturated aqueous NaCl (500 mL), dried over anhydrous Na$_2$SO$_4$ and concentrated to yield crude Compound 1 (141 g, 100%) as a yellow solid. LC-MS: 366[M+Na]$^+$.

Compound 1 (20 g, 58.1 mmol) was combined with 2,2-dimethyl-1,3-dioxane-4,6-dione (9.2 g, 63.9 mmol), DMAP (10.7 g, 87.2 mmol), and anhydrous DCM (400 mL), and cooled to 0° C. After stirring for 30 minutes, a solution of DCC (13.2 g, 63.9 mmol) in DCM (50 mL) was added dropwise at 0° C. under nitrogen. After the addition, the ice bath was removed and the mixture was stirred at room temperature overnight. The solution was cooled at −20° C. for 1 hour and then the solids were filtered off. The filtrate was washed with a 5% KHSO$_4$ solution (4×100 mL) and saturated aqueous NaCl (200 mL). The organic layer was dried over anhydrous Na$_2$SO$_4$ and evaporated to yield crude Compound 2 (27.5 g) as a gray solid. LC-MS: 492 [M+Na]$^+$.

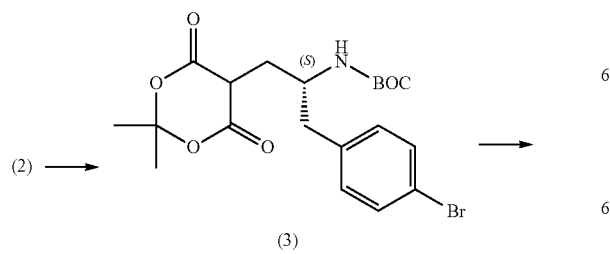

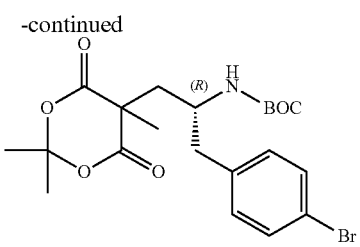

To a solution of Compound 2 (27.5 g, 58.1 mmol) in anhydrous DCM (400 mL) was added AcOH (38.4 g, 639.1 mmol) at −5° C. under nitrogen. The mixture was stirred at −5° C. for 30 minutes. NaBH$_4$ (5.5 g, 145.2 mmol) was added in portions over 30 minutes, and the resulting solution was stirred at room temperature for 3 hours. Saturated aqueous NaCl (300 mL) was added to quench the reaction. The organic layer was washed with saturated aqueous NaCl (2×200 mL), dried over anhydrous Na$_2$SO$_4$ and concentrated to yield crude Compound 3 (22.6 g). LC-MS: 478 [M+Na]$^+$.

To a solution of Compound 3 (22.6 g, 49.6 mmol) and K$_2$CO$_3$ (8.3 g, 59.5 mmol) in anhydrous DMF (160 mL) was added methyl iodide (14 g, 99.2 mmol) dropwise at 0° C. After the addition, the solution was stirred at room temperature overnight. The mixture was evaporated and the residue was dissolved in EtOAc (500 mL) and washed with saturated aqueous NaCl (2×200 mL). The organic solution was dried over anhydrous Na$_2$SO$_4$ and concentrated to yield the crude product which was triturated with ethyl ether (100 mL), then filtered to yield the title compound (14.5 g) as a white solid. LC-MS: 492 [M+Na]$^+$.

Preparation 9: (2S,4R)-4-t-Butoxycarbonylamino-5-(3'-chlorobiphenl-4-yl)-2-hydroxymethyl-2-methyl-pentanoic Acid

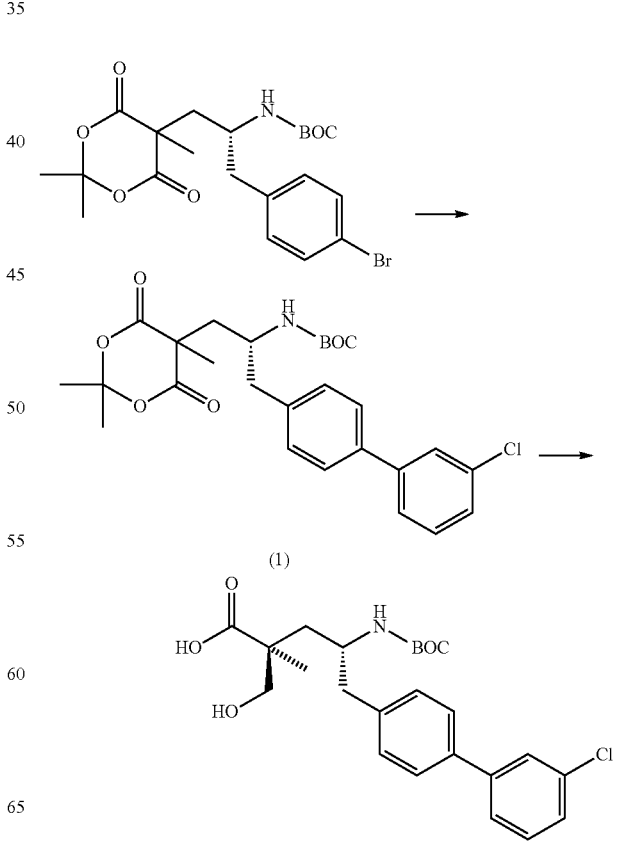

A mixture of [(R)-1-(4-bromobenzyl)-2-(2,2,5-trimethyl-4,6-dioxo-[1,3]dioxan-5-yl)ethyl]carbamic acid t-butyl ester (8 g, 17 mmol), 3-chlorophenylboronic acid (3 g, 18.7 mmol), Pd(dppf)$_2$Cl$_2$ (400 mg, 550 μmol) and potassium fluoride (2 g, 34 mmol) in water (80 mL) and dioxane (80 mL) was stirred at 60° C. under argon for 3 hours. The mixture was concentrated, dispersed in water (150 mL), extracted with EtOAc (2×100 mL), dried over anhydrous Na$_2$SO$_4$ and evaporated to yield the crude product, which was purified by column chromatography (PE:EtOAc=10:1) to yield Compound 1 (7 g) as a white solid. LC-MS: 524 [M+Na]$^+$ Samarium powder (50 g, 330 μmol) was flushed with argon (20 minutes). Anhydrous THF (1.5 L) was added and the resulting suspension was bubbled with argon (15 minutes). Iodine (70 g, 270 mmol) was added and the mixture was flushed again with argon (10 minutes). The mixture was covered with aluminium foil and heated at 65° C. overnight then allowed to cool to room temperature. A solution of Compound 1 (7 g, 13.9 mmol) in THF (200 mL) and water (100 mL) was sealed and flushed with argon (10 minutes), cooled to −70° C., flushed with argon (10 minutes), cooled to −70° C., and flushed with argon (30 minutes). The samarium powder solution (1.5 L) was then added to the cooled solution via cannula, and stirred at room temperature for 2 hours. The solution was evaporated, and the residue was dissolved in EtOAc (200 mL), washed with tartaric acid solution (10%, 150 mL), dried over anhydrous Na$_2$SO$_4$, concentrated and purified by column chromatography (PE: EtOAc=0 to 30%, added with 0.05% AcOH) to yield the title compound (3 g) as a white solid. LC-MS: 470 [M+Na]$^+$. $^1$H NMR (300 MHz, CD3OD): δ 7.28~7.56 (m, 8H), 3.94 (s, 1H), 3.56-3.66 (m, 2H), 2.69-2.82 (m, 2H), 1.70-1.90 (m, 2H), 1.17-1.31 (m, 12H).

Preparation 10: (2S,4R)-4-t-Butoxycarbonylamino-5-(2'-chlorobiphenyl-4-yl)-2-hydroxymethyl-2-methylpentanoic Acid

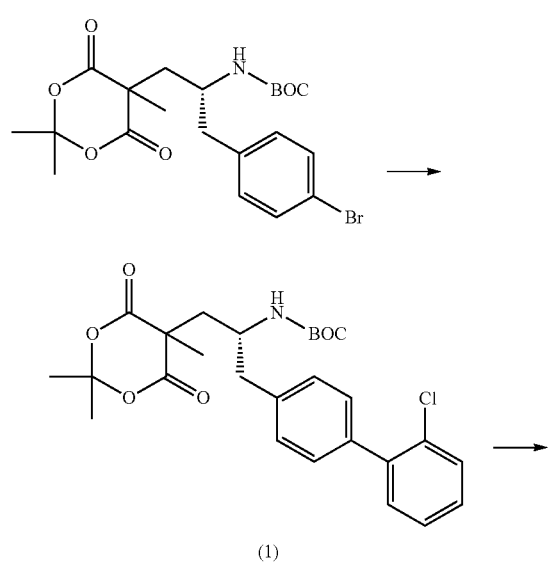

(1)

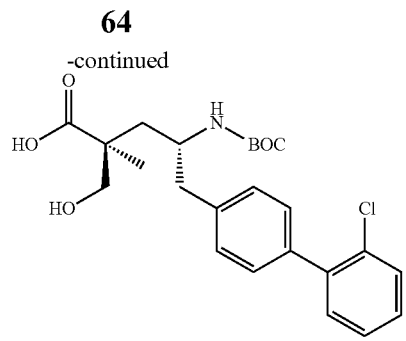

A mixture of [(R)-1-(4-bromobenzyl)-2-(2,2,5-trimethyl-4,6-dioxo-[1,3]dioxan-5-yl)ethyl]carbamic acid t-butyl ester (4.8 g, 30.6 mmol), 2-chlorophenylboronic acid, Pd(dppf)$_2$Cl$_2$ (1.0 g, 1.3 mmol) and potassium fluoride (2.9 g, 51 mmol) in water (50 mL) and dioxane (250 mL) was stirred at 60° C. under argon for 3 hours. The mixture was concentrated, dissolved in water (150 mL), extracted with EtOAc (2×200 mL), dried over anhydrous Na$_2$SO$_4$ and evaporated to yield the crude product, which was purified by column chromatography (PE:EtOAc=3:1) to yield Compound 1 (10 g) as a white solid. LC-MS: 402[M-Boc]$^+$. $^1$H NMR (300 MHz, CDCl$_3$): δ 7.47 (m, 1H), 7.38 (d, J=8.0 Hz, 2H), 7.31 (m, 3H), 7.23 (dd, J=9.9, 5.7 Hz, 2H), 4.18 (d, J=10.2 Hz, 1H), 4.01 (s, 1H), 2.87 (dd, J=13.8, 5.7 Hz, 1H), 2.71 (dd, J=13.7, 6.6 Hz, 1H), 2.30 (m, 2H), 1.75 (s, 6H), 1.65 (s, 3H), 1.33 (d, J=11.7 Hz, 9H).

Samarium powder (50 g, 330 μmol) was flushed with argon (20 minutes). Anhydrous THF (1.5 L) was added and the resulting suspension was bubbled with argon (15 minutes). Iodine (70 g, 270 mmol) was added and the mixture was flushed again with argon (10 minutes). The mixture was covered with aluminium foil and heated at 65° C. overnight then allowed to cool to room temperature. A solution of Compound 1 (7 g, 13.9 mmol) in THF (200 mL) and water (100 mL) was sealed and flushed with argon (10 minutes), cooled to −70° C., flushed with argon (10 minutes), cooled to −70° C., and flushed with argon (30 minutes). The samarium powder solution (1.5 L) was then added to the cooled solution via cannula, and stirred at room temperature for 2 hours. The solution was evaporated, and the residue was dissolved in EtOAc (200 mL), washed with tartaric acid solution (10%, 150 mL), dried over anhydrous Na$_2$SO$_4$, concentrated and purified by column chromatography (PE: EtOAc=0 to 30%, added with 0.05% AcOH) to yield the title compound (2.8 g) as an off-white solid. LC-MS: 348[M-Boc]$^+$. $^1$H NMR (300 MHz, CD$_3$OD): δ 7.46 (m, 1H), 7.28 (m, 7H), 3.97 (s, 1H), 3.63 (m, 2H), 2.82 (m, 1H), 2.69 (m, 1H), 1.89 (m, 1H), 1.74 (m, 1H), 1.33 (m, 7H), 1.22 (m, 5H).

Preparation 11: (2S,4R)-4-t-Butoxycarbonylamino-5-(2'-fluorobiphenyl-4-yl)-2-hydroxymethyl-2-methylpentanoic Acid

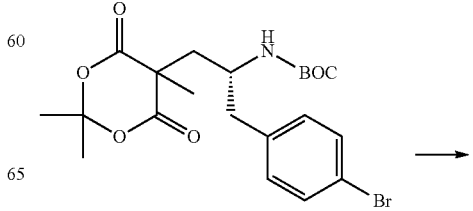

-continued

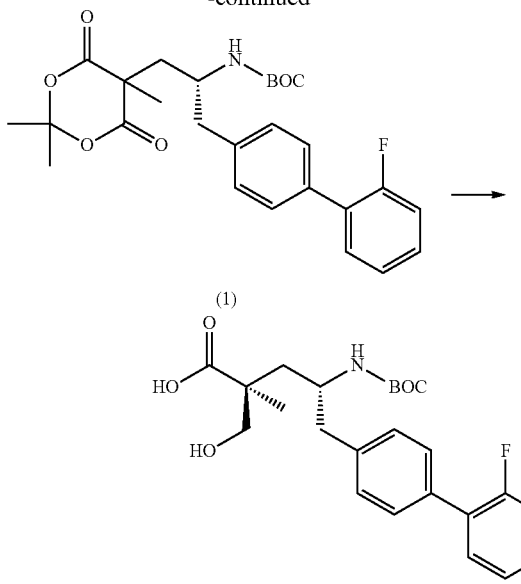

A mixture of [(R)-1-(4-bromobenzyl)-2-(2,2,5-trimethyl-4,6-dioxo-[1,3]dioxan-5-yl)ethyl]carbamic acid t-butyl ester (12 g, 25.6 mmol), 2-fluorophenylboronic acid (4.3 g, 30.7 mmol), Pd(dppf)$_2$Cl$_2$ (950 mg, 1.3 mmol) and potassium fluoride (3.0 g, 51.2 mmol) in water (50 mL) and dioxane (100 mL) was stirred at 60° C. under argon for 2 hours. The mixture was concentrated, diluted with water (100 mL), extracted with EtOAc (3×100 mL), dried over anhydrous Na$_2$SO$_4$ and evaporated to yield the crude product, which was purified by column chromatography (PE:EtOAc=3:1) to yield Compound 1 (10 g). LC-MS: 386.1 [M-Boc]$^+$. $^1$H NMR (300 MHz, CDCl$_3$): δ 7.43 (m, 3H), 7.21 (m, 6H), 4.15 (d, J=10.6 Hz, 1H), 3.99 (s, 1H), 2.83 (m, 1H), 2.70 (dd, J=13.8, 6.8 Hz, 1H), 2.26 (m, 2H), 1.74 (s, 6H), 1.63 (s, 3H), 1.27 (m, 9H).

Samarium powder (50 g, 330 µmol) was flushed with argon (20 minutes). Anhydrous THF (1.5 L) was added and the resulting suspension was bubbled with argon (15 minutes). Iodine (70 g, 270 mmol) was added and the mixture was flushed again with argon (10 minutes). The mixture was covered with aluminium foil and heated at 65° C. overnight then allowed to cool to room temperature. A solution of Compound 1 (7 g, 14.4 mmol) in THF (200 mL) and water (100 mL) was sealed and flushed with argon (10 minutes), cooled to −70° C., flushed with argon (10 minutes), cooled to −70° C., and flushed with argon (30 minutes). The samarium powder solution (1.5 L) was then added to the cooled solution via syringe, and stirred at room temperature for 2 hours. The solution was evaporated, and the residue was dissolved in EtOAc (200 mL), washed with tartaric acid solution (10%, 150 mL), dried over anhydrous Na$_2$SO$_4$, concentrated and purified by column chromatography (PE:EtOAc=0 to 30%, added with 0.05% AcOH) to yield the title compound (2.6 g) as an off-white solid. LC-MS: 332.0[M-Boc]$^+$. $^1$H-NMR (CD$_3$OD, 300 Hz): δ 7.29 (m, 8H), 3.96 (s, 1H), 3.62 (m, 2H), 2.81 (m, 1H), 2.68 (m, 1H), 1.89 (m, 1H), 1.73 (m, 1H), 1.31 (m, 7H), 1.23 (m, 5H).

Preparation 12: (2S,4R)-4-Amino-5-(2'-fluorobiphenyl-4-yl)-2-hydroxymethyl-2-methylpentanoic Acid

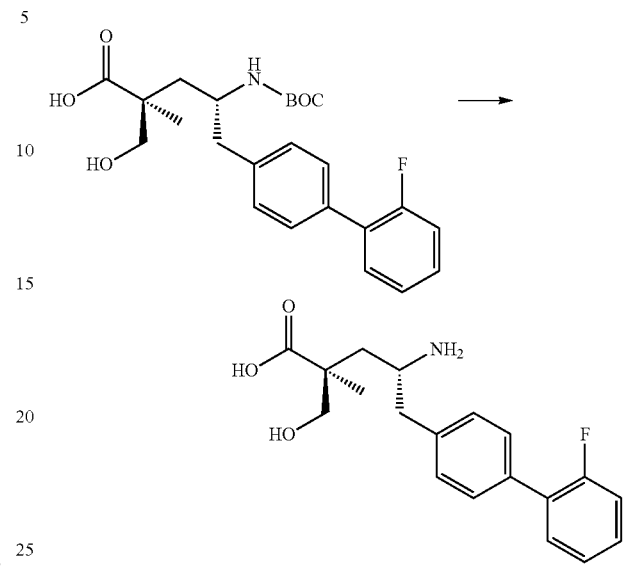

(2S,4R)-4-t-Butoxycarbonylamino-5-(2'-fluorobiphenyl-4-yl)-2-hydroxymethyl-2-methylpentanoic acid (114 mg, 265 µmol) was combined with DIPEA (3 eq.) in DMF (0.2 mL) to yield the title compound.

Preparation 13: (2S,4R)-5-(4-bromophenyl)-4-t-butoxycarbonylamino-2-(hydroxymethyl)-2-methyl-pentanoic Acid

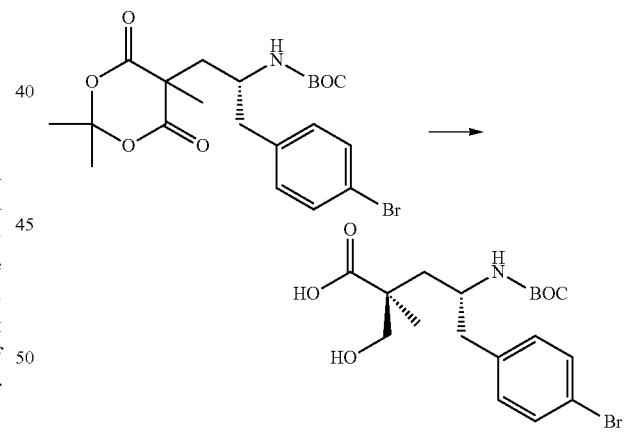

Samarium powder (32 g, 210 mmol) was added to an oven dried flask, and the flask was sealed and flushed with argon for 20 minutes. Anhydrous THF (800 mL) was added and the resulting suspension was bubbled with argon for 15 minutes. Iodine (44.8 g, 176 mmol) was added and the flask flushed again with argon for 10 minutes. The flask was covered and heated at 65° C. overnight, then allowed to cool to room temperature. The resulting SmI$_2$ solution was used directly in the next step.

A solution of [(R)-1-(4-bromobenzyl)-2-(2,2,5-trimethyl-4,6-dioxo-[1,3]dioxan-5-yl)ethyl]carbamic acid t-butyl ester (4 g, 8.5 mmol) in THF (200 mL) and water (100 mL) was sealed and flushed with argon for 10 mins, then cooled to −70° C. and flushed with argon for another 10 minutes, then again cooled to −70° C. and flushed with argon for another 30 minutes. The SmI$_2$ solution (800 mL) was then added and the resulting solution was stirred at room temperature for 2 hours. The solution was evaporated, diluted with EtOAc (200 mL), washed with a tartaric acid solution (10%, 150 mL), dried, concentrated and purified by column chromatography (PE:EA=0 to 30%, added with 0.05% acetic acid) to yield the title compound (1.7 g) as an off-white solid. LC-MS: [M-Boc]+: 316. $^1$H NMR (300 MHz, CD$_3$OD): δ 7.36 (m, 2H), 7.12 (m, 2H), 3.97 (s, 1H), 3.60 (m, 2H), 2.6~2.7 (m, 2H), 1.69-1.81 (m, 2H), 1.15~1.37 (m, 12H).

Preparation 14: (2S,4R)-5-(4-Bromophenyl)-2-hydroxymethyl-2-methyl-4-[(1H-[1,2,3]triazole-4-carbonyl)aminol]pentanoic Acid

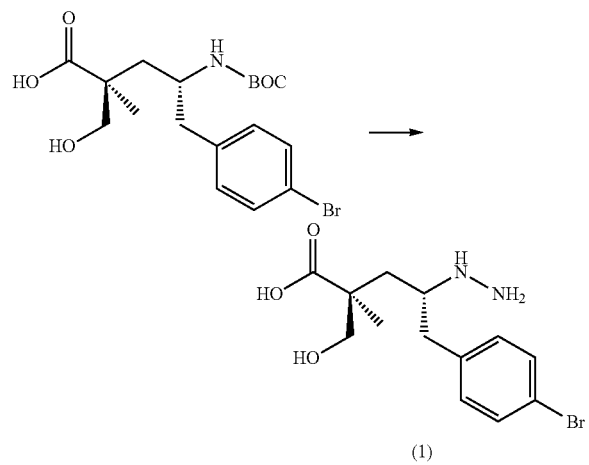

(2S,4R)-5-(4-bromophenyl)-4-t-butoxycarbonylamino)-2-(hydroxymethyl)-2-methylpentanoic acid (1.0 g, 2.4 mmol) was combined with MeCN (20 mL). 4N HCl in dioxane 1.8 mL, 7.2 mmol) was added. The resulting mixture was stirred for 30 minutes then concentrated under reduced pressure.

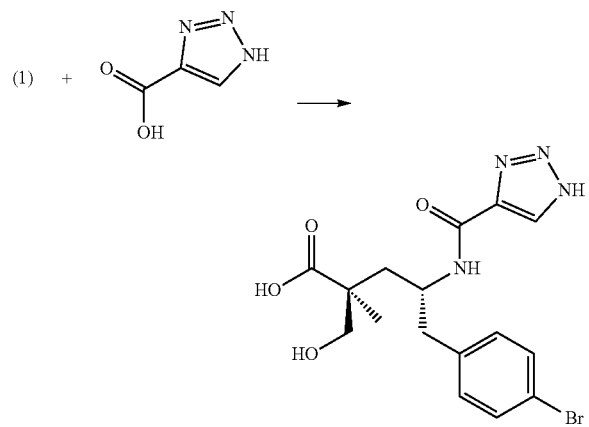

1H-[1,2,3]Triazole-4-carboxylic acid (272 mg, 2.4 mmol) and HATU (959 mg, 2.5 mmol) were combined in DMF (2 mL) and stirred for 10 minutes. DIPEA (1.3 mL, 7.2 mmol) and Compound 1 in DMF (2 mL) were added and the resulting mixture was stirred for 30 minutes then concentrated. The residue was purified by reverse phase chromatography (20-100% MeCN in water) to yield the title compound (287 mg).

Preparation 15: (2S,4R)-4-Amino-5-(5'-chloro-2'-fluorobiphenyl-4-yl)-2-hydroxymethyl-2-methylpentanoic Acid Ethyl Ester (Compound 2) and (2S,4R)-4-t-Butoxycarbonylamino-5-(5'-chloro-2'-fluorobiphenyl-4-yl)-2-hydroxymethyl-2-methylpentanoic Acid Ethyl Ester (Compound 3)

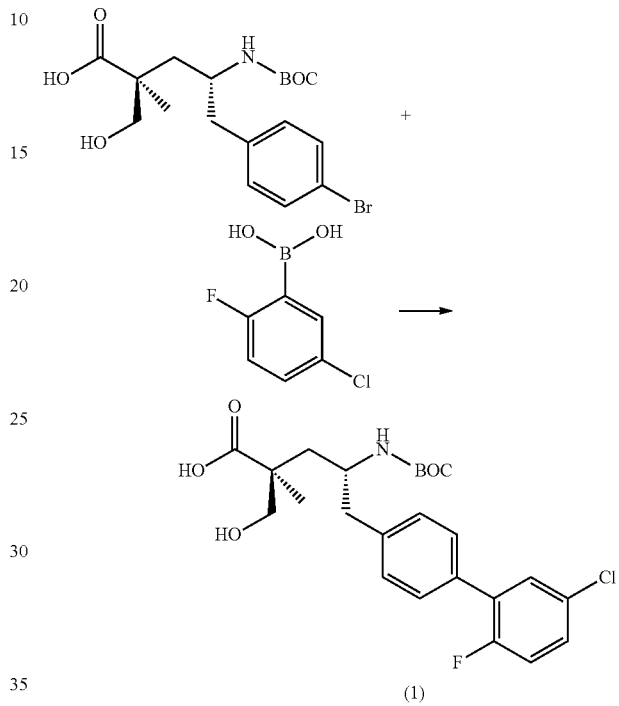

(2S,4R)-5-(4-bromophenyl)-4-((t-butoxycarbonyl)amino)-2-(hydroxymethyl)-2-methylpentanoic acid (1.3 mg, 3.1 mmol) was combined with 5-chloro-2-fluorophenylboronic acid (708 mg, 4.1 mmol), sodium carbonate (993 mg, 9.4 mmol), water (0.2 mL) and dioxane (1.5 mL). The reaction vessel was sealed, air was removed by vacuum, and the vessel was purged with nitrogen. Tetrakis(triphenylphosphine)palladium (0) (541 mg, 468 μmol) was quickly added and air removed by vacuum. The mixture was heated at 90° C. for 45 minutes. The mixture was acidified with 1N HCl/water to pH~4, then extracted with EtOAc. The solvent was removed and the residue was dissolved in AcOH and purified by reverse phase chromatography to yield Compound 1.

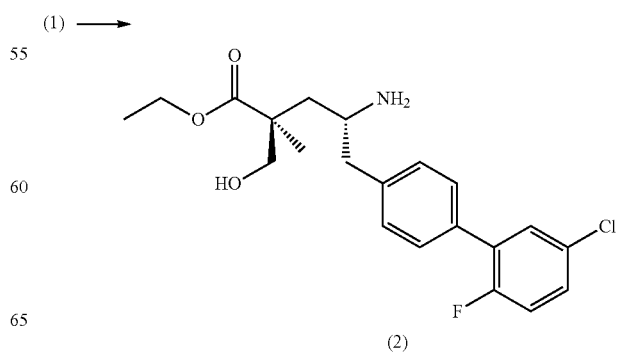

Compound 1 (1.0 g, 2.1 mmol) was dissolved in EtOH (4 mL) and 4N HCl in dioxane (4 mL) and stirred for 3 hours at 60° C. The solvent was evaporated to yield crude Compound 2, which was carried directly to the next step.

(3) →

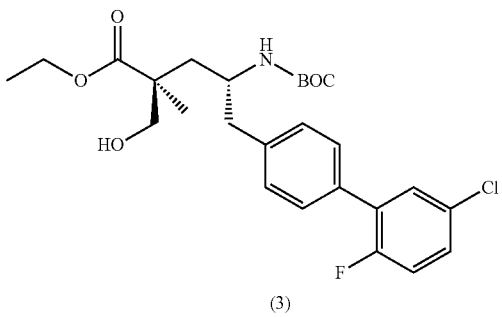

(3)

Compound 2 (800 mg, 2.0 mmol) was dissolved in DCM and (BOC)$_2$O (472 µl, 2.0 mmol), followed by the addition of Et$_3$N (566 µL, 4.1 mmol) and DMAP (1 flake). The resulting mixture was stirred for 3 hours. The solvent was removed and the crude product was triturated with DCM and filtered to yield Compound 3 (800 g), which was used without further purification.

Preparation 16: (2S,4R)-4-Amino-5-(5'-chloro-2'-fluorobiphenyl-4-yl)-2-hydroxymethyl-2-methylpentanoic Acid

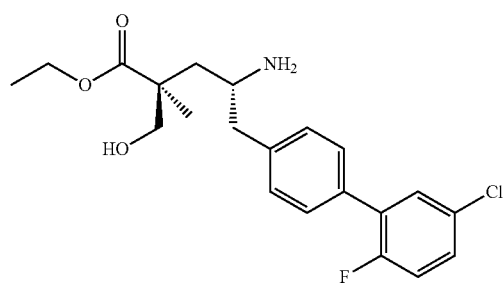

The title compound can be prepared by deprotection of (2S,4R)-4-amino-5-(5'-chloro-2'-fluorobiphenyl-4-yl)-2-hydroxymethyl-2-methylpentanoic acid ethyl ester.

Preparation 17: (2S,4R)-5-Biphenyl-4-yl-4-t-butoxycarbonylamino-2-hdroxymethyl-2-methylpentanoic Acid (P$^2$=BOC) and (2S,4R)-4-Amino-5-biphenyl-4-yl-2-hydroxymethyl-2-methylpentanoic Acid (P$^2$ Removed)

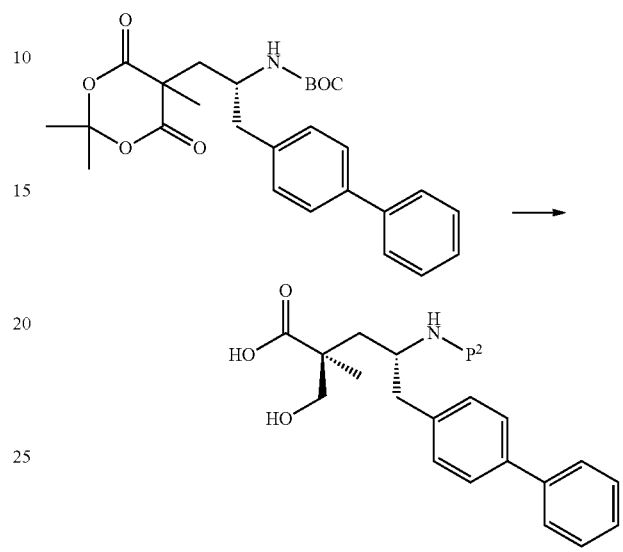

Distilled water (140 mL) was purged 30 minutes under nitrogen, then cannulated into a vessel containing 0.1 M of samarium diiodide in THF (800 mL), exercising caution not to allow any air to come into contact with solution. While maintaining an atmosphere of nitrogen, a degassed solution of [(R)-2-biphenyl-4-yl-1-(2,2,5-trimethyl-4,6-dioxo-1,3-dioxinan-5-ylmethyl)ethyl]carbamic acid t-butyl ester (3.7 g, 8.0 mmol, 1.0 eq.) and THF (100 mL) was added via canula. The resulting mixture was stirred for 15 minutes, then exposed to air. Saturated aqueous NaCl (12 mL), 10% citric acid (6 mL), and EtOAc (30 mL) were added. The mixture was stirred for 5 minutes, then both layers were extracted. The organic layer was dried over Na$_2$SO$_4$ and concentrated under vacuum. The crude product was purified by chromatography (330 g gold column, 50% EtOAc with 0.5% AcOH/ether gradient) to yield the BOC-protected acid (P$^2$=BOC) (1.4 g). The BOC-protected acid was dissolved in MeCN (10 mL), followed by the addition of 4N HCl in dioxane (10 mL). The solvent was evaporated and the product azeotroped with toluene (2×) to yield the acid. (P$^2$ removed) (1.0 g).

Preparation 18: (2S,4R)-4-Amino-5-biphenyl-4-yl-2-methoxymethyl-2-methylpentanoic Acid Ethyl Ester

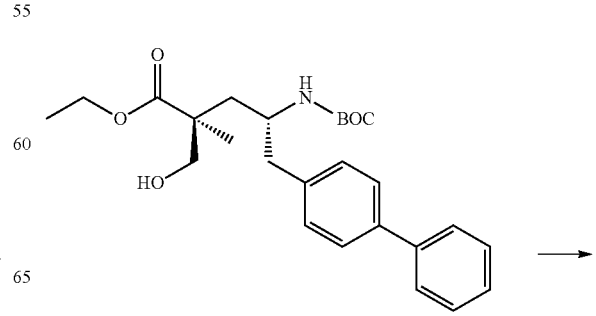

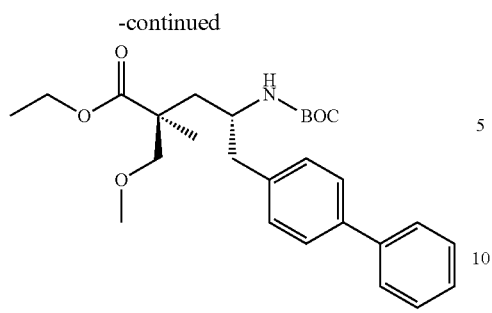

(1)

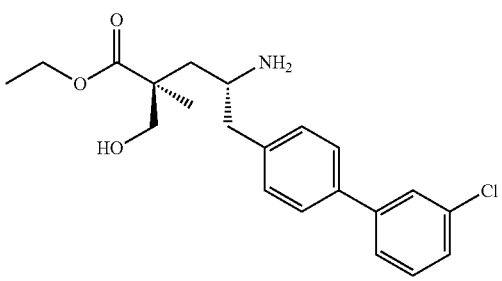

(1)

(2S,4R)-5-Biphenyl-4-yl-4-t-butoxycarbonylamino-2-hydroxymethyl-2-methylpentanoic acid ethyl ester (100 mg, 226 μmol) and tetrabutylammonium hydrogen sulfate (15 mg, 45 μmol) were combined with DCM (1 mL) and NaOH (159 μL, 1.6 mmol). Dimethyl sulfate (114 mg, 906 μmol) was added and the reaction vessel was sealed and stirred vigorously overnight. The mixture was then concentrated under reduced pressure and the residue was dissolved in AcOH and purified by reverse phase chromatography (30-100% MeCN in water) to yield Compound 1 (30 mg).

(2S,4R)-4-t-Butoxycarbonylamino-5-(3'-chlorobiphenyl-4-yl)-2-hydroxymethyl-2-methylpentanoic acid (860 mg, 1.9 mmol) was dissolved in EtOH (4 mL) and 4N HCl in dioxane (4 mL) and stirred for 3 hours at 60° C. The solvent was evaporated and the crude Compound 1 was carried to next step.

(1) ⟶

(1) ⟶

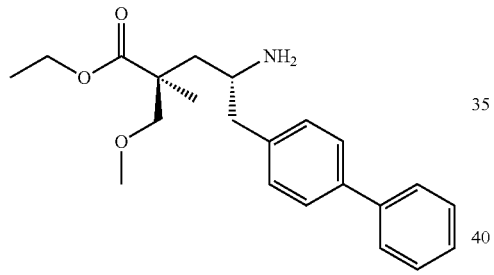

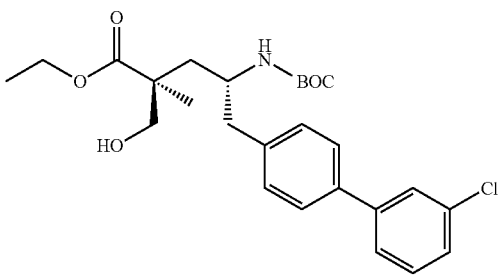

Compound 1 (30 mg, 66 μmol) was combined with MeCN (1 mL) and 4N HCl in dioxane (0.3 mL) and stirred for 10 minutes, then concentrated under reduced pressure to yield the title compound (23 mg).

Compound 1 (722 mg, 1.9 mmol) was dissolved in DCM and (BOC)₂O (446 μL, 1.9 mmol). Et₃N (535 μL, 3.8 mmol) and DMAP (1 flake) were added and the resulting mixture was stirred for 3 hours. The solvent was evaporated and the residue was purified (normal phase chromatography 0-60% EtOAc/hexanes) to yield the title compound (800 mg).

Preparation 19: (2S,4R)-4-t-Butoxycarbonlamino-5-(3'-chlorobiphenyl-4-yl)-2-hydroxymethyl-2-methylpentanoic Acid Ethyl Ester Preparation 20: (2S,4R)-4-Amino-5-(3'-chlorobiphenyl-4-yl)-2-methoxymethyl-2-methylpentanoic Acid Ethyl Ester

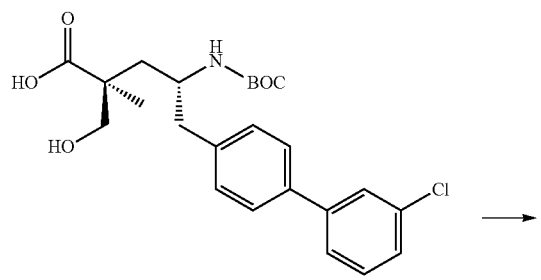

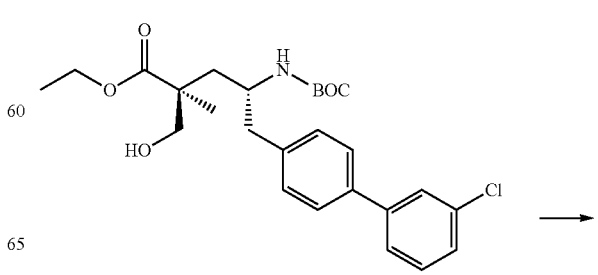

73

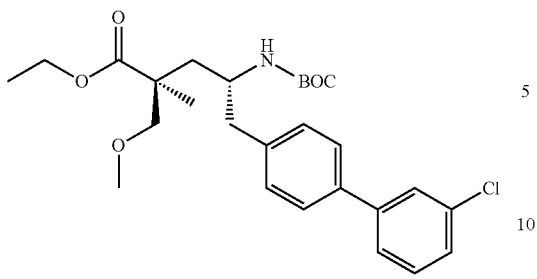

(1)

(2S,4R)-4-t-Butoxy carbonylamino-5-(3'-chlorobiphenyl-4-yl)-2-hydroxymethyl-2-methylpentanoic acid ethyl ester (100 mg, 226 μmol) and tetrabutylammonium hydrogen sulfate (15 mg, 45 μmol) were combined with DCM (1 mL) and NaOH (159 μL, 1.6 mmol). Dimethyl sulfate (114 mg, 906 μmol) was added and the reaction vessel was sealed and stirred vigorously overnight. The mixture was then concentrated under reduced pressure and the residue was dissolved in AcOH and purified by reverse phase chromatography (30-100% MeCN in water) to yield Compound 1 (32 mg).

(1) →

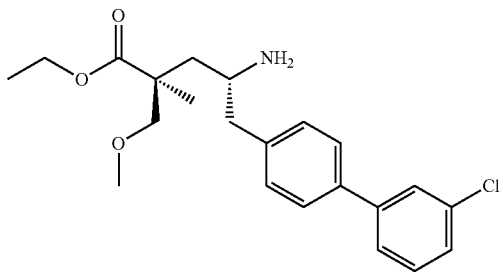

Compound 1 (32 mg, 66 μmol) was combined with MeCN (1 mL) and 4N HCl in dioxane (0.3 mL) and stirred for 10 minutes, then concentrated under reduced pressure to yield the title compound (26 mg).

Preparation 21: (2S,4R)-4-Amino-5-(5'-chloro-2'-fluorobiphenyl-4-yl)-2-methoxymethyl-2-methyl-pentanoic Acid Ethyl Ester

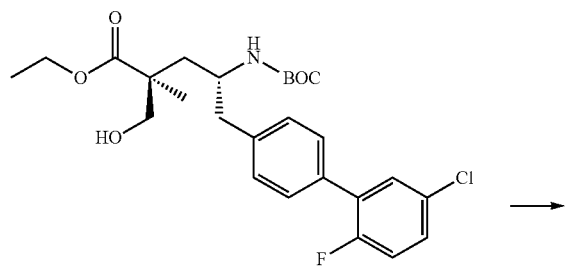

74

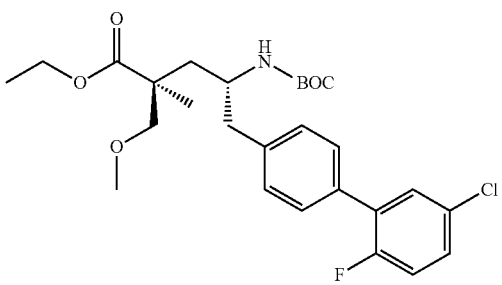

(1)

(2S,4R)-4-t-Butoxycarbonylamino-5-(5'-chloro-2'-fluorobiphenyl-4-yl)-2-hydroxymethyl-2-methyl-pentanoic acid ethyl ester (415 mg, 840 μmol) and tetrabutylammonium hydrogen sulfate (57 mg, 168 μmol) were combined with DCM (1 mL) and NaOH (588 μL, 5.9 mmol). Dimethyl sulfate (424 mg, 3.4 mmol) was added and the reaction vessel was sealed and stirred vigorously overnight. The mixture was extracted with DCM and water, purified (normal phase chromatography; 0-60 EtOAc:hexanes), and concentrated under reduced pressure to yield Compound 1 (220 mg).

(1) →

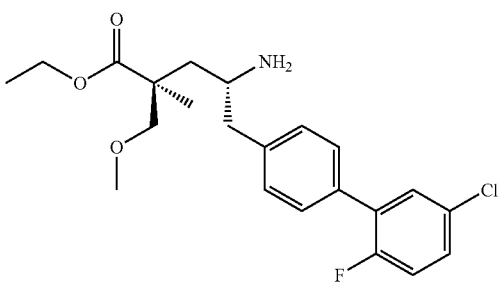

Compound 1 (88 mg, 173 μmol) was combined with MeCN (1 mL) and 4N HCl in dioxane (0.3 mL) and stirred for 10 minutes, then concentrated under reduced pressure to yield the title compound (34 mg).

Preparation 22: (2S,4R)-4-Amino-5-(5'-chloro-2'-fluoro-biphenyl-4-yl)-2-ethoxymethyl-2-methylpentanoic Acid Ethyl Ester

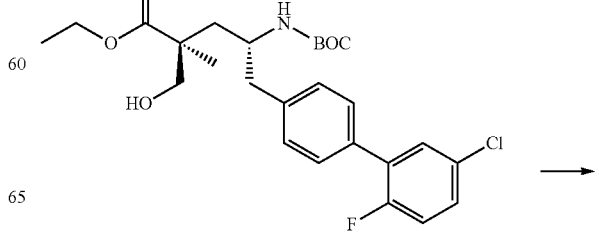

75
-continued

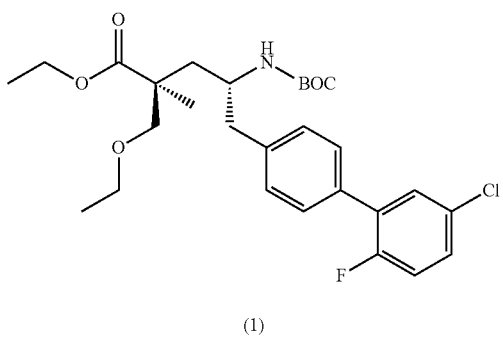

(1)

(2S,4R)-4-t-Butoxycarbonylamino-5-(5'-chloro-2'-fluorobiphenyl-4-yl)-2-hydroxymethyl-2-methyl-pentanoic acid ethyl ester (415 mg, 840 μmol) and tetrabutylammonium hydrogen sulfate (57 mg, 168 μmol) were combined with DCM (1 mL) and NaOH (588 μL, 5.9 mmol). Diethyl sulfate (518 mg, 3.4 mmol) was added and the reaction vessel was sealed and stirred vigorously overnight. The mixture was extracted with DCM and water, purified (normal phase chromatography; 0-60 EtOAc:hexanes), and concentrated under reduced pressure to yield Compound 1 (110 mg).

(1) ⟶

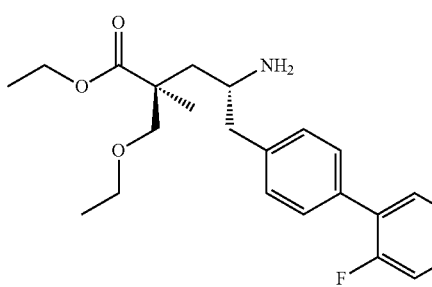

Compound 1 (90 mg, 173 μmol) was combined with MeCN (1 mL) and 4N HCl in dioxane (0.3 mL) and stirred for 10 minutes, then concentrated under reduced pressure to yield the title compound (35.2 mg).

Example 1

It is understood that the compounds of Example 1 can exist in a tautomer form, and that both forms are covered by this example. For example, (2S,4R)-5-biphenyl-4-yl-2-hydroxymethyl-2-methyl-4-[(1H-[1,2,3]triazole-4-carbonyl)-amino]pentanoic acid 5-t-Butyl-2-oxo-[1,3]dioxol-4-ylmethyl ester is depicted in Example 1A but it is understood that this compound can exist in a tautomer form, for example, as (2S,4R)-5-biphenyl-4-yl-2-hydroxymethyl-2-methyl-4-[(3H-[1,2,3]triazole-4-carbonyl)-amino]-pentanoic acid 5-t-butyl-2-oxo-[1,3]dioxol-4-ylmethyl ester. The same is true for the compounds in Examples 1B-1J.

76

1A: (2S,4R)-5-Biphenyl-4-yl-2-hydroxymethyl-2-methyl-4-[(1H-[1,2,3]triazole-4-carbonyl)-amino] pentanoic Acid 5-t-Butyl-2-oxo-[1.3]dioxol-4-ylmethyl Ester

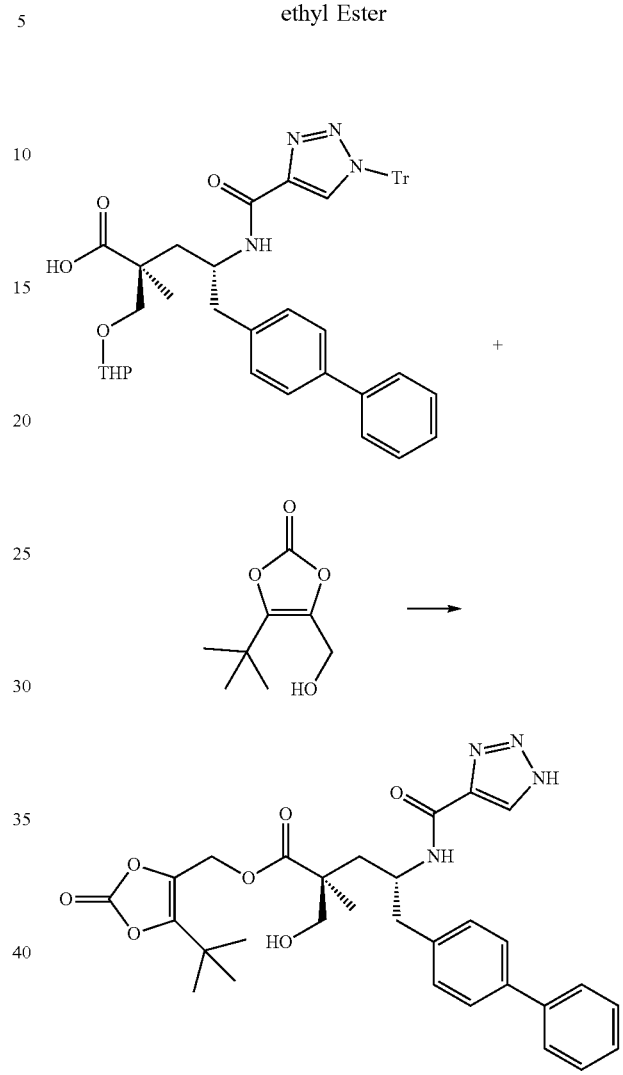

(2S,4R)-5-Biphenyl-4-yl-2-methyl-2-(tetrahydropyran-2-yloxymethyl)-4-[(1-trityl-1H-1,2,3-triazole-4-carbonyl) amino]pentanoic acid (57 mg, 77 μmol) was combined with HOBt (31 mg, 230 μmol) and EDC (41 μL, 230 μmol) in DCM (5 mL) and stirred for 15 minutes. DMF (0.7 mL, 10 mmol) was added and the resulting mixture was stirred for 15 minutes. 4-t-Butyl-5-hydroxymethyl-1,3-dioxol-2-one (40 mg, 230 μmol) and 4-methylmorpholine (34 μL, 0.31 mmol) were added and the mixture was stirred at room temperature overnight. Water was added and the mixture was extracted with EtOAc (20 mL), the organic layer was dried, and the solvent evaporated. The reaction was monitored then quenched (1N HCl in water with MeCN). 1.2M HCl in MeOH (10-20 volumes) was added and the mixture was stirred for 2 hours, then purified by preparative HPLC to yield the title compound (1.6 mg). MS m/z [M+H]+ calc'd for $C_{30}H_{34}N_4O_7$, 563.24; found 563.

77

1B: (2S,4R)-5-Biphenyl-4-yl-2-hydroxymethyl-2-methyl-4-[(1H-[1,2,3]triazole-4-carbonyl)amino]pentanoic Acid 2,2,3,3,3-Pentafluoropropyl Ester

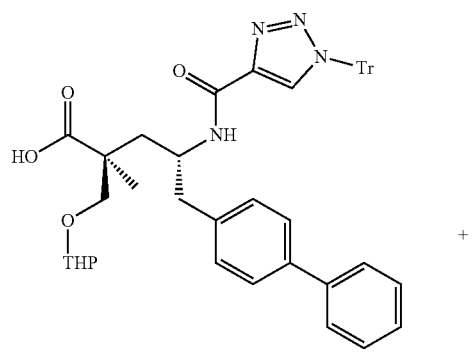

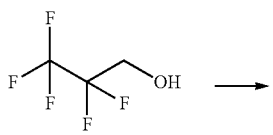

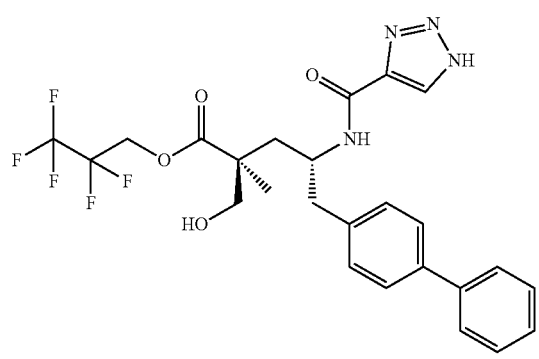

(2S,4R)-5-Biphenyl-4-yl-2-methyl-2-(tetrahydropyran-2-yloxymethyl)-4-[(1-trityl-1H-1,2,3-triazole-4-carbonyl)amino]pentanoic acid (57 mg, 77 μmol) was combined with HOBt (31 mg, 230 μmol) and EDC (41 μL, 230 μmol) in DCM (5 mL) and stirred for 15 minutes. DMF (0.7 mL, 10 mmol) was added and the resulting mixture was stirred for 15 minutes. 2,2,3,3,3-Pentafluoro-1-propanol (23.2 μL, 230 μmol) and 4-methylmorpholine (34 μL, 0.31 mmol) were added and the mixture was stirred at room temperature overnight. Water was added and the mixture was extracted with EtOAc (20 mL), the organic layer was dried, and the solvent evaporated. The reaction was monitored then quenched (1N HCl in water with MeCN). 1.2M HCl in MeOH (10-20 volumes) was added and the mixture was stirred for 2 hours, then purified by preparative HPLC to yield the title compound (1.2 mg). MS m/z [M+H]$^+$ calc'd for $C_{25}H_{25}F_5N_4O_4$, 541.18; found 541.

78

1C: (2S,4R)-5-Biphenyl-4-yl-2-hydroxymethyl-2-methyl-4-[(1H-[1.2.3]triazole-4-carbonyl)-amino]pentanoic Acid 2,2-Difluoropropyl Ester

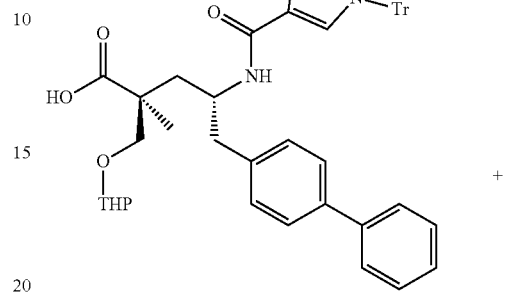

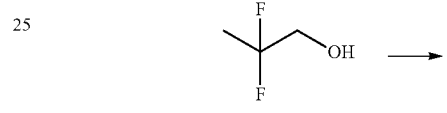

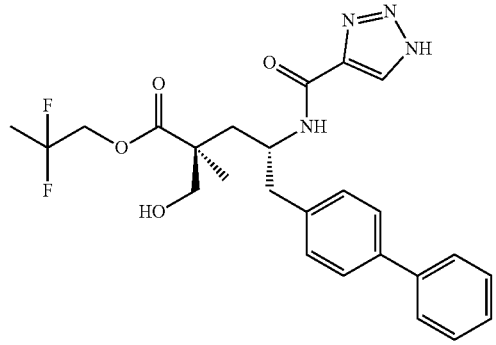

(2S,4R)-5-Biphenyl-4-yl-2-methyl-2-(tetrahydropyran-2-yloxymethyl)-4-[(1-trityl-1H-1,2,3-triazole-4-carbonyl)amino]pentanoic acid (57 mg, 77 μmol) was combined with HOBt (31 mg, 230 μmol) and EDC (41 μL, 230 μmol) in DCM (5 mL) and stirred for 15 minutes. DMF (0.7 mL, 10 mmol) was added and the resulting mixture was stirred for 15 minutes. 2,2-Difluoropropanol (22.3 mg, 230 μmol) and 4-methylmorpholine (34 μL, 0.31 mmol) were added and the mixture was stirred at room temperature overnight. Water was added and the mixture was extracted with EtOAc (20 mL), the organic layer was dried, and the solvent evaporated. The reaction was monitored then quenched (1N HCl in water with MeCN). 1.2M HCl in MeOH (10-20 volumes) was added and the mixture was stirred for 2 hours, then purified by preparative HPLC to yield the title compound (1.4 mg). MS m/z [M+H]$^+$ calc'd for $C_{25}H_{28}F_2N_4O_4$, 487.21; found 487.

1D: (2S,4R)-2-Acetoxymethyl-5-biphenyl-4-yl-2-methyl-4-[(3H-[1,2,3]triazole-4-carbonyl)amino]pentanoic Acid

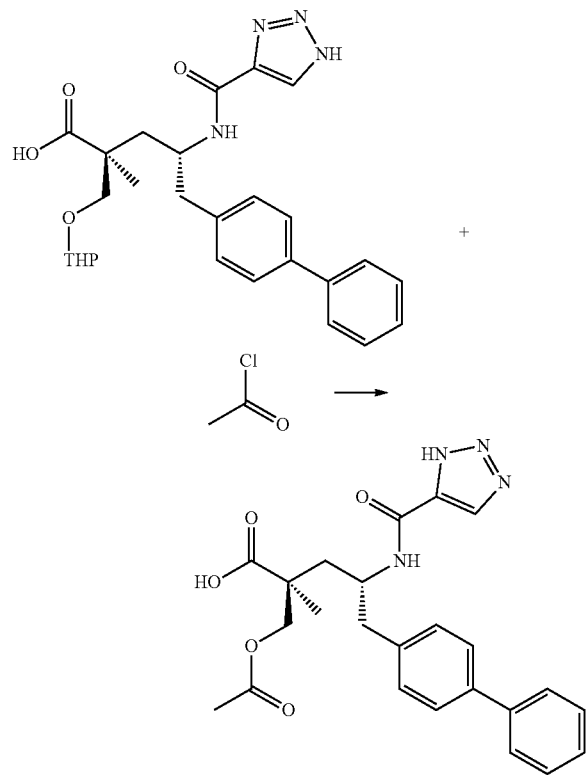

(2S,4R)-5-Biphenyl-4-yl-2-methyl-2-(tetrahydropyran-2-yloxymethyl)-4-[(1H-1,2,3-triazole-4-carbonyl)amino]pentanoic acid (126 mg, 255 µmol) was combined with 4 M HCl in dioxane (191 µL, 765 µmol) in MeCN (0.7 mL, 10 mmol). The mixture was then concentrated under reduced pressure and the residue was purified by reverse phase chromatography. DCM (1 mL, 20 mmol) and acetyl chloride (24 mg, 306 µmol) were added, followed by DIPEA (133 µL, 765 µmol). The resulting mixture was stirred for 10 minutes. The solvent was evaporated and the residue was dissolved in AcOH and purified by preparative HPLC to yield the title compound (5 mg). MS m/z [M+H]$^+$ calc'd for $C_{24}H_{26}N_4O_5$, 451.19; found 451.

1E: (2S,4R)-5-Biphenyl-4-yl-2-isobutyryloxymethyl-2-methyl-4-[(3H-[123]triazole-4-carbonyl)amino]pentanoic Acid

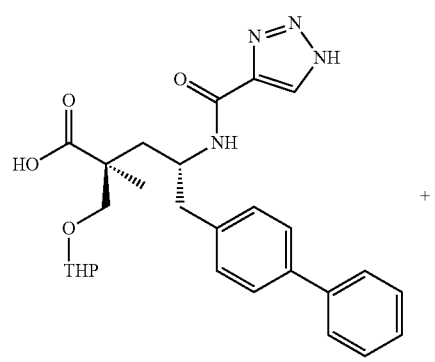

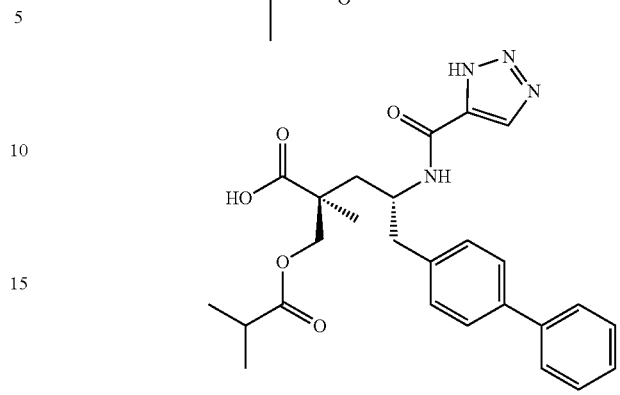

(2S,4R)-5-Biphenyl-4-yl-2-methyl-2-(tetrahydropyran-2-yloxymethyl)-4-[(1H-1,2,3-triazole-4-carbonyl)amino]pentanoic acid (126 mg, 255 µmol) was combined with 4 M HCl in dioxane (191 µL, 765 µmol) in MeCN (0.7 mL, 10 mmol). The mixture was then concentrated under reduced pressure and the residue was purified by reverse phase chromatography. DCM (1 mL, 20 mmol) and isobutyryl chloride (32.6 mg, 306 µmol) were added, followed by DIPEA (133 µL, 765 µmol). The resulting mixture was stirred for 10 minutes. The solvent was evaporated and the residue was dissolved in AcOH and purified by preparative HPLC to yield the title compound (5 mg). MS m/z [M+H]$^+$ calc'd for $C_{26}H_{30}N_4O_5$, 479.22; found 479.

1F: (2S,4R)-5-Biphenyl-4-yl-2-methyl-2-(3-methyl-butyryloxymethyl)-4-[(3H-[1,2,3]triazole-4-carbonyl)amino]pentanoic Acid

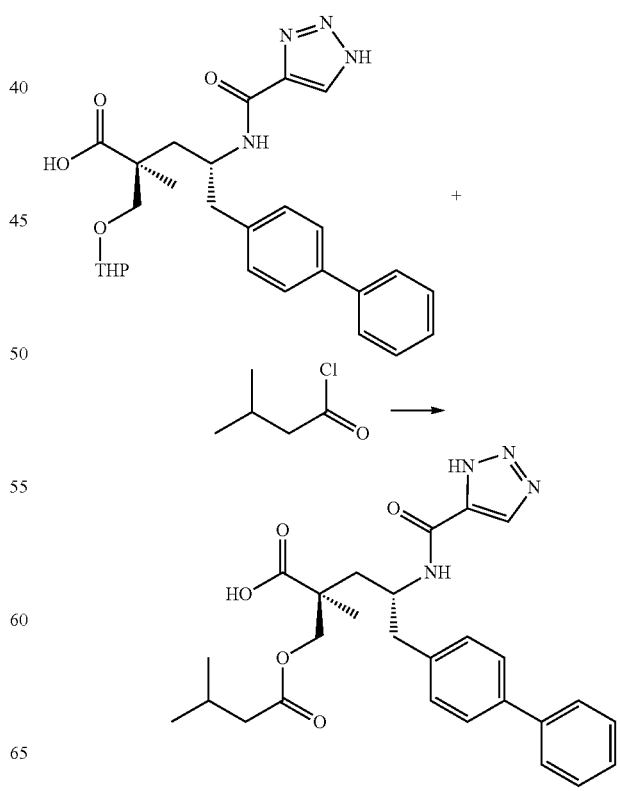

(2S,4R)-5-Biphenyl-4-yl-2-methyl-2-(tetrahydropyran-2-yloxymethyl)-4-[(1H-1,2,3-triazole-4-carbonyl)amino]pentanoic acid (126 mg, 255 µmol) was combined with 4 M HCl in dioxane (191 µL, 765 µmol) in MeCN (0.7 mL, 10 mmol). The mixture was then concentrated under reduced pressure and the residue was purified by reverse phase chromatography. DCM (1 mL, 20 mmol) and isovaleryl chloride (39.9 mg, 306 µmol) were added, followed by DIPEA (133 µL, 765 µmol). The resulting mixture was stirred for 10 minutes. The solvent was evaporated and the residue was dissolved in AcOH and purified by preparative HPLC to yield the title compound (3 mg). MS m/z [M+H]$^+$ calc'd for $C_{27}H_{32}N_4O_5$, 493.24; found 493.

1G: (2S,4R)-5-Biphenyl-4-yl-2-hydroxymethyl-2-methyl-4-[(1H-[1,2,3]triazole-4-carbonyl)amino]pentanoic Acid Hexyl Ester 1H: (2S,4R)-5-Biphenyl-4-yl-2-hydroxymethyl-2-methyl-4-[(1H-[1,2,3]triazole-4-carbonyl)amino]pentanoic Acid Heptyl Ester

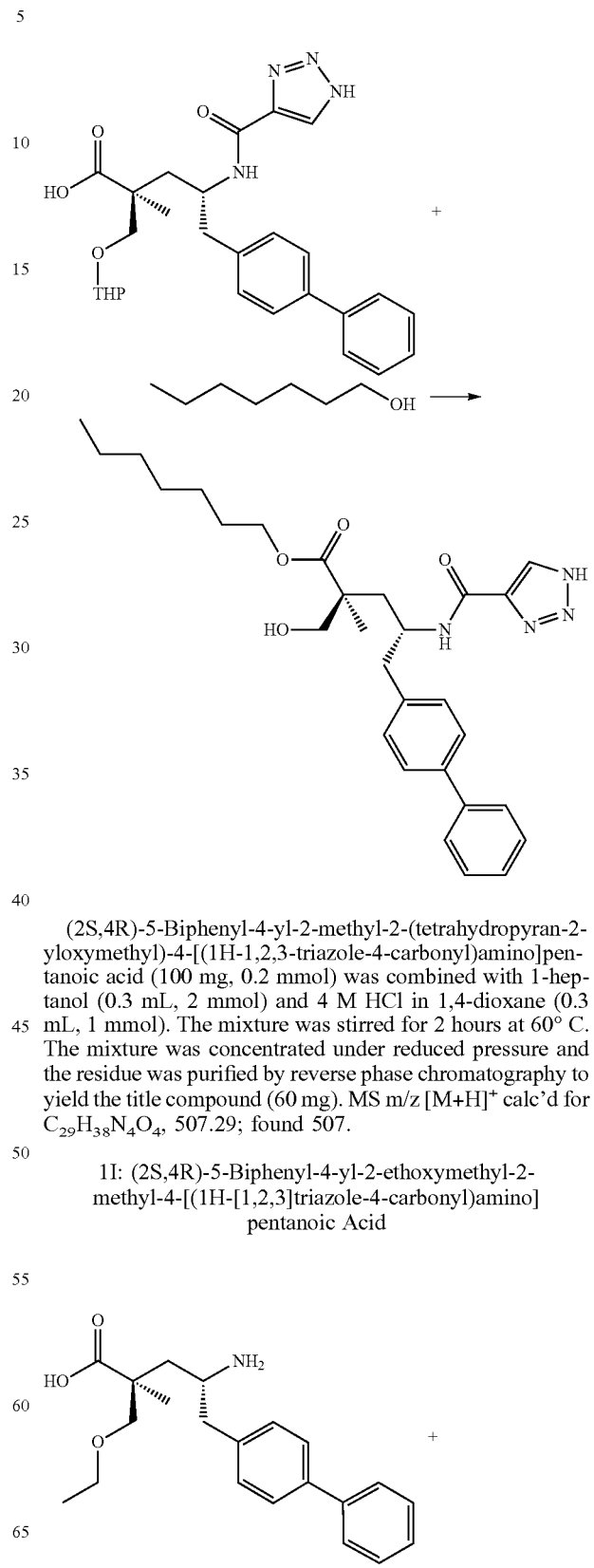

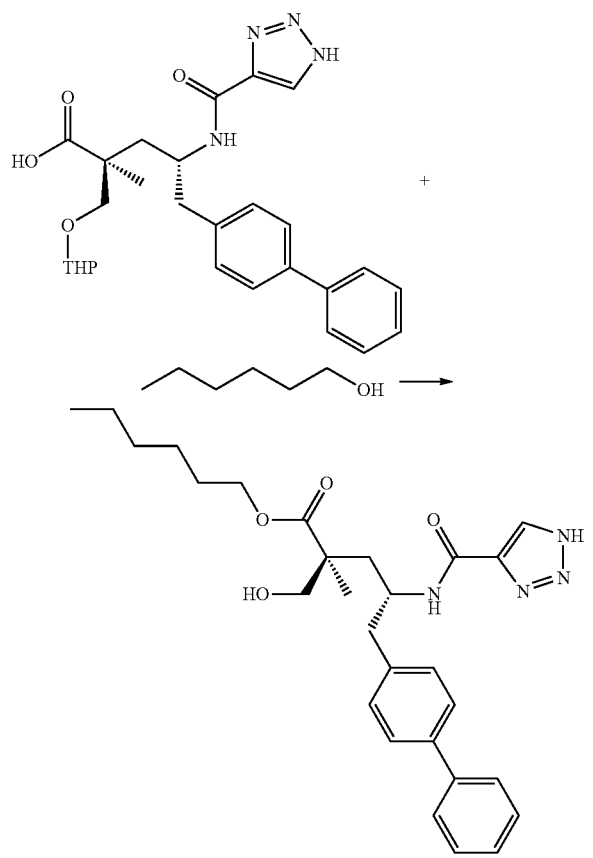

(2S,4R)-5-Biphenyl-4-yl-2-methyl-2-(tetrahydropyran-2-yloxymethyl)-4-[(1H-1,2,3-triazole-4-carbonyl)amino]pentanoic acid (100 mg, 0.2 mmol) was combined with 1-hexanol (0.3 mL, 2 mmol) and 4 M HCl in 1,4-dioxane (0.3 mL, 1 mmol). The mixture was stirred for 2 hours at 60° C. The mixture was concentrated under reduced pressure and the residue was purified by reverse phase chromatography to yield the title compound (51 mg). MS m/z [M+H]$^+$ calc'd for $C_{28}H_{36}N_4O_4$, 493.27; found 493.

(2S,4R)-5-Biphenyl-4-yl-2-methyl-2-(tetrahydropyran-2-yloxymethyl)-4-[(1H-1,2,3-triazole-4-carbonyl)amino]pentanoic acid (100 mg, 0.2 mmol) was combined with 1-heptanol (0.3 mL, 2 mmol) and 4 M HCl in 1,4-dioxane (0.3 mL, 1 mmol). The mixture was stirred for 2 hours at 60° C. The mixture was concentrated under reduced pressure and the residue was purified by reverse phase chromatography to yield the title compound (60 mg). MS m/z [M+H]$^+$ calc'd for $C_{29}H_{38}N_4O_4$, 507.29; found 507.

1I: (2S,4R)-5-Biphenyl-4-yl-2-ethoxymethyl-2-methyl-4-[(1H-[1,2,3]triazole-4-carbonyl)amino]pentanoic Acid

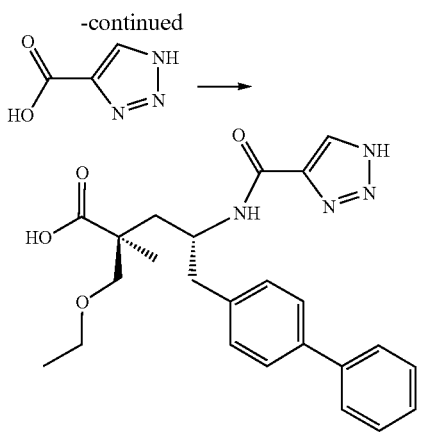

1H-[1,2,3]Triazole-4-carboxylic acid and (2S,4R)-4-amino-5-biphenyl-4-yl-2-ethoxymethyl-2-methylpentanoic acid were reacted as described herein to yield the title compound (0.8 mg). MS m/z [M+H]+ calc'd for $C_{24}H_{28}N_4O_4$, 437.21; found 437.2.

1J: (2S,4R)-5-Biphenyl-4-yl-2-methoxymethyl-2-methyl-4-[(1H-[1,2,3]triazole-4-carbonyl)amino]pentanoic Acid

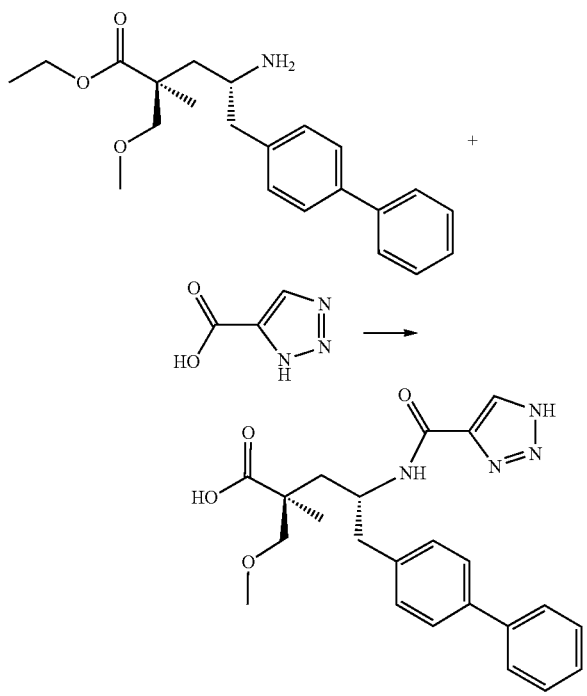

3H-[1,2,3]Triazole-4-carboxylic acid (3.5 mg, 31 μmol) and HATU (12 mg, 31 μmol) were combined in DMF (0.5 mL) and stirred for 5 minutes. A solution of (2S,4R)-4-amino-5-biphenyl-4-yl-2-methoxymethyl-2-methylpentanoic acid ethyl ester (11 mg, 31 μmol) and DIPEA (16 μL, 93 μmol) in DMF (0.5 mL) was added and the resulting mixture was stirred for 20 minutes then concentrated under reduced pressure.

The residue was combined with THF (0.6 mL) and NaOH (124 μL, 124 μmol) and stirred at 60° C. for 2 hours, then concentrated under reduced pressure. The residue was dissolved in AcOH and compounds was purified by preparative HPLC to yield the title compound (1 mg). MS m/z [M+H]+ calc'd for $C_{23}H_{26}N_4O_4$, 423.20; found 423.2.

Example 2

It is understood that the compounds of Example 2 can exist in a tautomer form, and that both forms are covered by this example. For example, (2S,4R)-2-hydroxymethyl-5-(2'-methoxybiphenyl-4-yl)-2-methyl-4-[(1H-[1,2,3]triazole-4-carbonyl)amino]pentanoic acid is depicted in Example 2A but it is understood that this compound can exist in a tautomer form, for example, as (2S,4R)-2-hydroxymethyl-5-(2'-methoxybiphenyl-4-yl)-2-methyl-4-[(3H-[1,2,3]triazole-4-carbonyl)amino]pentanoic acid. The same is true for the compounds in Examples 2B-2S.

2A: (2S,4R)-2-Hydroxymethyl-5-(2'-methoxybiphenyl-4-yl)-2-methyl-4-[(1H-[1,2,3]triazole-4-carbonyl)amino]pentanoic Acid

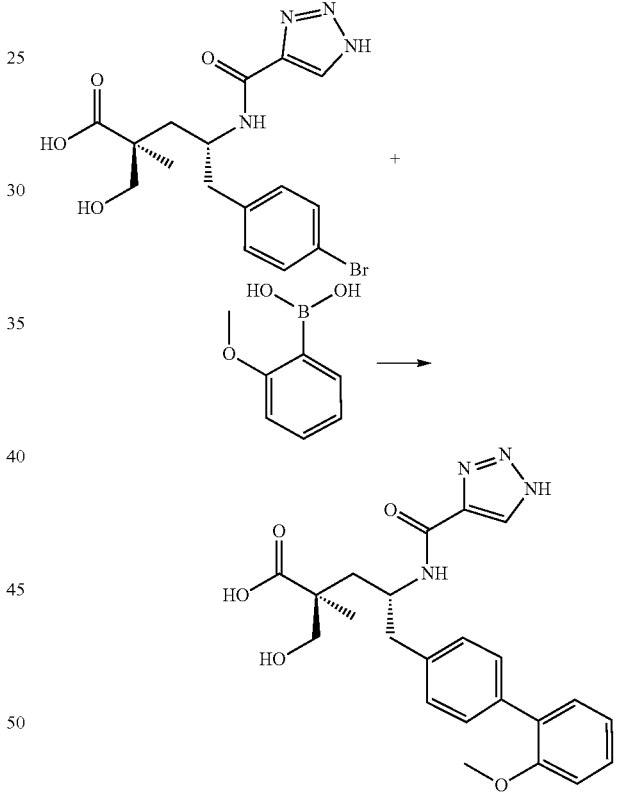

(2S,4R)-5-(4-bromophenyl)-2-hydroxymethyl-2-methyl-4-[(1H-[1,2,3]triazole-4-carbonyl)amino]pentanoic acid (38 mg, 92 μmol) was combined with 2-methoxyphenylboronic acid (28.1 mg, 185 μmol), sodium carbonate (29.4 mg, 277 μmol), water (0.2 mL) and dioxane (1.5 mL). The reaction vessel was sealed, air was removed by vacuum, and the vessel was purged with nitrogen. Tetrakis(triphenylphosphine)palladium (0) (21.4 mg, 18 μmol) was quickly added and air was removed by vacuum. The mixture was heated at 90° C. for 45 minutes. The mixture was acidified to pH~3 and filtered, and the solvate was concentrated. The residue was dissolved in AcOH (0.7 mL) and purified by preparative HPLC to yield the title compound (12.5 mg). MS m/z [M+H]+ calc'd for $C_{23}H_{26}N_4O_5$, 439.19; found 439.2.

85

2B: (2S,4R)-5-(2'-Chlorobiphenyl-4-yl)-2-hydroxymethyl-2-methyl-4-[(1H-[1,2,3]triazole-4-carbonyl)amino]pentanoic Acid

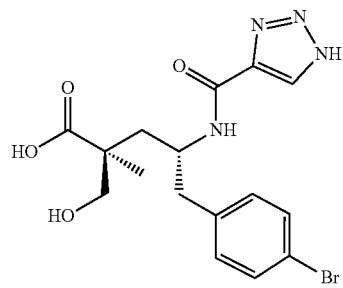

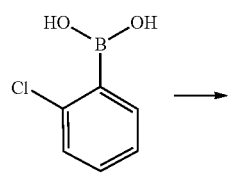

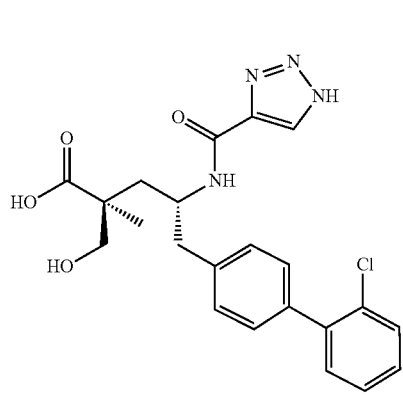

(2S,4R)-5-(4-bromophenyl)-2-hydroxymethyl-2-methyl-4-[(1H-[1,2,3]triazole-4-carbonyl)amino]pentanoic acid (38 mg, 92 μmol) was combined with 2-chlorophenylboronic acid (28.9 mg, 185 μmol), sodium carbonate (29.4 mg, 277 μmol), water (0.2 mL) and dioxane (1.5 mL). The reaction vessel was sealed, air was removed by vacuum, and the vessel was purged with nitrogen. Tetrakis(triphenylphosphine)palladium (0) (21.4 mg, 18 μmol) was quickly added and air was removed by vacuum. The mixture was heated at 90° C. for 45 minutes. The mixture was acidified to pH~3 and filtered, and the solvate was concentrated. The residue was dissolved in AcOH (0.7 mL) and purified by preparative HPLC to yield the title compound (18.2 mg). MS m/z [M+H]+ calc'd for $C_{22}H_{23}ClN_4O_4$, 443.14; found 443.2.

86

2C: (2S,4R)-2-Hydroxymethyl-2-methyl-5-(2'-methylbiphenyl-4-yl)-4-[(1H-[1,2,3]triazole-4-carbonyl)amino]pentanoic Acid

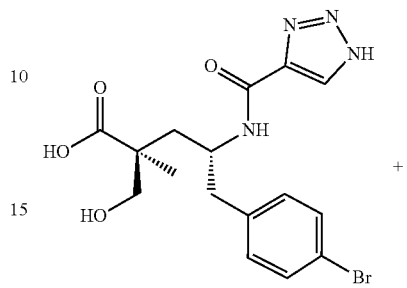

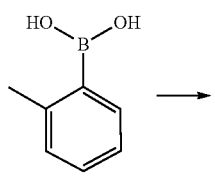

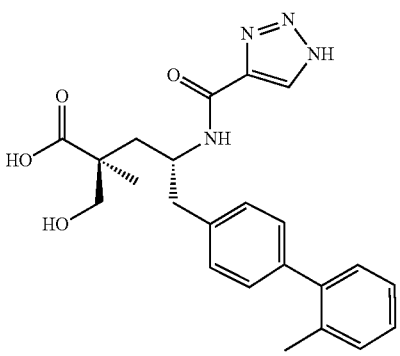

(2S,4R)-5-(4-bromophenyl)-2-hydroxymethyl-2-methyl-4-[(1H-[1,2,3]triazole-4-carbonyl)amino]pentanoic acid (38 mg, 92 μmol) was combined with 2-methylphenylboronic acid (25.1 mg, 185 μmol), sodium carbonate (29.4 mg, 277 μmol), water (0.2 mL) and dioxane (1.5 mL). The reaction vessel was sealed, air was removed by vacuum, and the vessel was purged with nitrogen. Tetrakis(triphenylphosphine)palladium (0) (21.4 mg, 18 μmol) was quickly added and air was removed by vacuum. The mixture was heated at 90° C. for 45 minutes. The mixture was acidified to pH~3 and filtered, and the solvate was concentrated. The residue was dissolved in AcOH (0.7 mL) and purified by preparative HPLC to yield the title compound (13.3 mg). MS m/z [M+H]+ calc'd for $C_{23}H_{26}N_4O_4$, 423.20; found 423.2.

87

2D: (2S,4R)-5-(3'-Chlorobiphenyl-4-yl)-2-hydroxymethyl-2-methyl-4-[(1H-[1,2,3]triazole-4-carbonyl)amino]pentanoic Acid

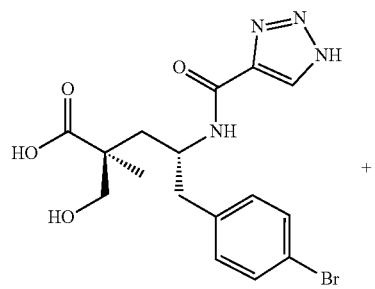

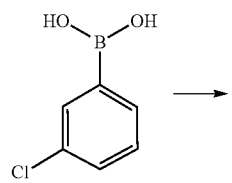

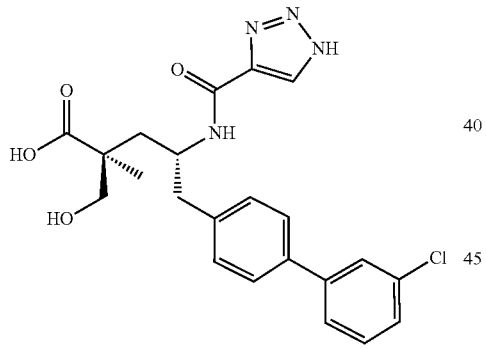

(2S,4R)-5-(4-bromophenyl)-2-hydroxymethyl-2-methyl-4-[(1H-[1,2,3]triazole-4-carbonyl)amino]pentanoic acid (38 mg, 92 μmol) was combined with 3-chlorophenylboronic acid (28.9 mg, 185 μmol), sodium carbonate (29.4 mg, 277 μmol), water (0.2 mL) and dioxane (1.5 mL). The reaction vessel was sealed, air was removed by vacuum, and the vessel was purged with nitrogen. Tetrakis(triphenylphosphine)palladium (0) (21.4 mg, 18 μmol) was quickly added and air was removed by vacuum. The mixture was heated at 90° C. for 45 minutes. The mixture was acidified to pH~3 and filtered, and the solvate was concentrated. The residue was dissolved in AcOH (0.7 mL) and purified by preparative HPLC to yield the title compound (8.1 mg). MS m/z [M+H]$^+$ calc'd for $C_{22}H_{23}ClN_4O_4$, 443.14; found 443.2.

88

2E: (2S,4R)-5-(5'-Chloro-2'-fluorobiphenyl-4-yl)-2-hydroxymethyl-2-methyl-4-[(1H-[1,2,3]triazole-4-carbonyl)amino]pentanoic Acid

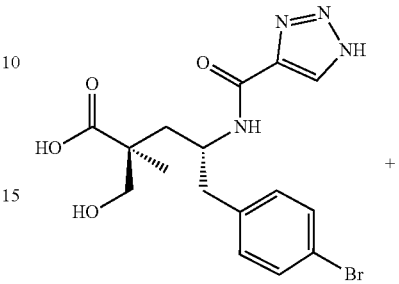

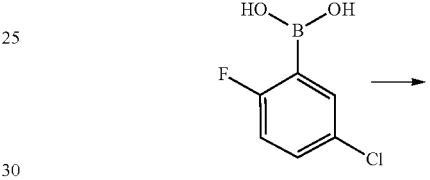

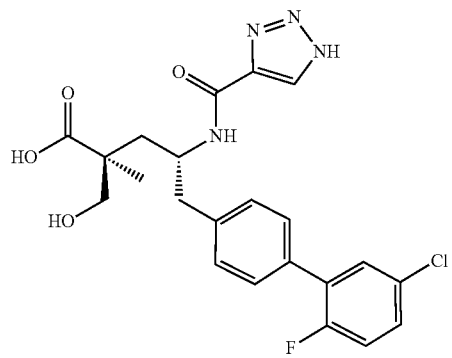

(2S,4R)-5-(4-bromophenyl)-2-hydroxymethyl-2-methyl-4-[(1H-[1,2,3]triazole-4-carbonyl)amino]pentanoic acid (38 mg, 92 μmol) was combined with 5-chloro-2-fluorophenylboronic acid (32.2 mg, 185 μmol), sodium carbonate (29.4 mg, 277 μmol), water (0.2 mL) and dioxane (1.5 mL). The reaction vessel was sealed, air was removed by vacuum, and the vessel was purged with nitrogen. Tetrakis(triphenylphosphine)palladium (0) (21.4 mg, 18 μmol) was quickly added and air was removed by vacuum. The mixture was heated at 90° C. for 45 minutes. The mixture was acidified to pH~3 and filtered, and the solvate was concentrated. The residue was dissolved in AcOH (0.7 mL) and purified by preparative HPLC to yield the title compound (2 mg). MS m/z [M+H]$^+$ calc'd for $C_{22}H_{22}ClFN_4O_4$, 461.13; found 461.2.

2F: (2S,4R)-5-(2',5'-Dichlorobiphenyl-4-yl)-2-hydroxymethyl-2-methyl-4-[(1H-[1,2,3]triazole-4-carbonyl)amino]pentanoic Acid

2G: (2S,4R)-5-(5'-Chloro-2'-methylbiphenyl-4-yl)-2-hydroxymethyl-2-methyl-4-[(1H-[1,2,3]triazole-4-carbonyl)amino]pentanoic Acid

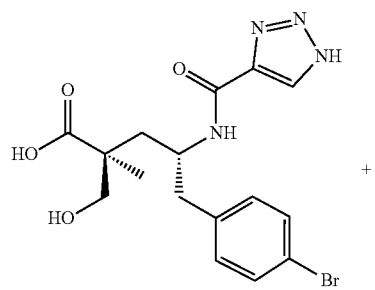 +

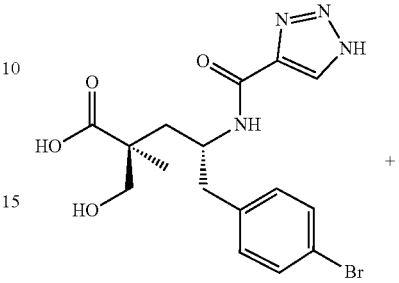 +

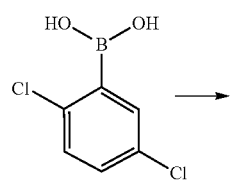

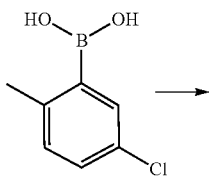

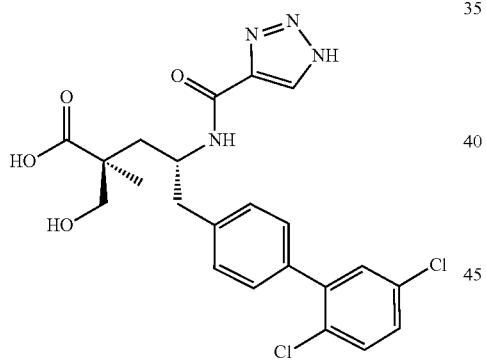

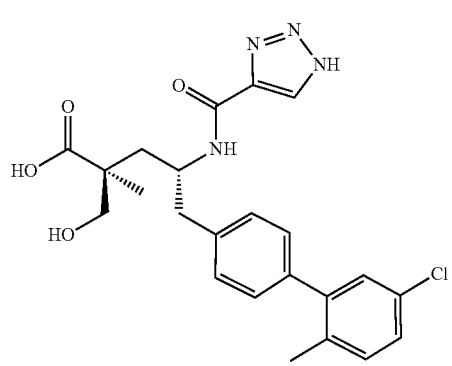

(2S,4R)-5-(4-bromophenyl)-2-hydroxymethyl-2-methyl-4-[(1H-[1,2,3]triazole-4-carbonyl)amino]pentanoic acid (38 mg, 92 μmol) was combined with 2,5-dichlorophenylboronic acid (35.3 mg, 185 μmol), sodium carbonate (29.4 mg, 277 μmol), water (0.2 mL) and dioxane (1.5 mL). The reaction vessel was sealed, air was removed by vacuum, and the vessel was purged with nitrogen. Tetrakis(triphenylphosphine)palladium (0) (21.4 mg, 18 μmol) was quickly added and air was removed by vacuum. The mixture was heated at 90° C. for 45 minutes. The mixture was acidified to pH~3 and filtered, and the solvate was concentrated. The residue was dissolved in AcOH (0.7 mL) and purified by preparative HPLC to yield the title compound (4.6 mg). MS m/z [M+H]$^+$ calc'd for $C_{22}H_{22}Cl_2N_4O_4$, 477.10; found 478.2.

(2S,4R)-5-(4-bromophenyl)-2-hydroxymethyl-2-methyl-4-[(1H-[1,2,3]triazole-4-carbonyl)amino]pentanoic acid (38 mg, 92 μmol) was combined with 5-chloro-2-methylphenylboronic acid (31.4 mg, 185 μmol), sodium carbonate (29.4 mg, 277 μmol), water (0.2 mL) and dioxane (1.5 mL). The reaction vessel was sealed, air was removed by vacuum, and the vessel was purged with nitrogen. Tetrakis(triphenylphosphine)palladium (0) (21.4 mg, 18 μmol) was quickly added and air was removed by vacuum. The mixture was heated at 90° C. for 45 minutes. The mixture was acidified to pH~3 and filtered, and the solvate was concentrated. The residue was dissolved in AcOH (0.7 mL) and purified by preparative HPLC to yield the title compound (12.1 mg). MS m/z [M+H]$^+$ calc'd for $C_{23}H_{25}ClN_4O_4$, 457.16; found 457.2.

2H: (2S,4R)-5-(3'-Cyanobiphenyl-4-yl)-2-hydroxymethyl-2-methyl-4-[(1H-[1,2,3]triazole-4-carbonyl)amino]pentanoic Acid

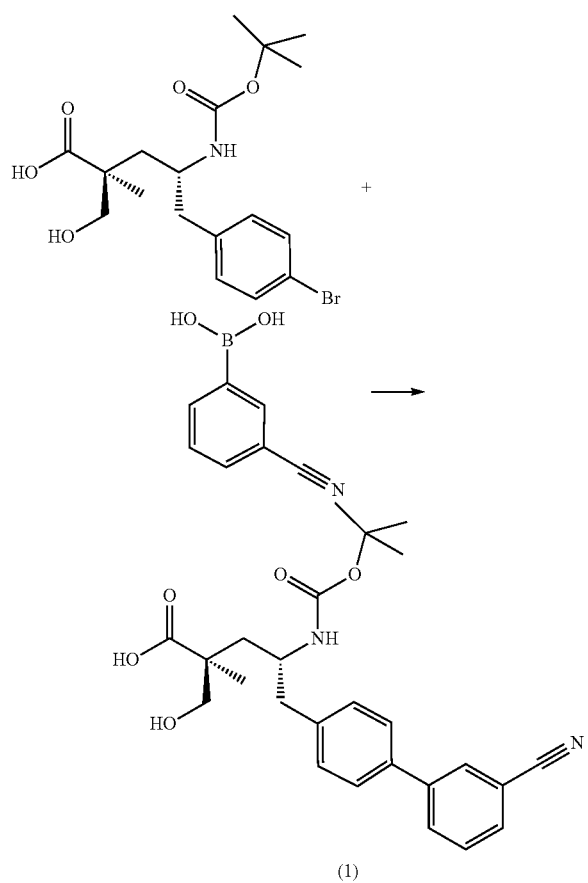

(2S,4R)-5-(4-Bromophenyl)-4-t-butoxycarbonylamino-2-hydroxymethyl-2-methylpentanoic acid (40 mg, 96 µmol) was combined with 3-cyanophenylboronic acid (14 mg, 96 µmol), sodium carbonate (10.2 mg, 96 µmol), water (0.5 mL) and dioxane (2 mL). The reaction vessel was sealed, air was removed by vacuum, and the vessel was purged with nitrogen. Tetrakis(triphenylphosphine)palladium (0) (11 mg, 9.6 µmol) was quickly added, air was removed by vacuum, and the vessel was purged with nitrogen. The mixture was heated at 90° C. for 45 minutes. The mixture was filtered and the solvate was concentrated. The residue was dissolved in AcOH and purified by reverse phase chromatography to yield Compound 1 (30 mg).

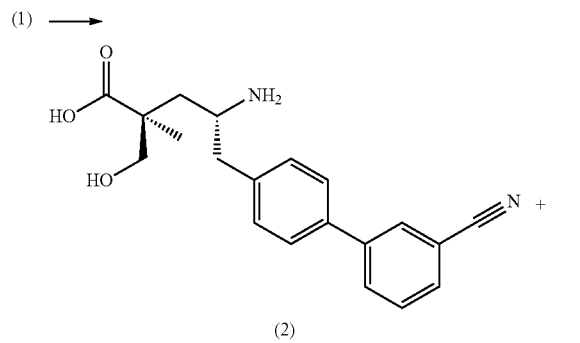

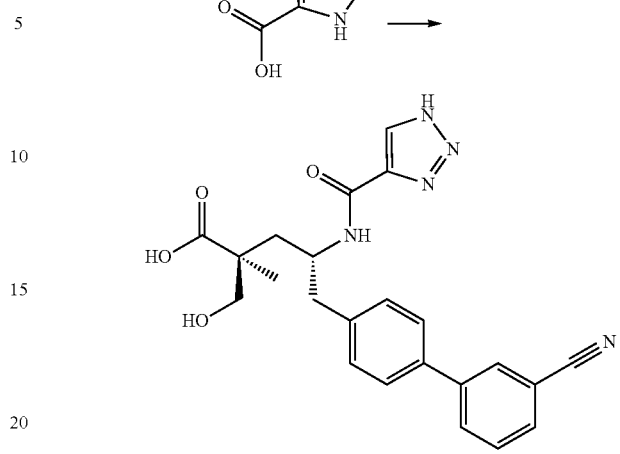

Compound 1 (30 mg, 68 µmol) was combined with MeCN (1 mL) and 4M HCl in 1,4-dioxane (103 µL, 410 µmol) and stirred for 10 minutes. The mixture was then concentrated under reduced pressure to yield Compound 2 (27 mg).

3H-[1,2,3]triazole-4-carboxylic acid (9.1 mg, 80 µmol) was combined with HATU (30 mg, 80 µmol) in DMF (0.5 mL) and stirred for 5 minutes. Compound 2 (27 mg, 80 µmol) was added, followed by DIPEA (42 µL, 240 µmol), and the resulting mixture was stirred for 30 minutes. The solvent was evaporated and the residue was dissolved in AcOH and purified by reverse phase to yield the title compound (3 mg). MS m/z [M+H]+ calc'd for $C_{23}H_{23}N_5O_4$, 434.18; found 434.

2I: (2S,4R)-2-Hydroxymethyl-2-methyl-5-(3'-methylbiphenyl-4-yl)-4-[(1H-[1,2,3]triazole-4-carbonyl)amino]pentanoic Acid

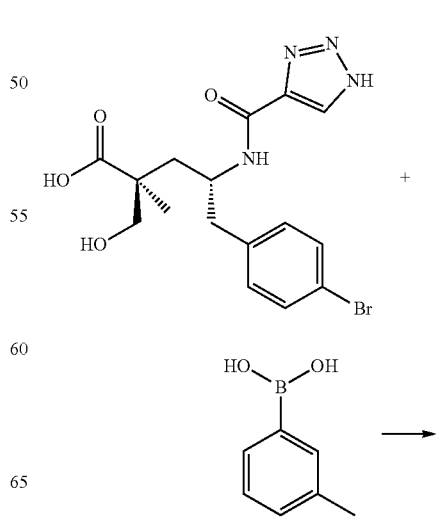

-continued

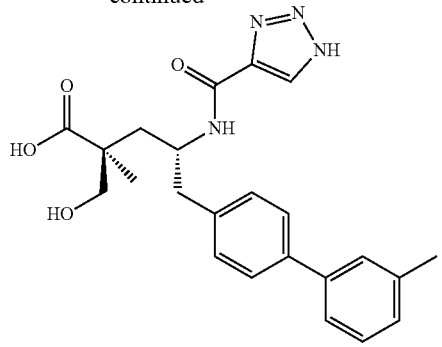

(2S,4R)-5-(4-bromophenyl)-2-hydroxymethyl-2-methyl-4-[(1H-[1,2,3]triazole-4-carbonyl)amino]pentanoic acid (38 mg, 92 µmol) was combined with 3-methylphenylboronic acid (25.1 mg, 185 µmol), sodium carbonate (29.4 mg, 277 µmol), water (0.2 mL) and dioxane (1.5 mL). The reaction vessel was sealed, air was removed by vacuum, and the vessel was purged with nitrogen. Tetrakis(triphenylphosphine)palladium (0) (21.4 mg, 18 µmol) was quickly added and air was removed by vacuum. The mixture was heated at 90° C. for 45 minutes. The mixture was acidified to pH~3 and filtered, and the solvate was concentrated. The residue was dissolved in AcOH (0.7 mL) and purified by preparative HPLC to yield the title compound (10 mg).

2J: (2S,4R)-5-(3'-Chlorobiphenyl-4-yl)-2-methoxymethyl-2-methyl-4-[(1H-[1.2.3]triazole-4-carbonyl)amino]pentanoic Acid

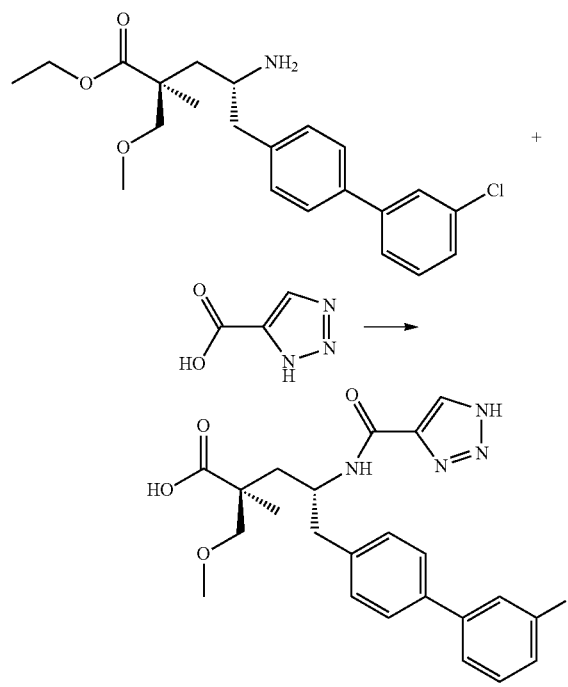

3H-[1,2,3]Triazole-4-carboxylic acid (3.5 mg, 31 µmol) and HATU (12 mg, 31 µmol) were combined in DMF (0.5 mL) and stirred for 5 minutes. A solution of (2S,4R)-4-amino-5-(3'-chlorobiphenyl-4-yl)-2-methoxymethyl-2-methylpentanoic acid ethyl ester (12 mg, 31 µmol) and DIPEA (16 µL, 93 µmol) in DMF (0.5 mL) was added and the resulting mixture was stirred for 20 minutes then concentrated under reduced pressure.

The residue was combined with THF (0.6 mL) and NaOH (124 µL, 124 µmol) and stirred at 60° C. for 2 hours, then concentrated under reduced pressure. The residue was dissolved in AcOH and purified by reverse phase chromatography to yield the title compound (4.0 mg). MS m/z [M+H]+ calc'd for $C_{23}H_{25}ClN_4O_4$, 457.16; found 457.2.

2K: (2S,4R)-5-(3'-Chlorobiphenyl-4-yl)-2-ethoxymethyl-2-methyl-4-[(3H-[1,2,3]triazole-4-carbonyl)amino]pentanoic Acid

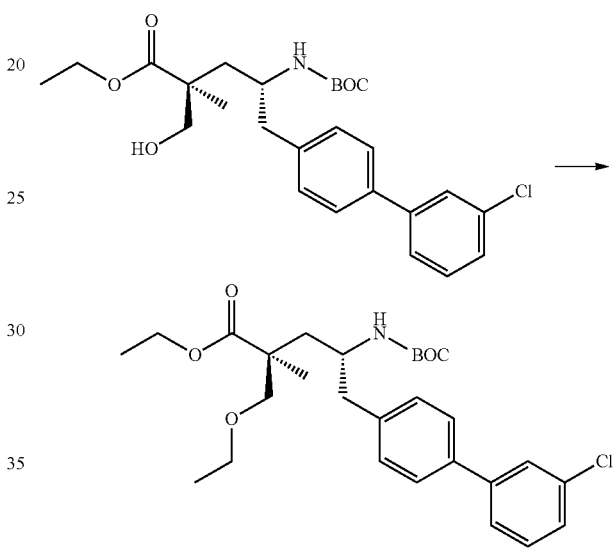

(1)

Into a vial was added (2S,4R)-4-t-butoxycarbonylamino-5-(3'-chlorobiphenyl-4-yl)-2-hydroxymethyl-2-methylpentanoic acid ethyl ester (400 mg, 840 µmol), tetrabutylammonium hydrogen sulfate (57 mg, 168 µmol), DCM (1 mL) and NaOH (588 µL, 5.9 mmol), followed by diethylsulfate (518 mg, 3.4 mmol). The reaction vessel was capped and stirred vigorously overnight. The mixture was extracted with DCM and water, purified (normal phase chromatography 0-60% EtOAc:hexanes), then concentrated under reduced pressure to yield Compound 1 (180 mg).

(1) →

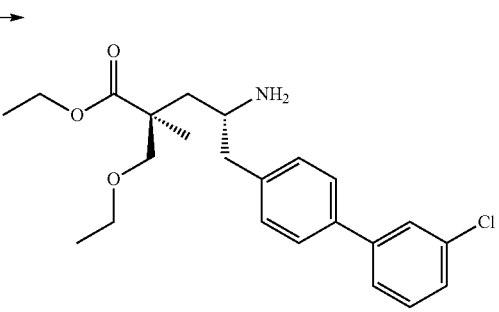

(2)

Compound 1 (87 mg, 173 μmol) in MeCN (1 mL) was combined with 4N HCl in dioxane (0.3 mL). The mixture was stirred for 10 minutes then concentrated under reduced pressure to yield Compound 2.

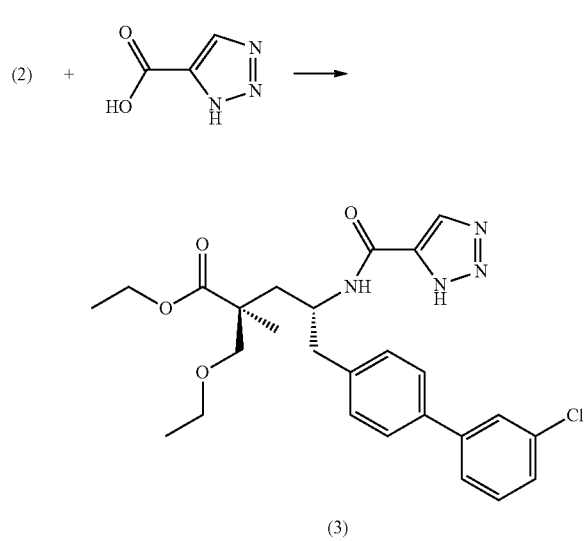

Compound 2 (33.7 mg, 83 μmol) was combined with HATU (38.0 mg, 100 μmol), 3H-[1,2,3]triazole-4-carboxylic acid (12.3 mg, 108 μmol) in DMF (0.5 mL). DIPEA (43.7 μL, 250 μmol) was added and the mixture was stirred for 2 hours. EtOAc was added, followed by a saturated aqueous NH₄Cl solution. The mixture was stirred for 10 minutes then concentrated under reduced pressure to yield Compound 3.

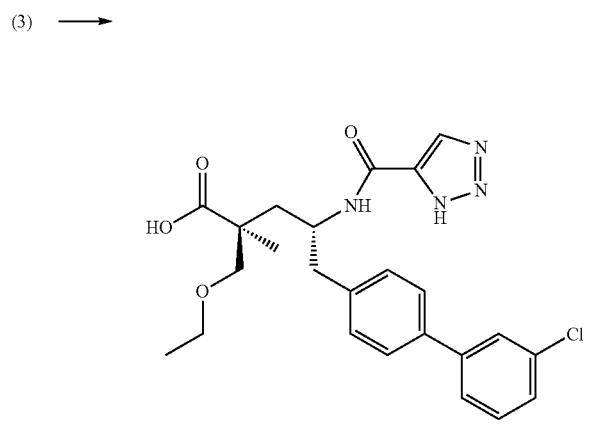

Compound 3 (40.7 mg, 82 μmol) was combined with THF (0.6 mL) and NaOH (326 μL, 326 μmol) and a few drop of MeOH. The resulting mixture was stirred at 60° C. for 2 hours, then concentrated under reduced pressure. The residue was dissolved in AcOH and purified by reverse phase to yield the title compound (12 mg). MS m/z [M+H]⁺ calc'd for $C_{24}H_{27}ClN_4O_4$, 471.17; found 471.2.

2L: (2S,4R)-5-(3'-Chlorobiphenyl-4-yl)-2-(2-hydroxyethoxymethyl)-2-methyl-4-[(1H-[1.2.3]triazole-4-carbonyl)amino]pentanoic Acid

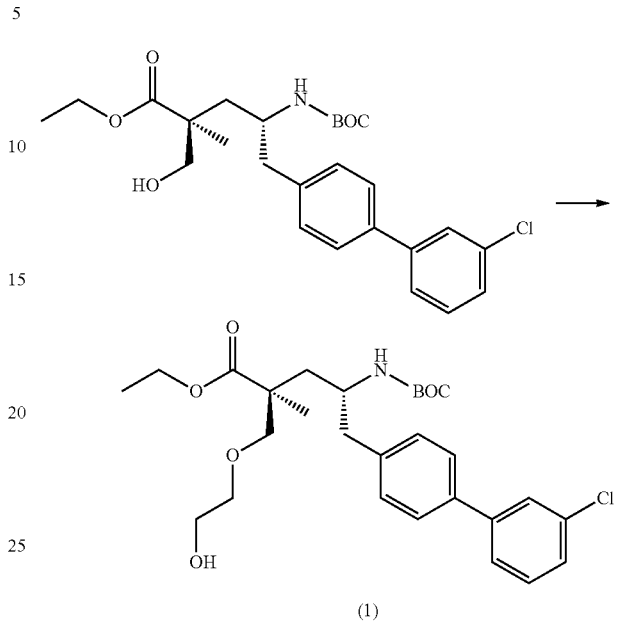

Into a vial was added (2S,4R)-4-t-butoxycarbonylamino-5-(3'-chlorobiphenyl-4-yl)-2-hydroxymethyl-2-methylpentanoic acid ethyl ester (400 mg, 840 μmol), tetrabutylammonium hydrogen sulfate (57 mg, 168 μmol), DCM (1 mL) and NaOH (588 μL, 5.9 mmol), followed by [1,3,2]dioxathiolane 2,2-dioxide (417 mg, 3.4 mmol). The reaction vessel was capped and stirred vigorously overnight. The mixture was extracted with DCM and water, purified (normal phase chromatography 0-60% EtOAc:hexanes), then concentrated under reduced pressure to yield Compound 1 (90 mg).

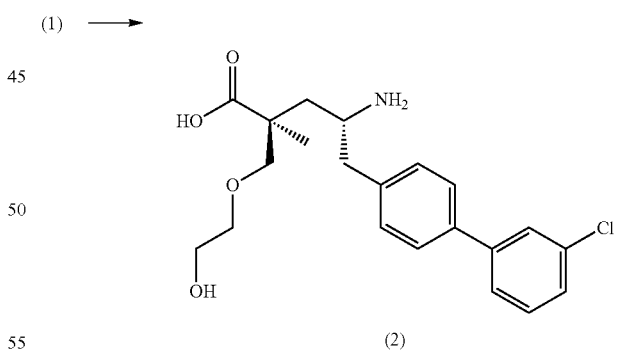

Compound 1 (90 mg, 173 μmol) in MeCN (1 mL) was combined with 4N HCl in dioxane (0.3 mL). The mixture was stirred for 10 minutes then concentrated under reduced pressure to yield Compound 2.

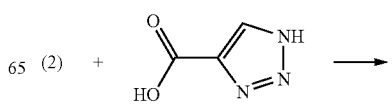

-continued

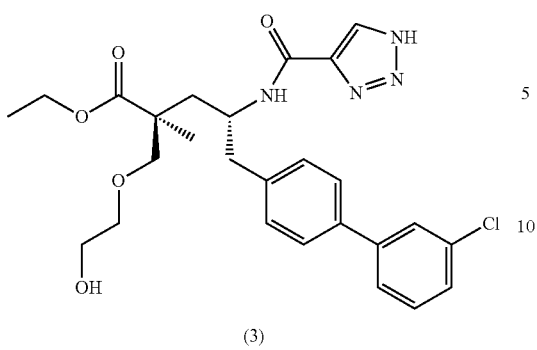

(3)

Compound 2 (35 mg, 83 μmol) was combined with HATU (38 mg, 100 μmol), 1H-[1,2,3]triazole-4-carboxylic acid (12.3 mg, 108 μmol) in DMF (0.5 mL). DIPEA (43.7 μL, 250 μmol) was added and the mixture was stirred for 2 hours. EtOAc was added, followed by a saturated aqueous NH₄Cl solution. The mixture was stirred for 10 minutes then concentrated under reduced pressure to yield Compound 3.

(3) ⟶

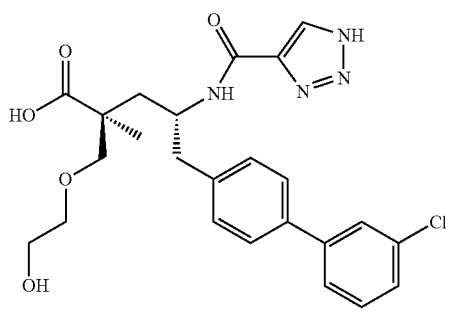

Compound 3 (42 mg, 82 μmol) was combined with THF (0.6 mL) and NaOH (326 μL, 326 μmol) and a few drop of MeOH. The resulting mixture was stirred at 60° C. for 2 hours, then concentrated under reduced pressure. The residue was dissolved in AcOH and purified by reverse phase to yield the title compound (11 mg). MS m/z [M+H]⁺ calc'd for $C_{24}H_{27}ClN_4O_5$, 487.17; found 487.2.

2M: (2S,4R)-5-(3'-Chlorobiphenyl-4-yl)-2-(3-hydroxypropoxymethyl)-2-methyl-4-[(1H-[1,2,3]triazole-4-carbonyl)amino]pentanoic Acid

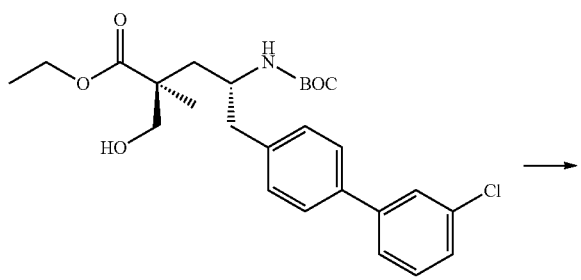

-continued

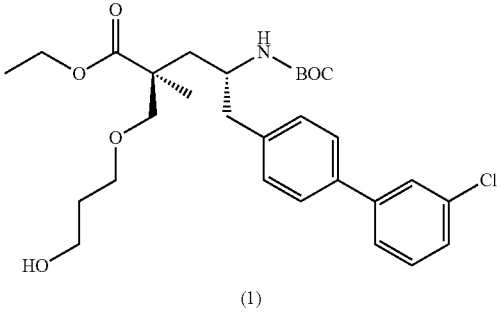

(1)

Into a vial was added (2S,4R)-4-t-butoxycarbonylamino-5-(3'-chlorobiphenyl-4-yl)-2-hydroxymethyl-2-methylpentanoic acid ethyl ester (67 mg, 140 μmol), tetrabutyl-ammonium hydrogen sulfate (9.5 mg, 28 μmol), DCM (1 mL) and NaOH (98 μL, 982 mol), followed by 1,3-propanediol cyclic sulfate (78 mg, 561 μmol). The mixture was stirred overnight then extracted with DCM and purified (normal phase chromatography (0-100% EtOAc:hexanes) to yield Compound 1 (7 mg).

(1) ⟶

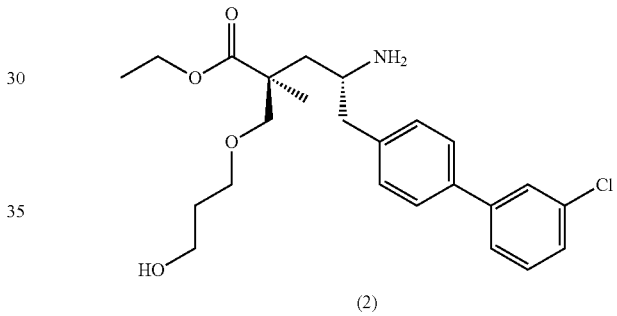

(2)

Compound 1 (26.3 mg, 49 μmol) in MeCN (0.3 mL) was combined with 4N HCl in dioxane (0.3 mL). The mixture was stirred for 10 minutes then concentrated under reduced pressure to yield Compound 2.

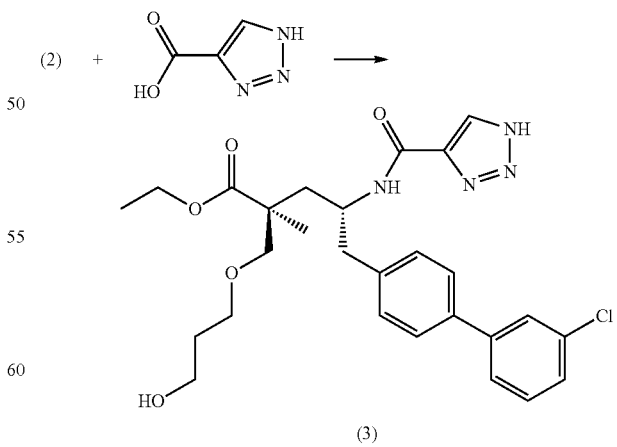

(3)

Compound 2 (18 mg, 47 μmol) was dissolved in DMF (0.3 mL) and 1H-1,2,3-triazole-4-carboxylic acid (5.3 mg, 47 μmol). HATU (18 mg, 47 μmol) was added, followed by DIPEA (25 µL, 141 µmol). The mixture was stirred for 30 minutes then concentrated under reduced pressure to yield Compound 3, which was used without further purification.

(3) ⟶

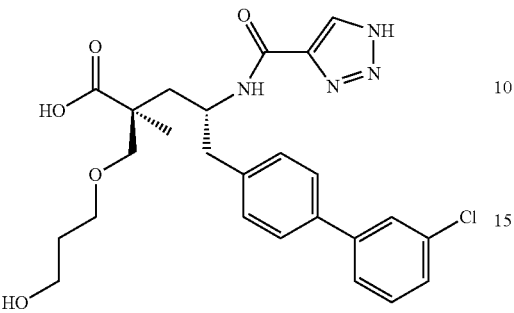

Compound 3 (23 mg, 47 µmol) was dissolved in THF and NaOH (188 µL, 188 µmol) was added and the mixture was stirred at 60° C. overnight. the residue was dissolved in AcOH and purified by preparative HPLC to yield the title compound (1.2 mg). MS m/z [M+H]$^+$ calc'd for $C_{25}H_{29}ClN_4O_5$, 501.18; found 502.2.

2N: (2S,4R)-5-(5'-Chloro-2'-fluorobiphenyl-4-yl)-2-methoxymethyl-2-methyl-4-[(1H-[1.2.3]triazole-4-carbonyl)amino]pentanoic Acid

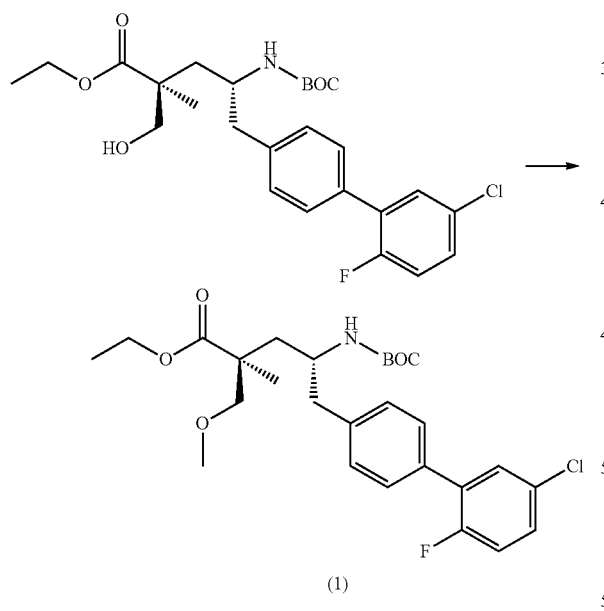

Into a vial was added (2S,4R)-4-t-butoxycarbonylamino-5-(5'-chloro-2'-fluorobiphenyl-4-yl)-2-hydroxymethyl-2-methylpentanoic acid ethyl ester (82 mg, 166 µmol), tetrabutylammonium hydrogen sulfate (11 mg, 33 µmol), DCM (1 mL) and NaOH (116 µL, 1.2 mmol), followed by dimethyl sulfate (84 mg, 664 mmol). The reaction vessel was capped and stirred vigorously overnight. The mixture was extracted with DCM and concentrated under reduced pressure. The residue was dissolved in AcOH and purified by reverse phase chromatography (30-100% MeCN in water) to yield Compound 1 (30 mg).

(1) ⟶

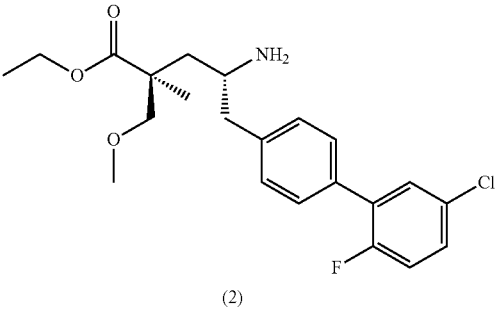

Compound 1 (84 mg, 166 µmol) in MeCN (1 mL) was combined with 4N HCl in dioxane (0.3 mL). The mixture was stirred for 10 minutes then concentrated under reduced pressure to yield Compound 2.

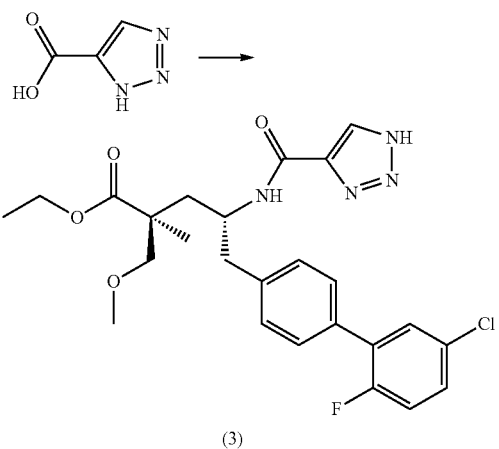

3H-[1,2,3]triazole-4-carboxylic acid (21 mg, 183 µmol) was combined with HATU (69 mg, 183 µmol), in DMF (0.5 mL), Compound 2 (68 mg, 166 µmol), and DIPEA (87 µL, 498 µmol). The resulting mixture was stirred for 20 minutes then concentrated under reduced pressure. The residue was purified (normal phase chromatography 0-80% EtOAc:hexanes) to yield Compound 3.

(3) ⟶

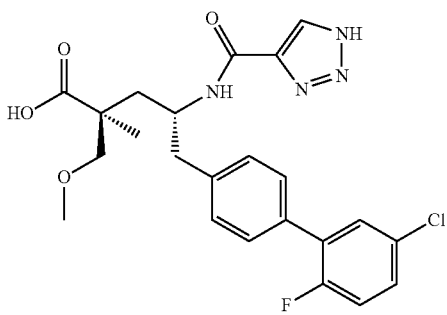

Compound 3 (65 mg, 129 µmol) was combined with THF (0.6 mL) and NaOH (516 µL, 516 µmol). The resulting mixture was stirred at 60° C. for 2 hours. A small amount of NaOH and MeOH was added and the mixture was stirred overnight. The mixture was acidified with concentrated HCl 2O: (2S,4R)-5-(5'-Chloro-2'-fluoro-biphenyl-4-yl)-2-ethoxymethyl-2-methyl-4-[(1H-[1,2,3]triazole-4-carbonyl)amino]pentanoic Acid

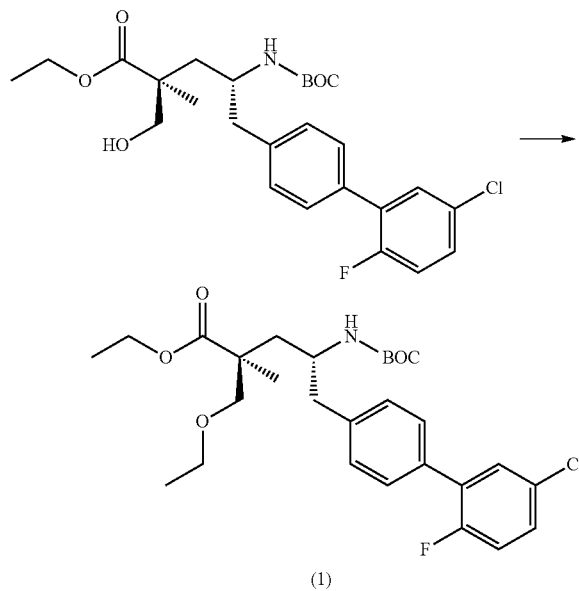

Into a vial was added (2S,4R)-4-t-butoxycarbonylamino-5-(5'-chloro-2'-fluorobiphenyl-4-yl)-2-hydroxymethyl-2-methylpentanoic acid ethyl ester (415 mg, 840 µmol), tetrabutylammonium hydrogen sulfate (57 mg, 168 µmol), DCM (1 mL) and NaOH (588 µL, 5.9 mmol), followed by diethylsulfate (518 mg, 3.4 mmol). The reaction vessel was capped and stirred vigorously overnight. The mixture was extracted with DCM and water, purified (normal phase chromatography 0-60% EtOAc:hexanes), then concentrated under reduced pressure to yield Compound 1 (110 mg).

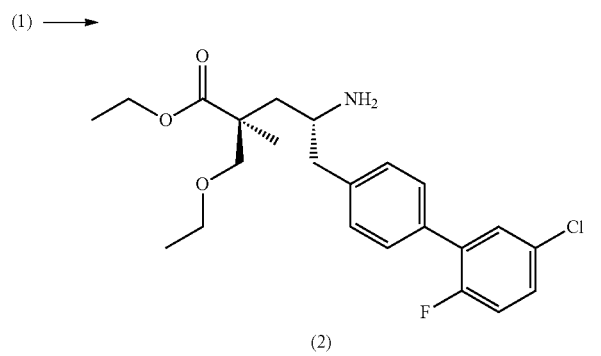

Compound 1 (90 mg, 173 µmol) in MeCN (1 mL) was combined with 4N HCl in dioxane (0.3 mL). The mixture was stirred for 10 minutes then concentrated under reduced pressure to yield Compound 2.

to pH-4, then concentrated under reduced pressure. The residue was dissolved in AcOH and purified by preparative HPLC to yield the title compound (35 mg). MS m/z [M+H]⁺ calc'd for $C_{23}H_{24}ClFN_4O_4$, 475.15; found 475.2.

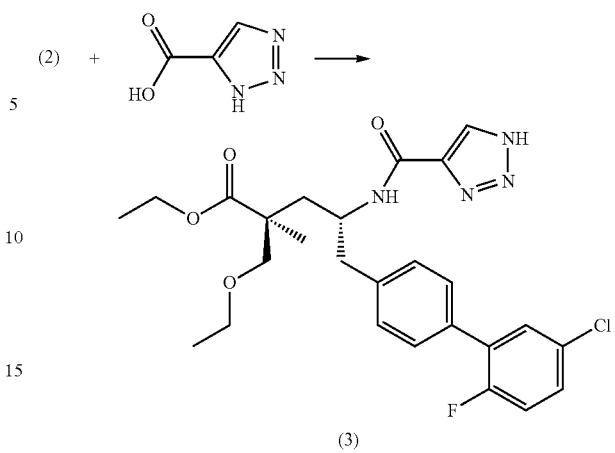

Compound 2 (35.2 mg, 83 µmol) was combined with HATU (38.0 mg, 100 µmol), 3H-[1,2,3]triazole-4-carboxylic acid (12.3 mg, 108 µmol) in DMF (0.5 mL). DIPEA (43.7 µL, 250 µmol) was added and the mixture was stirred for 2 hours. EtOAc was added, followed by a saturated aqueous NH₄Cl solution. The mixture was stirred for 10 minutes then concentrated under reduced pressure to yield Compound 3.

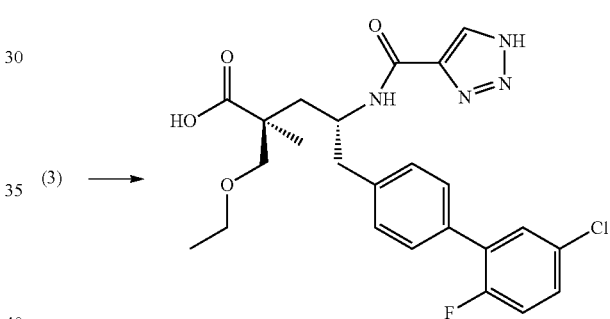

Compound 3 (42.2 mg, 82 µmol) was combined with THF (0.6 mL) and NaOH (326 µL, 326 µmol) and a few drops of MeOH. The resulting mixture was stirred at 60° C. for 2 hours, then concentrated under reduced pressure. The residue was dissolved in AcOH and purified by reverse phase to yield the title compound (23 mg). MS m/z [M+H]⁺ calc'd for $C_{24}H_{26}ClFN_4O_4$, 489.16; found 489.2.

2P: (2S,4R)-5-(5'-Chloro-2'-fluorobiphenyl-4-yl)-2-(3-hydroxypropoxymethyl)-2-methyl-4-[(3H-[1,2,3]triazole-4-carbonyl)amino]pentanoic Acid

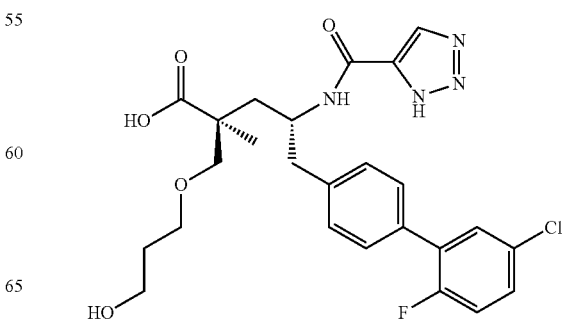

The title compounds was also prepared (4 mg). MS m/z [M+H]$^+$ calc'd for $C_{25}H_{28}ClFN_4O_5$, 519.17; found 519.

2Q. (2S,4R)-5-(5'-Chloro-2'-fluorobiphenyl-4-yl)-2-methyl-2-pentyloxymethyl-4-[(3H-[1,2,3]triazole-4-carbonyl)amino]pentanoic Acid

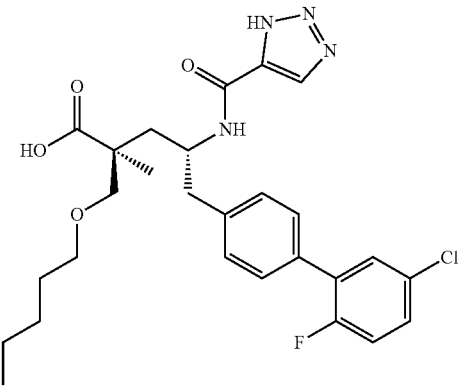 [SMILES: CCCCCOC[C@](C)(C[C@@H](Cc1ccc(-c2cc(Cl)ccc2F)cc1)NC(=O)c1cnn[nH]1)C(=O)O]

The title compounds was also prepared (6 mg). MS m/z [M+H]$^+$ calc'd for $C_{27}H_{32}ClFN_4O_4$, 531.21; found 531.

2R: (2S,4R)-5-(5'-Chloro-2'-fluorobiphenyl-4-yl)-2-isopropoxymethyl-2-methyl-4-[(3H-[1,2,3]triazole-4-carbonyl)amino]pentanoic Acid

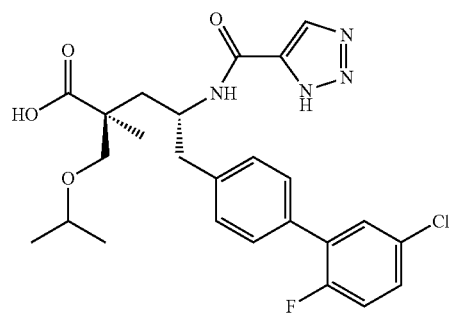 [SMILES: CC(C)OC[C@](C)(C[C@@H](Cc1ccc(-c2cc(Cl)ccc2F)cc1)NC(=O)c1cnn[nH]1)C(=O)O]

The title compounds was also prepared (7 mg). MS m/z [M+H]$^+$ calc'd for $C_{25}H_{28}ClFN_4O_4$, 503.18; found 503.

2S: (2S,4R)-5-(5'-Chloro-2'-fluorobiphenyl-4-yl)-2-(2-hydroxyethoxymethyl)-2-methyl-4-[(3H-[1,2,3]triazole-4-carbonyl)amino]pentanoic Acid

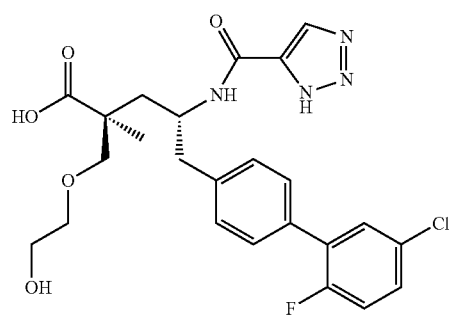 [SMILES: C[C@@](COCCO)(C[C@@H](Cc1ccc(-c2cc(Cl)ccc2F)cc1)NC(=O)c1cnn[nH]1)C(=O)O]

The title compounds was also prepared (4 mg). MS m/z [M+H]$^+$ calc'd for $C_{24}H_{24}FN_7O_2$, 462.20; found 462.2.

Example 3

It is understood that the compounds of Example 3 can exist in a tautomer form, and that both forms are covered by this example. For example, (2S,4R)-5-(3'-fluorobiphenyl-4-yl)-2-hydroxymethyl-2-methyl-4-[(3H-[1,2,3]triazole-4-carbonyl)amino]pentanoic acid is depicted in Example 3A but it is understood that this compound can exist in a tautomer form, for example, as (2S,4R)-5-(3'-fluorobiphenyl-4-yl)-2-hydroxymethyl-2-methyl-4-[(1H-[1,2,3]triazole-4-carbonyl)amino]pentanoic acid. The same is true for the compound in Example 3B.

3A: (2S,4R)-5-(3'-Fluorobiphenyl-4-yl)-2-hydroxymethyl-2-methyl-4-[(3H-[1,2,3]triazole-4-carbonyl)amino]pentanoic Acid

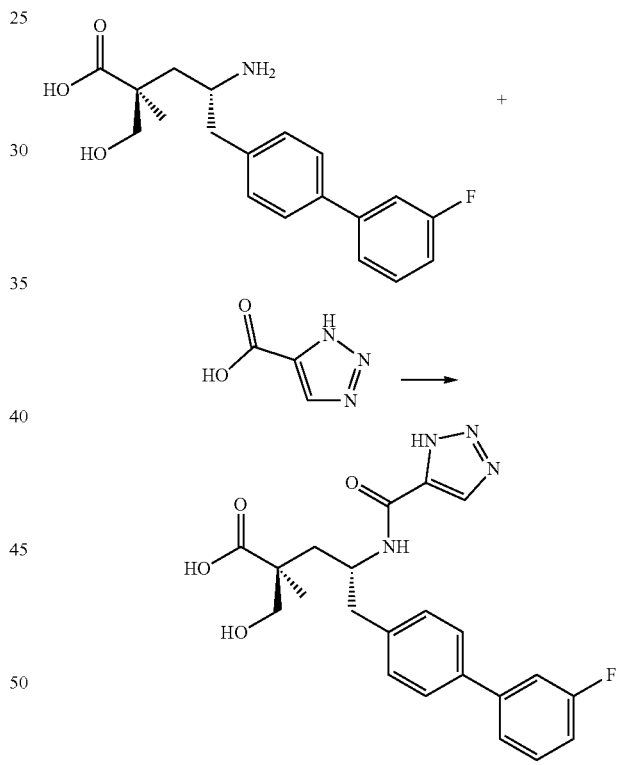

1,2,3-Triazole-4-carboxylic acid (27.3 mg, 241 μmol) was combined with EDC (42.7 μL, 241 μmol), 4-methylmorpholine (1 eq.) and HOBt (32.6 mg, 241 μmol) in DMF (0.2 mL). The resulting mixture was stirred for 5 minutes at room temperature. A solution (2S,4R)-4-amino-5-(3'-fluorobiphenyl-4-yl)-2-hydroxymethyl-2-methylpentanoic acid (80 mg, 240 μmol) and 4-methylmorpholine (53.1 μL, 483 μmol) in DMF (0.3 mL) was added, and the resulting mixture was stirred for 15 minutes. The reaction was quenched with ACOH and the product was purified by preparative HPLC and lyophilized to yield the title compound (30 mg). MS m/z [M+H]$^+$ calc'd for $C_{22}H_{23}FN_4O_4$, 427.17; found 427.2.

3B: (2S,4R)-5-(2'-Fluorobiphenyl-4-yl)-2-hydroxymethyl-2-methyl-4-[(3H-[1,2,3]triazole-4-carbonyl)amino]pentanoic Acid

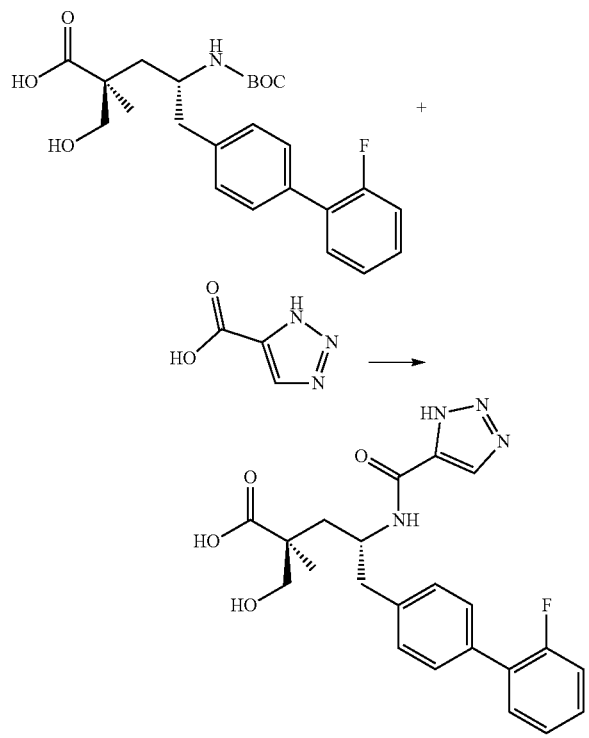

1,2,3-Triazole-4-carboxylic acid (30 mg, 260 µmol) was combined with DIPEA (92.4 µL, 531 µmol) and HATU (101 mg, 265 µmol) in DMF (0.2 mL). The resulting mixture was stirred for 5 minutes at room temperature. A solution (2S,4R)-4-t-butoxycarbonylamino-5-(2'-fluorobiphenyl-4-yl)-2-hydroxymethyl-2-methylpentanoic acid (114 mg, 265 µmol) and DIPEA (3 eq.) in DMF (0.2 mL) was added, and the resulting mixture was stirred for 15 minutes. The reaction was quenched with ACOH and the product was purified by preparative HPLC and lyophilized to yield the title compound (16 mg). MS m/z [M+H]⁺ calc'd for $C_{22}H_{23}FN_4O_4$, 427.17; found 427.2.

Example 4

4A: (2S,4R)-5-(2'-Fluorobiphenyl-4-yl)-2-hydroxymethyl-4-(1-hydroxy-1H-[[1,2,3]triazole-4-carbonyl)amino]-2-methylpentanoic Acid

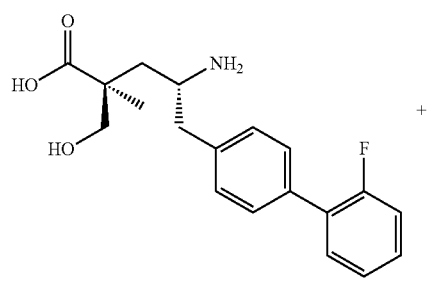

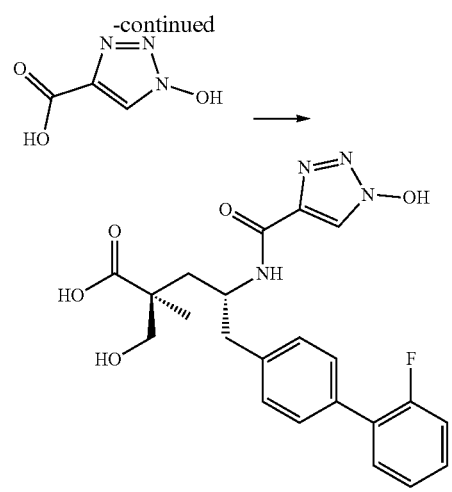

1-Hydroxy-1H-1,2,3-triazole-4-carboxylic acid (15 mg, 116 µmol) was combined with DIPEA (40.5 µL, 232 µmol) and HATU (44.2 mg, 116 µmol) in DMF (0.2 mL). The resulting mixture was stirred for 5 minutes at room temperature. A solution (2S,4R)-4-amino-5-(2'-fluorobiphenyl-4-yl)-2-hydroxymethyl-2-methylpentanoic acid (38.5 mg, 166 µmol) and DIPEA (3 eq.) in DMF (0.2 mL) was added, and the resulting mixture was stirred for 15 minutes. The reaction was quenched with ACOH and the product was purified by preparative HPLC and lyophilized to yield the title compound (8 mg). MS m/z [M+H]⁺ calc'd for $C_{22}H_{23}FN_4O_5$, 443.17; found 443.2.

4B: (2S,4R)-5-(5'-Chloro-2'-fluorobiphenyl-4-yl)-2-hydroxymethyl-4-[(1-methoxy-1H-[1,2,3]triazole-4-carbonyl)amino]-2-methylpentanoic Acid

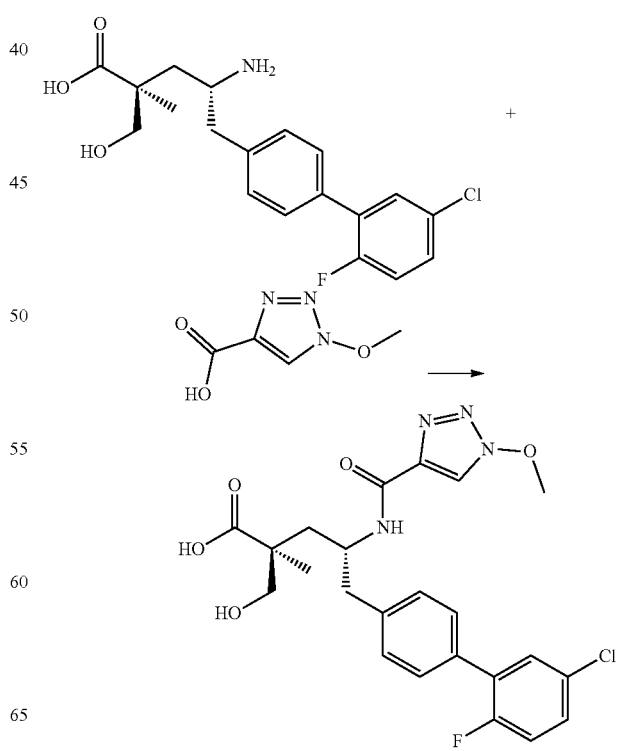

1-Methoxy-1H-[1,2,3]triazole-4-carboxylic acid (4.3 mg, 30 µmol) and HATU (11.4 mg, 30 µmol) were combined in DMF (1 mL) and stirred at room temperature for 15 minutes. (2S,4R)-4-amino-5-(5'-chloro-2'-fluorobiphenyl-4-yl)-2-hydroxymethyl-2-methylpentanoic acid (10 mg, 27 µmol) and DIPEA (14 µL, 82 µmol) were added, and the resulting mixture was stirred for 15 minutes at room temperature. The solvent was removed in vacuo and the residue was purified by preparative HPLC to yield the title compound (1.1 mg). MS m/z [M+H]$^+$ calc'd for $C_{23}H_{24}ClFN_4O_5$, 491.14; found 491.2.

4C: (2S,4R)-5-(5'-Chloro-2'-fluorobiphenyl-4-yl)-4-[(1-ethoxy-1H-[1,2,3]triazole-4-carbonyl)-amino]-2-hydroxymethyl-2-methylpentanoic Acid

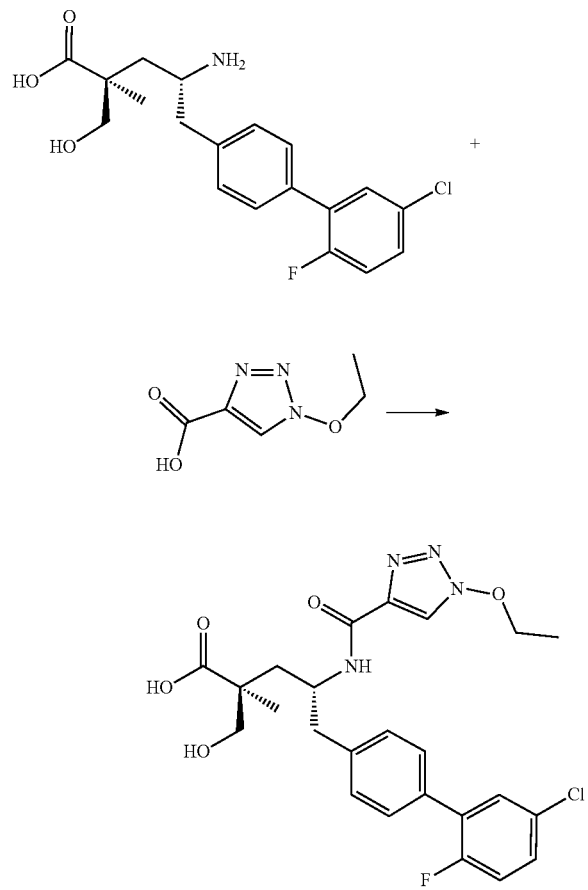

1-Ethoxy-1H-[1,2,3]triazole-4-carboxylic acid (4.7 mg, 30 µmol) and HATU (11.4 mg, 30 µmol) were combined in DMF (1 mL) and stirred at room temperature for 15 minutes. (2S,4R)-4-Amino-5-(5'-chloro-2'-fluorobiphenyl-4-yl)-2-hydroxymethyl-2-methylpentanoic acid (10 mg, 27 µmol) and DIPEA (14 µL, 82 µmol) were added, and the resulting mixture was stirred for 15 minutes at room temperature. The solvent was removed in vacuo and the residue was purified by preparative HPLC to yield the title compound (2 mg). MS m/z [M+H]$^+$ calc'd for $C_{24}H_{26}ClFN_4O_5$, 505.16; found 505.1.

Example 5

5A: (2S,4R)-5-(2'-Fluorobiphenyl-4-yl)-2-hydroxymethyl-2-methyl-4-[(2-oxo-2,3-dihydrooxazole-4-carbonyl)amino]pentanoic Acid

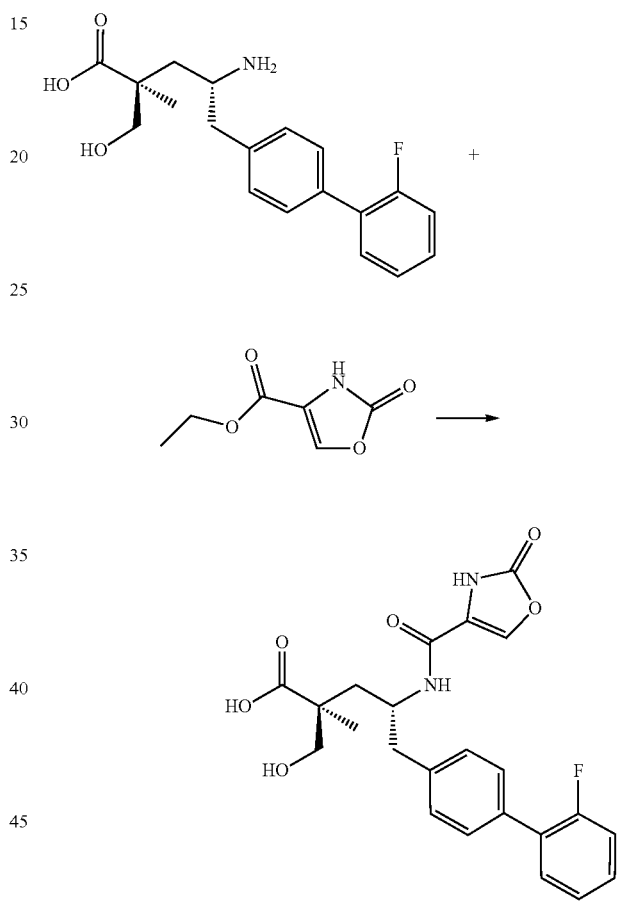

THF (1 mL, 10 mmol), ethyl 2-oxo-2,3-dihydrooxazole-4-carboxylate (12 mg, 76.4 µmol), and 1 M NaOH in water (229 µL, 229 µmol) were combined and stirred until completion. The mixture was acidified to pH~5 with 1N HCl, the solvent was evaporated in vacuo, and the product was azeotroped in toluene and dried in vacuo. To this was added a solution of DIPEA (26.6 µL, 153 µmol) and HATU (29.0 mg, 76.4 µmol) in DMF (0.2 mL), and the resulting mixture was stirred for 5 minutes at room temperature. (2S,4R)-4-Amino-5-(2'-fluorobiphenyl-4-yl)-2-hydroxymethyl-2-methylpentanoic acid (25.3 mg, 76.4 µmol) was added and the resulting mixture was stirred for 15 minutes. The reaction was quenched with EtOAc and saturated NH$_4$Cl. The product was extracted and dried. AcOH was added and the product was purified by preparative HPLC to yield the title compound (2.5 mg). MS m/z [M+H]+ calc'd for $C_{23}H_{23}FN_2O_6$, 443.15; found 443.2.

5B: (2S,4R)-5-(2'-Fluorobiphenyl-4-yl)-2-hydroxymethyl-2-methyl-4-[(2-oxo-2,3-dihydrooxazole-5-carbonyl)amino]pentanoic Acid

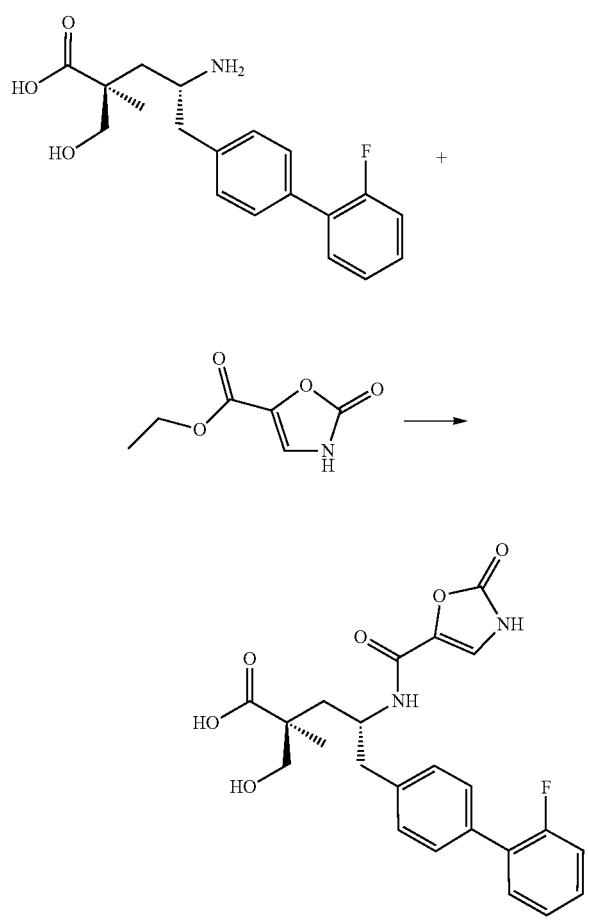

THF (1 mL, 10 mmol), ethyl 2-oxo-2,3-dihydrooxazole-5-carboxylate (12 mg, 76.4 µmol), and 1 M NaOH in water (229 µL, 229 µmol) were combined and stirred until completion. The mixture was acidified to pH~5 with 1N HCl, the solvent was evaporated in vacuo, and the product was azeotroped in toluene and dried in vacuo. To this was added a solution of DIPEA (26.6 µL, 153 µmol) and HATU (29.0 mg, 76.4 µmol) in DMF (0.2 mL), and the resulting mixture was stirred for 5 minutes at room temperature. (2S,4R)-4-Amino-5-(2'-fluorobiphenyl-4-yl)-2-hydroxymethyl-2-methylpentanoic acid (25.3 mg, 76.4 µmol) was added and the resulting mixture was stirred for 15 minutes. The reaction was quenched with EtOAc and saturated NH₄Cl. The product was extracted and dried. AcOH was added and the product was purified by preparative HPLC to yield the title compound (5 mg). MS m/z [M+H]+ calc'd for $C_{23}H_{23}FN_2O_6$, 443.15; found 443.2.

5C: (2S,4R)-5-(5'-Chloro-2'-fluorobiphenyl-4-yl)-2-hydroxymethyl-2-methyl-4-[(2-oxo-2,3-dihydrooxazole-4-carbonyl)amino]pentanoic Acid

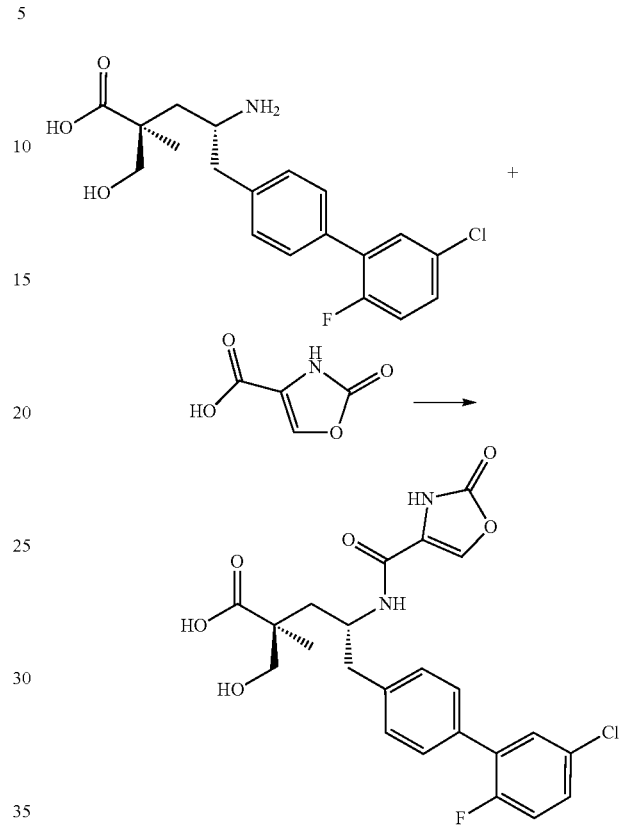

2-Oxo-2,3-dihydrooxazole-4-carboxylic acid (7 mg, 55 µmol) and HATU (20.8 mg, 55 µmol) were combined in DMF (0.2 mL) and allowed to stand at room temperature for 10 minutes. (2S,4R)-4-Amino-5-(5'-chloro-2'-fluorobiphenyl-4-yl)-2-hydroxymethyl-2-methylpentanoic acid (20 mg, 55 µmol) in DMF and DIPEA (28.6 µL, 164 µmol) were added, and the resulting mixture was stirred for 20 minutes at room temperature. The mixture was concentrated under reduced pressure and the residue was dissolved in AcOH purified by preparative HPLC to yield the title compound (0.6 mg). MS m/z [M+H]+ calc'd for $C_{23}H_{22}ClFN_2O_6$, 477.12; found 477.2.

5D: (2S,4R)-5-(5'-Chloro-2'-fluorobiphenyl-4-yl)-2-hydroxymethyl-2-methyl-4-[(2-oxo-2,3-dihydrooxazole-5-carbonyl)amino]pentanoic Acid

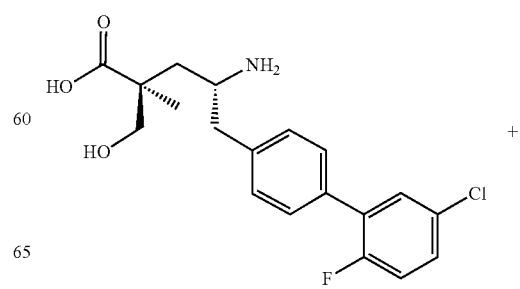

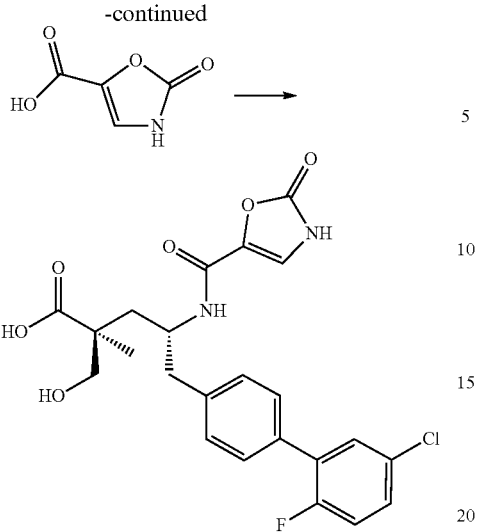

2-Oxo-2,3-dihydrooxazole-5-carboxylic acid (7.1 mg, 55 µmol) and HATU (21 mg, 55 µmol) were combined in DMF (0.3 mL) and stirred at room temperature for 5 minutes. (2S,4R)-4-Amino-5-(5'-chloro-2'-fluorobiphenyl-4-yl)-2-hydroxymethyl-2-methylpentanoic acid (20 mg, 55 µmol) in DMF (0.5 mL) and DIPEA (29 µL, 164 µmol) were added, and the resulting mixture was stirred for 10 minutes at room temperature. The mixture was concentrated under reduced pressure and the residue was dissolved in AcOH purified by preparative HPLC to yield the title compound (3 mg). MS m/z [M+H]±calc'd for $C_{23}H_{22}ClFN_2O_6$, 477.12; found 477.

Example 6

6A: (2S,4R)-5-(3'-Chlorobiphenyl-4-yl)-2-hydroxymethyl-4-[(3-methoxyisoxazole-5-carbonyl)amino]-2-methylpentanoic Acid

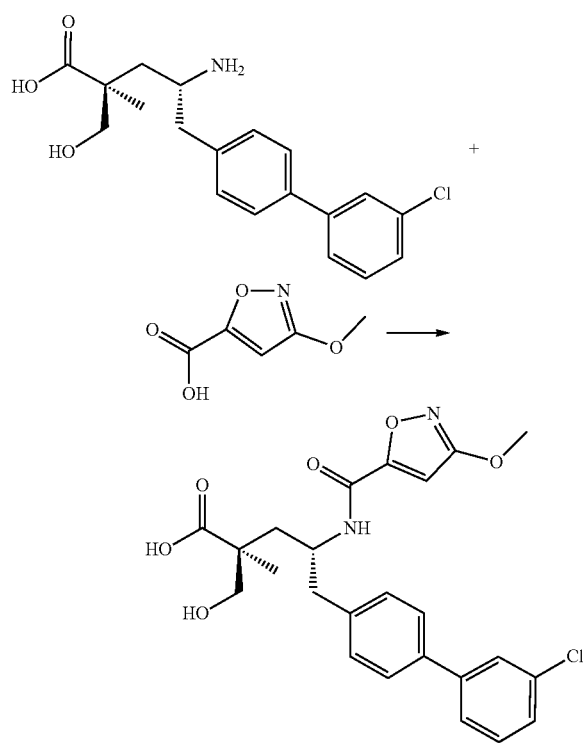

3-Methoxyisoxazole-5-carboxylic acid (9 mg, 32 µmol) was combined with HATU (12 mg, 32 µmol) and DMF (0.2 mL) and the resulting mixture was stirred for 5 minutes. DIPEA (17 µL, 96 µmol) and (2S,4R)-4-amino-5-(3'-chlorobiphenyl-4-yl)-2-hydroxymethyl-2-methylpentanoic acid (79 mg, 38 µmol) pre-dissolved in DMF were added and the resulting mixture was stirred for 15 minutes then concentrated. The residue was dissolved in AcOH and purified by preparative HPLC to yield the title compound (2.2 mg). MS m/z [M+H]⁺ calc'd for $C_{24}H_{25}ClN_2O_6$, 473.14; found 473.2.

6B: (2S,4R)-5-(3'-Chlorobiphenyl-4-yl)-4-[(3-methoxyisoxazole-5-carbonyl)amino]-2-methoxymethyl-2-methylpentanoic Acid

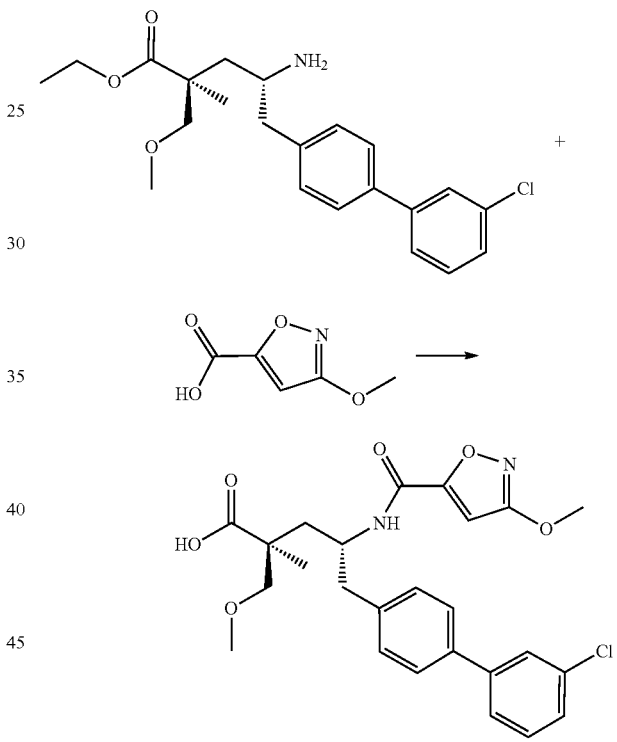

3-Methoxyisoxazole-5-carboxylic acid (4.4 mg, 31 µmol) and HATU (12 mg, 31 µmol) were combined in DMF (0.5 mL) and stirred for 5 minutes. A solution of (2S,4R)-4-amino-5-(3'-chlorobiphenyl-4-yl)-2-methoxymethyl-2-methylpentanoic acid ethyl ester (12 mg, 31 µmol) and DIPEA (16 µL, 93 µmol) in DMF (0.5 mL) was added and the resulting mixture was stirred for 20 minutes then concentrated under reduced pressure.

The residue was combined with THF (0.6 mL) and NaOH (124 µL, 124 µmol) and stirred at 60° C. for 2 hours, then concentrated under reduced pressure. The residue was dissolved in AcOH and compounds was purified by preparative HPLC to yield the title compound (1 mg). MS m/z [M+H]⁺ calc'd for $C_{25}H_{27}ClN_2O_6$, 487.16; found 487.2.

6C: (2S,4R)-5-(3'-Chlorobiphenyl-4-yl)-2-ethoxymethyl-4-[(3-methoxyisoxazole-5-carbonyl)amino]-2-methylpentanoic Acid

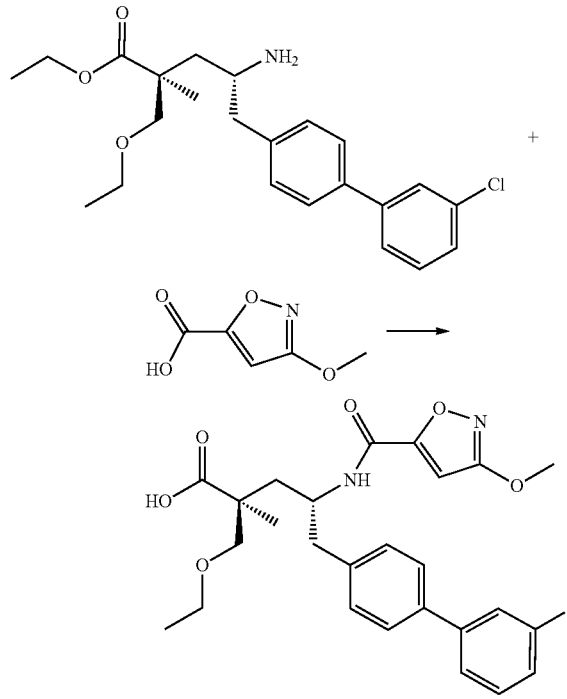

3-Methoxyisoxazole-5-carboxylic acid and (2S,4R)-4-amino-5-(3'-chlorobiphenyl-4-yl)-2-ethoxymethyl-2-methylpentanoic acid were reacted as described herein to yield the title compound (2 mg). MS m/z [M+H]±calc'd for $C_{26}H_{29}ClN_2O_6$, 501.17; found 501.2.

6D: (2S,4R)-5-Biphenyl-4-yl-4-[(3-hydroxyisoxazole-5-carbonyl)amino]-2-hydroxymethyl-2-methylpentanoic Acid

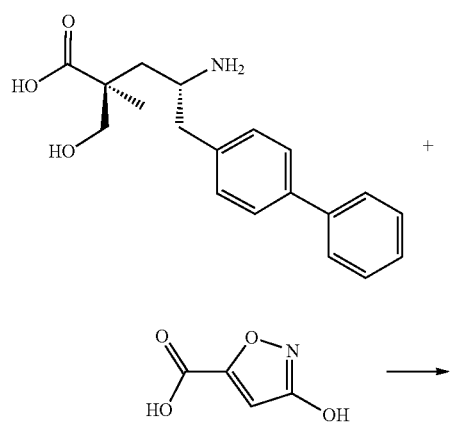

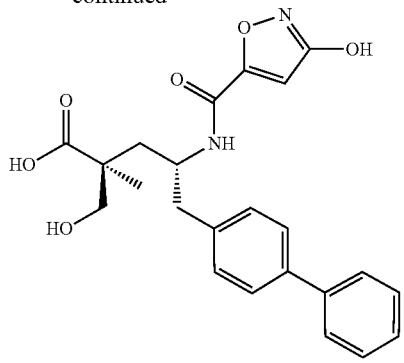

3-Hydroxy-isoxazole-5-carboxylic acid (10.6 mg, 82 μmol), EDC (14.5 μL, 82 μmol), and HOBt (11.1 mg, 82 μmol) were combined in DMF (0.2 mL) and stirred for 5 minutes. (2S,4R)-4-Amino-5-biphenyl-4-yl-2-hydroxymethyl-2-methylpentanoic acid (26 mg, 82 μmol) was added and the resulting mixture was stirred for 18 hours. The reaction was quenched with AcOH and the product was purified by preparative HPLC then lyophilized to yield the title compound as a TFA salt (7 mg). MS m/z [M+H]⁺ calc'd for $C_{23}H_{24}N_2O_6$, 425.16; found 425.4.

6E: (2S,4R)-5-Biphenyl-4-yl-4-[(3-hydroxyisoxazole-5-carbonyl)amino]-2-methoxymethyl-2-methylpentanoic Acid

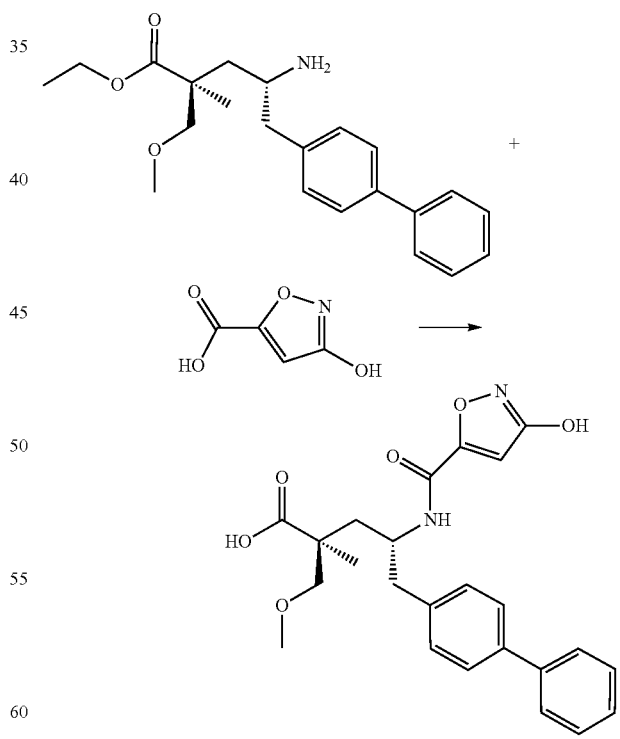

3-Hydroxy-isoxazole-5-carboxylic acid and (2S,4R)-4-amino-5-biphenyl-4-yl-2-methoxymethyl-2-methylpentanoic acid ethyl ester were reacted as described herein to yield the title compound (2.4 mg). MS m/z [M+H]⁺ calc'd for $C_{24}H_{26}N_2O_6$, 439.18; found 439.2.

6F: (2S,4R)-5-Biphenyl-4-yl-4-[(3-methoxyisoxazole-5-carbonyl)amino]-2-methoxymethyl-2-methylpentanoic Acid

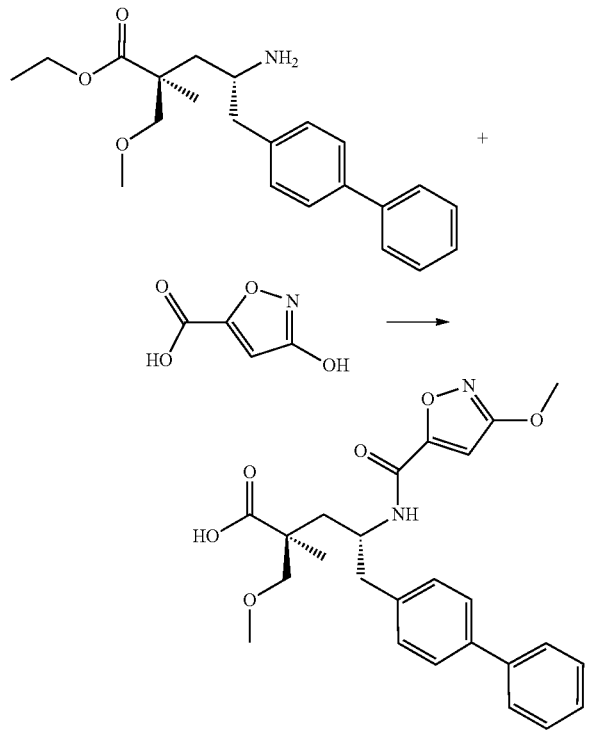

3-Methoxyisoxazole-5-carboxylic acid (4.4 mg, 31 µmol) and HATU (12 mg, 31 µmol) were combined in DMF (0.5 mL) and stirred for 5 minutes. A solution of (2S,4R)-4-amino-5-biphenyl-4-yl-2-methoxymethyl-2-methylpentanoic acid ethyl ester (11 mg, 31 µmol) and DIPEA (16 µL, 93 µmol) in DMF (0.5 mL) was added and the resulting mixture was stirred for 20 minutes then concentrated under reduced pressure.

The residue was combined with THF (0.6 mL) and NaOH (124 µL, 124 µmol) and stirred at 60° C. for 2 hours, then concentrated under reduced pressure. The residue was dissolved in AcOH and compounds was purified by preparative HPLC to yield the title compound (1 mg). MS m/z [M+H]+ calc'd for $C_{25}H_{28}N_2O_6$, 453.19; found 453.

6G: (2S,4R)-5-(5'-Chloro-2'-fluorobiphenyl-4-yl)-2-hydroxymethyl-4-[(3-methoxyisoxazole-5-carbonyl)amino]-2-methylpentanoic Acid

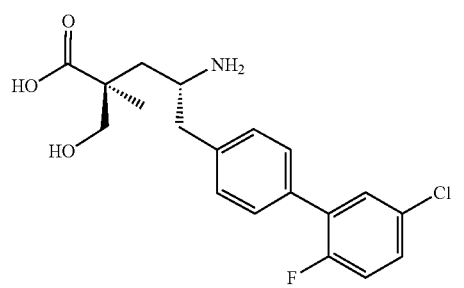

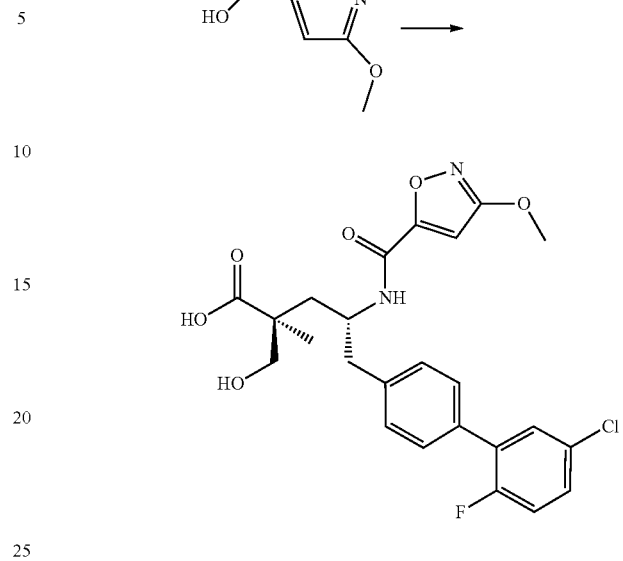

3-Methoxyisoxazole-5-carboxylic acid (8 mg, 55 µmol) and HATU (20.8 mg, 55 µmol) were combined in DMF (0.2 mL) and allowed to stand at room temperature for 10 minutes. (2S,4R)-4-Amino-5-(5'-chloro-2'-fluorobiphenyl-4-yl)-2-hydroxymethyl-2-methylpentanoic acid (20 mg, 55 µmol) in DMF and DIPEA (28.6 µL, 164 µmol) were added, and the resulting mixture was stirred for 20 minutes at room temperature. The mixture was concentrated under reduced pressure and the residue was dissolved in AcOH purified by preparative HPLC to yield the title compound (5.4 mg). MS m/z [M+H]+ calc'd for $C_{24}H_{24}ClFN_2O_6$, 491.13; found 491.2.

6H: (2S,4R)-5-(5'-Chloro-2'-fluorobiphenyl-4-yl)-4-[(3-ethylisoxazole-5-carbonyl)amino]-2-hydroxymethyl-2-methylpentanoic Acid

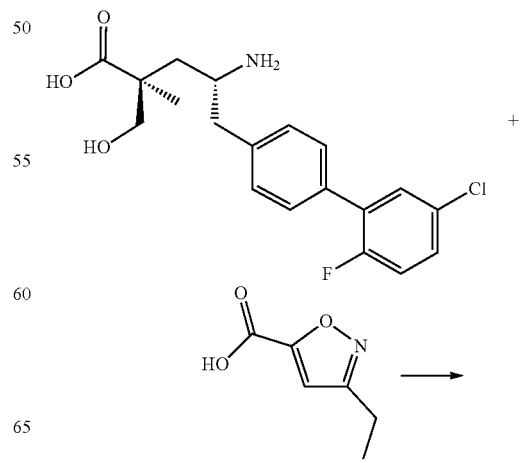

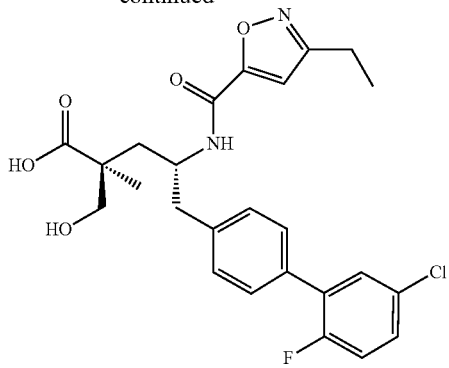

3-Ethylisoxazole-5-carboxylic acid (8 mg, 55 μmol) and HATU (20.8 mg, 55 μmol) were combined in DMF (0.2 mL) and allowed to stand at room temperature for 10 minutes. (2S,4R)-4-Amino-5-(5'-chloro-2'-fluorobiphenyl-4-yl)-2-hydroxymethyl-2-methylpentanoic acid (20 mg, 55 μmol) in DMF and DIPEA (28.6 μL, 164 μmol) were added, and the resulting mixture was stirred for 20 minutes at room temperature. The mixture was concentrated under reduced pressure and the residue was dissolved in AcOH purified by preparative HPLC to yield the title compound (3.6 mg). MS m/z [M+H]$^+$ calc'd for $C_{25}H_{26}ClFN_2O_5$, 489.15; found 490.2.

6I: (2S,4R)-5-(5'-Chloro-2'-fluorobiphenyl-4-yl)-2-hydroxymethyl-4-[(3-isobutylisoxazole-5-carbonyl)amino]-2-methylpentanoic Acid

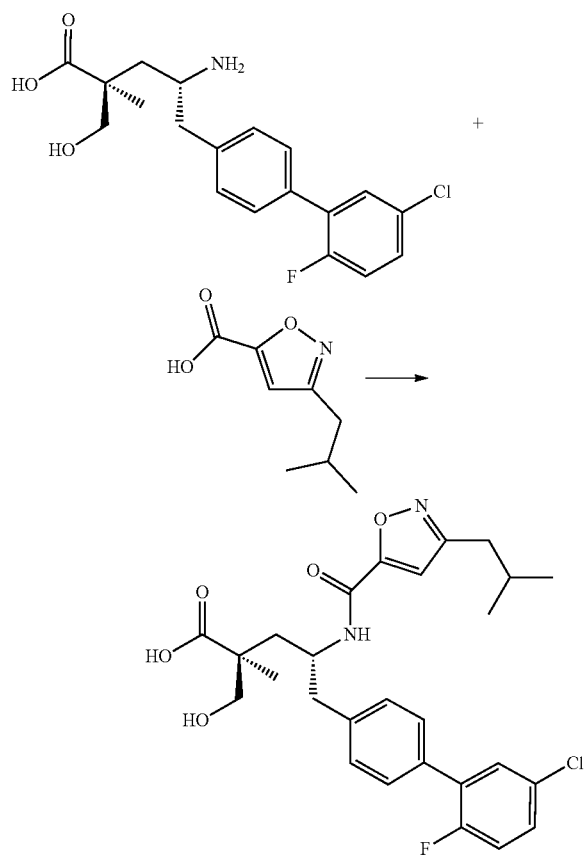

3-Isobutylisoxazole-5-carboxylic acid (9 mg, 55 μmol) and HATU (20.8 mg, 55 μmol) were combined in DMF (0.2 mL) and allowed to stand at room temperature for 10 minutes. (2S,4R)-4-Amino-5-(5'-chloro-2'-fluorobiphenyl-4-yl)-2-hydroxymethyl-2-methylpentanoic acid (20 mg, 55 μmol) in DMF and DIPEA (28.6 μL, 164 μmol) were added, and the resulting mixture was stirred for 20 minutes at room temperature. The mixture was concentrated under reduced pressure and the residue was dissolved in AcOH purified by preparative HPLC to yield the title compound (0.3 mg). MS m/z [M+H]$^+$ calc'd for $C_{27}H_{30}ClFN_2O_5$, 517.18; found 517.2.

6J: (2S,4R)-5-(5'-Chloro-2'-fluorobiphenyl-4-yl)-2-hydroxymethyl-2-methyl-4-[(3-propylisoxazole-5-carbonyl)amino]pentanoic Acid

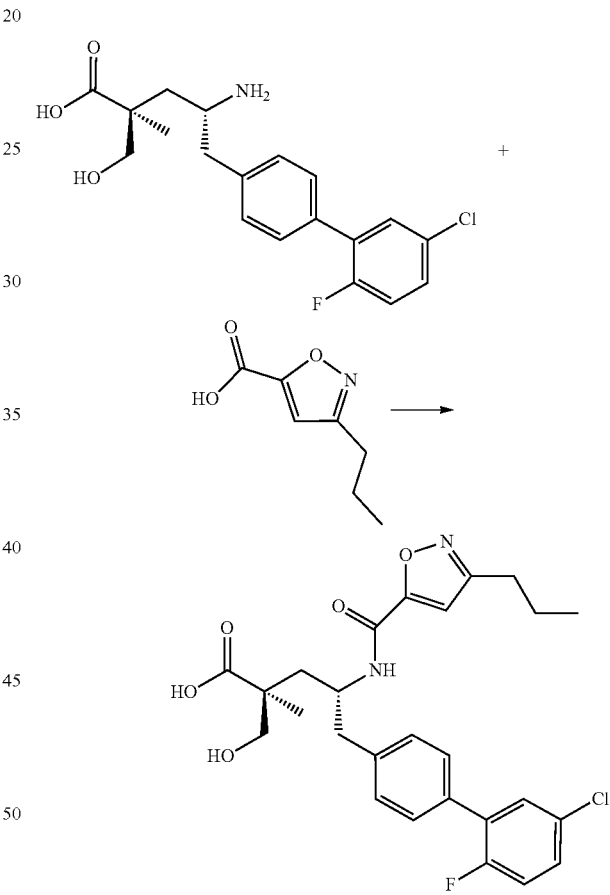

3-Propylisoxazole-5-carboxylic acid (9 mg, 55 μmol) and HATU (20.8 mg, 55 μmol) were combined in DMF (0.2 mL) and allowed to stand at room temperature for 10 minutes. (2S,4R)-4-Amino-5-(5'-chloro-2'-fluorobiphenyl-4-yl)-2-hydroxymethyl-2-methylpentanoic acid (20 mg, 55 μmol) in DMF and DIPEA (28.6 μL, 164 μmol) were added, and the resulting mixture was stirred for 20 minutes at room temperature. The mixture was concentrated under reduced pressure and the residue was dissolved in AcOH purified by preparative HPLC to yield the title compound (0.5 mg). MS m/z [M+H]$^+$ calc'd for $C_{26}H_{28}ClFN_2O_5$, 503.17; found 504.2.

6K: (2S,4R)-5-(5'-Chloro-2'-fluorobiphenyl-4-yl)-4-[(3-hydroxyisoxazole-5-carbonyl)amino]-2-methoxymethyl-2-methylpentanoic Acid

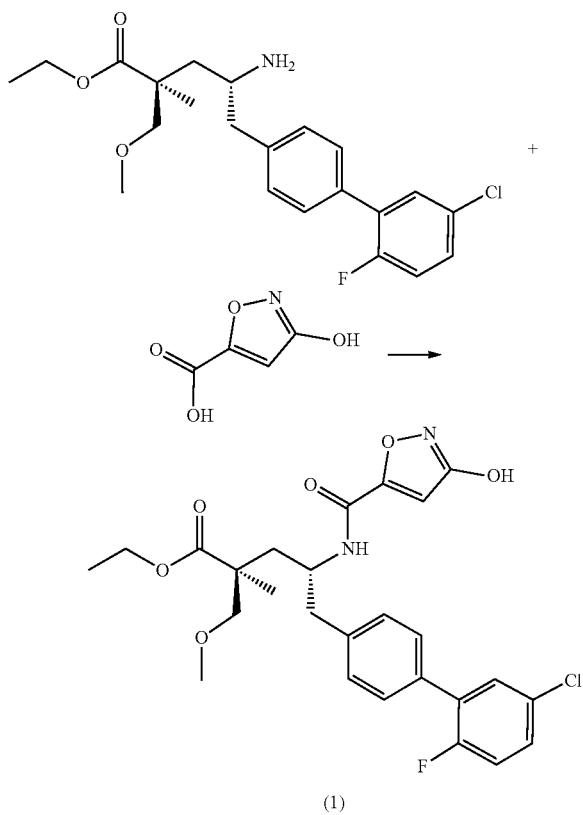

3-Hydroxy-isoxazole-5-carboxylic acid (4 rig, 0.03 µmol) and HATU (11 rig, 0.03 µmol) were combined with (2S,4R)-4-amino-5-(5'-chloro-2'-fluorobiphenyl-4-yl)-2-methoxymethyl-2-methylpentanoic acid ethyl ester (10 rig, 0.03 µmol) in DMF (0.5 mL) and stirred for 5 minutes. DIPEA (0.01 µL, 0.07 µmol) was added, and the resulting mixture was stirred 20 min and evaporated to yield crude Compound 1, which was used directly in the next step.

Compound 1 (10 mg) in THF (1 mL) was combined with 1N NaOH (0.3 mL) and the resulting mixture was stirred at 60° C. for 3 hours. AcOH was added and the product was purified (reverse phase) to yield the title compound (1 mg). MS m/z [M+H]$^+$ calc'd for $C_{24}H_{24}ClFN_2O_6$, 491.13; found 491.

6L: (2S,4R)-5-(3'-Chlorobiphenyl-4-yl)-2-(2-hydroxyethoxymethyl)-4-[(3-hydroxyisoxazole-5-carbonyl)amino]-2-methylpentanoic Acid

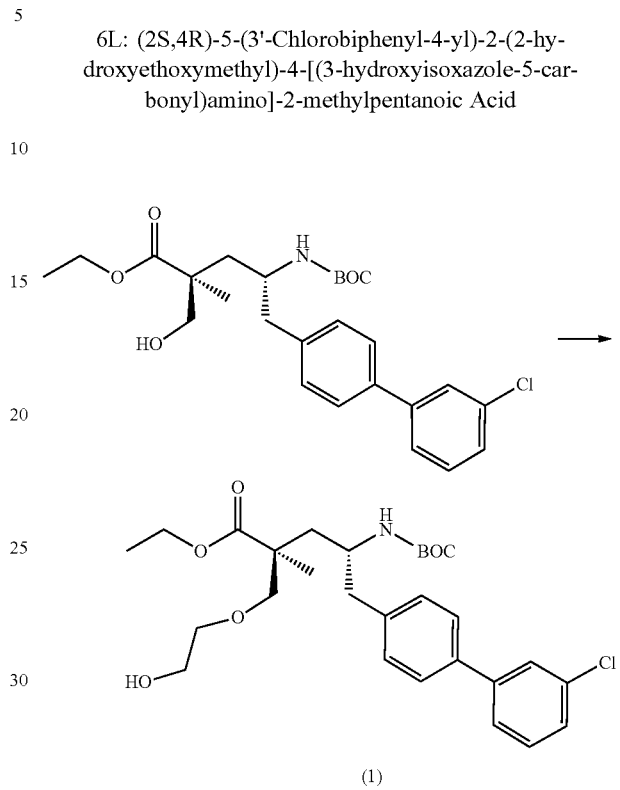

(2S,4R)-4-t-Butoxycarbonylamino-5-(3'-chlorobiphenyl-4-yl)-2-hydroxymethyl-2-methylpentanoic acid ethyl ester (415 mg, 840 µmol) and tetrabutylammonium hydrogen sulfate (57 mg, 168 µmol) were combined with DCM (1 mL) and NaOH (588 µL, 5.9 mmol). [1,3,2]Dioxathiolane 2,2-dioxide (424 mg, 3.4 mmol) was added and the reaction vessel was sealed and stirred vigorously overnight. The mixture was extracted with DCM and water then purified (normal phase chromatography 0-60% EtOAc to hexanes) to yield Compound 1 (90 mg).

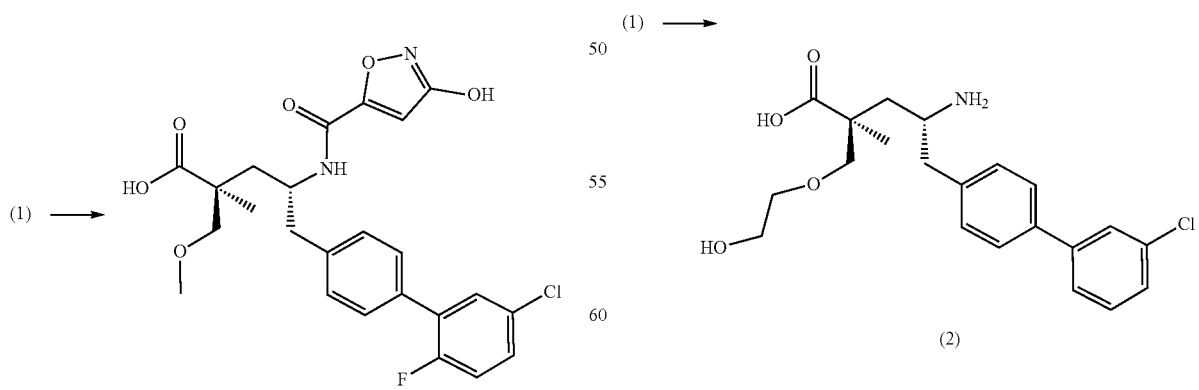

Compound 1 (90 mg, 173 µmol) was combined with MeCN (1 mL) and 4N HCl in dioxane (0.3 mL) and stirred for 10 minutes, then concentrated under reduced pressure to yield Compound (2).

(2) ⟶

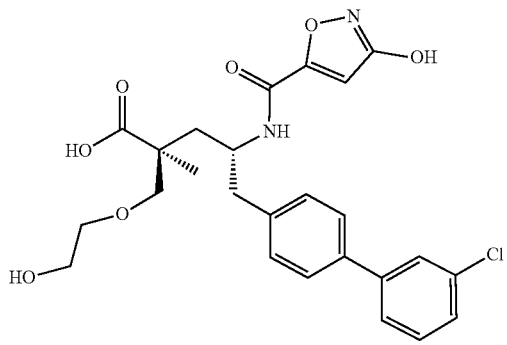

Compound 2 (35 mg, 83 µmol), HATU (38.0 mg, 100 µmol), 3-Hydroxy-isoxazole-5-carboxylic acid (12.3 mg, 108 µmol) and DMF (0.5 mL) were combined, followed by DIPEA (43.7 µL, 250 µmol). The resulting mixture was stirred for 2 hours. EtOAc was added, then saturated aqueous NH₄Cl. The mixture was then concentrated under reduced pressure. The residue was combined with THF (0.6 mL) and NaOH (326 µL, 326 µmol) with a few drop of MeOH, and stirred at 60° C. for 2 hours. The mixture was then concentrated under reduced pressure. The residue was dissolved in AcOH and purified by preparative HPLC to yield the title compound (8 mg). MS m/z [M+H]⁺ calc'd for $C_{25}H_{27}ClN_2O_7$, 503.15; found 503.

6M: (2S,4R)-5-(3'-Chlorobiphenyl-4-yl)-2-ethoxymethyl-4-[(3-hydroxyisoxazole-5-carbonyl)amino]-2-methylpentanoic Acid

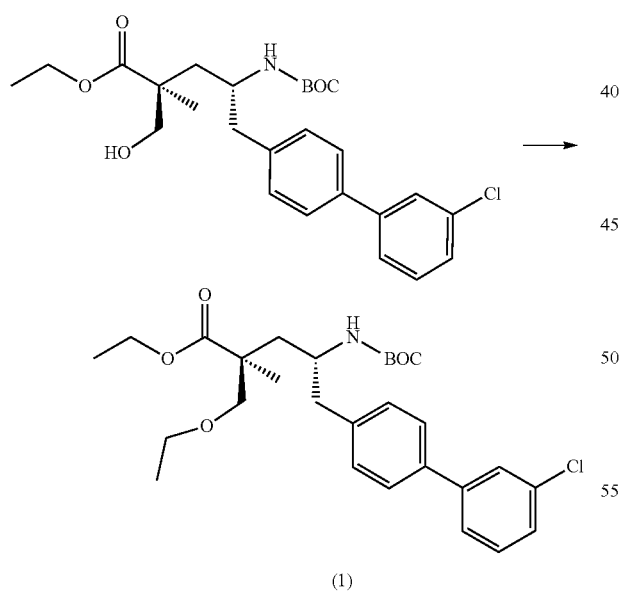

(1)

(2S,4R)-4-t-Butoxycarbonylamino-5-(3'-chlorobiphenyl-4-yl)-2-hydroxymethyl-2-methylpentanoic acid ethyl ester (415 mg, 840 µmol) and tetrabutylammonium hydrogen sulfate (57 mg, 168 µmol) were combined with DCM (1 mL) and NaOH (588 µL, 5.9 mmol). Diethylsulfate (518 mg, 3.4 mmol) was added and the reaction vessel was sealed and stirred vigorously overnight. The mixture was extracted with DCM and water then purified (normal phase chromatography 0-60% EtOAc to hexanes) to yield Compound 1 (180 mg).

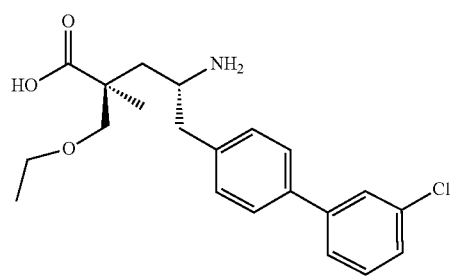

(1)

Compound 1 (87 mg, '73 µmol) was combined with MeCN (1 mL) and 4N HCl in dioxane (0.3 mL) and stirred for 10 minutes, then concentrated under reduced pressure to yield Compound (2).

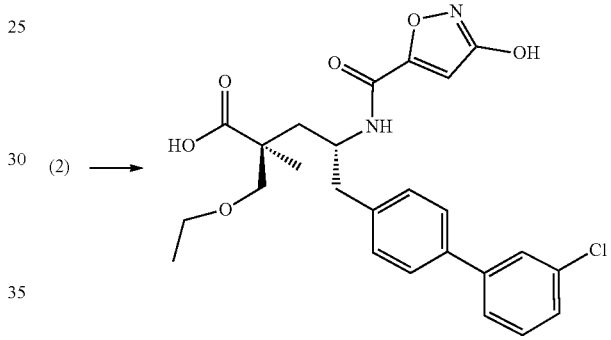

(2) ⟶

Compound 2 (33.7 mg, 83 µmol), HATU (38.0 mg, 100 µmol), 3-Hydroxy-isoxazole-5-carboxylic acid (12.3 mg, 108 µmol) and DMF (0.5 mL) were combined, followed by DIPEA (43.7 µL, 250 µmol). The resulting mixture was stirred for 2 hours. EtOAc was added, then saturated aqueous NH₄Cl. The mixture was then concentrated under reduced pressure. The residue was combined with THF (0.6 mL) and NaOH (326 µL, 326 µmol) with a few drop of MeOH, and stirred at 60° C. for 2 hours. The mixture was then concentrated under reduced pressure. The residue was dissolved in AcOH and purified by preparative HPLC to yield the title compound (8 mg). MS m/z [M+H]⁺ calc'd for $C_{25}H_{27}ClN_2O_6$, 487.16; found 486.9.

6N: (2S,4R)-5-(5'-Chloro-2'-fluorobiphenyl-4-yl)-2-ethoxymethyl-4-[(3-hydroxyisoxazole-5-carbonyl)amino]-2-methylpentanoic Acid

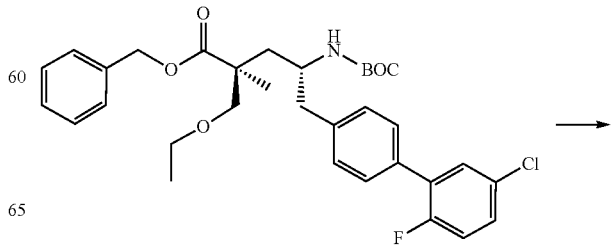

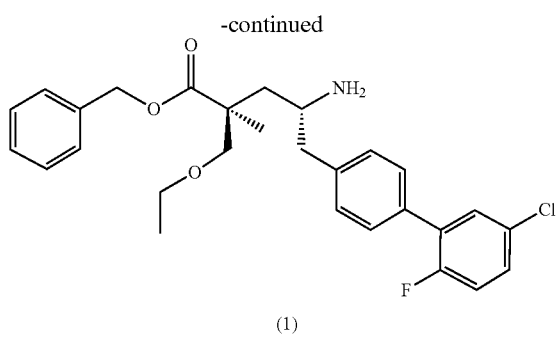

(1)

(2S,4R)-4-t-Butoxycarbonylamino-5-(5'-chloro-2'-fluorobiphenyl-4-yl)-2-ethoxymethyl-2-methylpentanoic acid benzyl ester (720 mg, 1.2 mmol) was combined with MeCN (6 mL), followed by the addition of 4N HCl in dioxane (5 mL). The resulting mixture was stirred for 10 minutes then concentrated under reduced pressure to yield Compound 1.

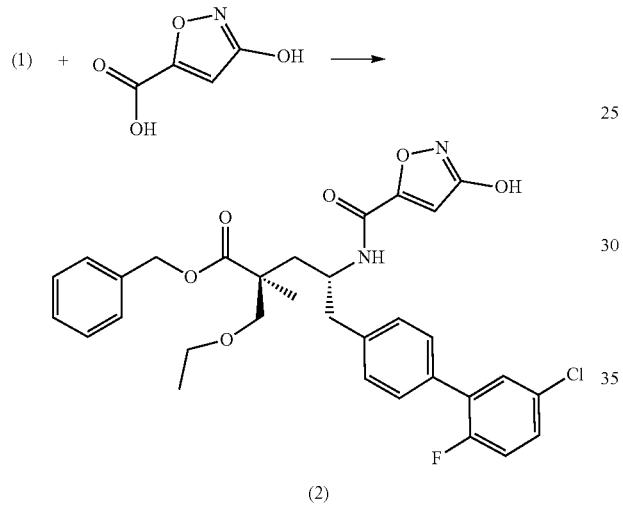

(2)

3-Hydroxyisoxazole-5-carboxylic acid (53.3 mg, 413 μmol) was combined with HATU (157 mg, 413 μmol) and DMF (0.5 mL mL) and the resulting mixture was stirred for 20 minutes. N-ethyl-N-isopropylpropan-2-amine (1 eq.) was added and the resulting mixture was stirred for 1 minute. Compound 1 (100 mg, 207 μmol) pre-dissolved in DMF (2 mL) and DIPEA (108 μl, 620 μmol) was then added and the resulting mixture was stirred overnight then concentrated under reduced pressure. The material was then purified by normal phase (40% EtOAc/hexanes) to yield Compound 2 (90 mg).

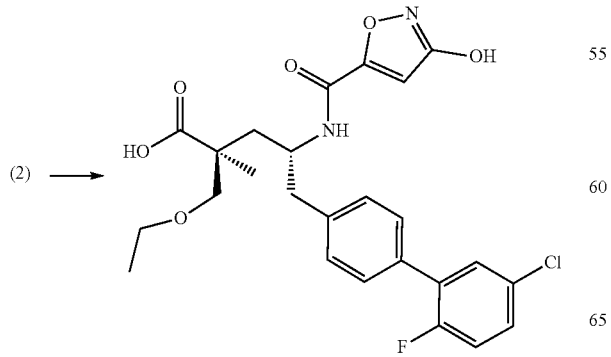

Compound 2 (90 mg, 151 μmol) was combined with palladium on carbon (16.1 mg, 30 μmol) dissolved in EtOAc (1 mL) and AcOH (1 mL). The resulting solution was degassed in vacuo and purged with hydrogen gas. The solution was stirred for 2 hours. The hydrogen gas was removed and the solution was purged with nitrogen. The solution was filtered, the excess solvent was removed from the filtrate and the residue was purified by reverse phase chromatography to yield the title compound (60 mg). MS m/z [M+H]$^+$ calc'd for $C_{25}H_{26}ClFN_2O_6$, 505.15; found 505.

6O: (2S,4R)-5-(5'-Chloro-2'-fluorobiphenyl-4-yl)-2-ethoxymethyl-4-[(3-ethylisoxazole-5-carbonyl)amino]-2-methylpentanoic Acid

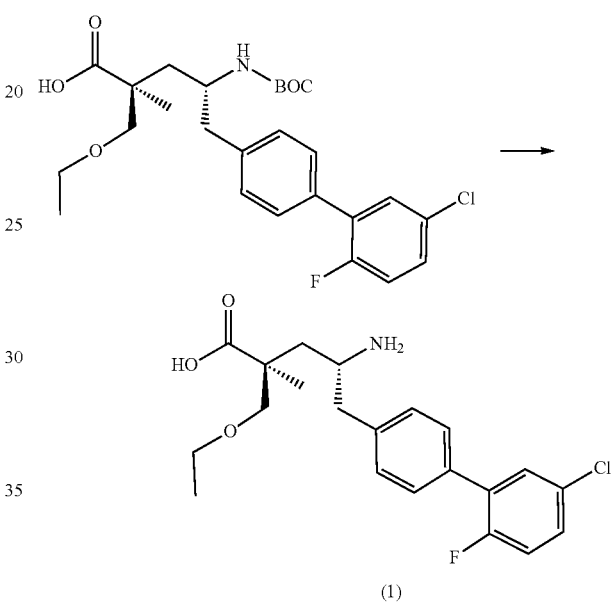

(1)

(2S,4R)-4-t-Butoxycarbonylamino-5-(5'-chloro-2'-fluorobiphenyl-4-yl)-2-ethoxymethyl-2-methylpentanoic acid (220 mg, 445 μmol) was combined with MeCN (5 mL), followed by the addition of 4N HCl in dioxane (4 mL). The resulting mixture was stirred for 10 minutes then concentrated under reduced pressure to yield Compound 1.

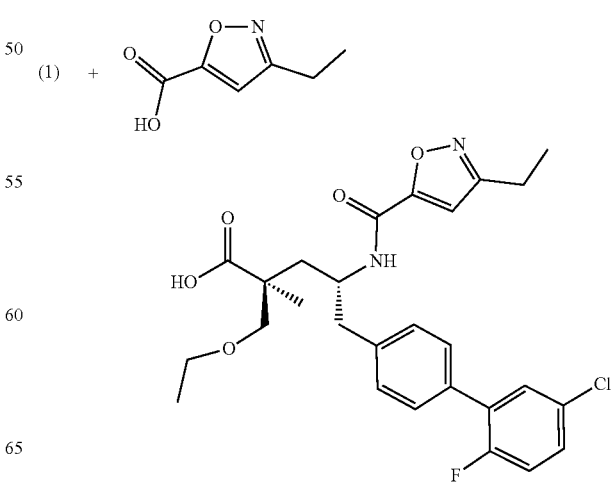

3-Ethylisoxazole-5-carboxylic acid (6.0 mg, 42 µmol) was combined with HATU (16.1 mg, 42 µmol) and DMF (0.5 mL) and the resulting mixture was stirred for 10 minutes. N-ethyl-N-isopropylpropan-2-amine (1 eq.) was added and the resulting mixture was stirred for 1 minute. Compound 1 (20 mg, 51 µmol) pre-dissolved in DMF (0.5 mL) and DIPEA (22.2 µL, 127 µmol) was then added the resulting mixture was stirred for 30 minutes. The mixture was then concentrated under reduced pressure, removing about half of the solvent. AcOH was added to the residue, and the material was purified by preparative HPLC to yield the title compound (2.5 mg). MS m/z [M+H]$^+$ calc'd for $C_{27}H_{30}ClFN_2O_5$, 517.18; found 518.2.

Following the procedures described in the previous examples, and substituting the appropriate starting materials and reagents, the following compounds can also be prepared.

6P: (2S,4R)-5-(5'-Chloro-2'-fluorobiphenyl-4-yl)-4-[(3-hydroxyisoxazole-5-carbonyl)amino]-2-hydroxymethyl-2-methylpentanoic Acid

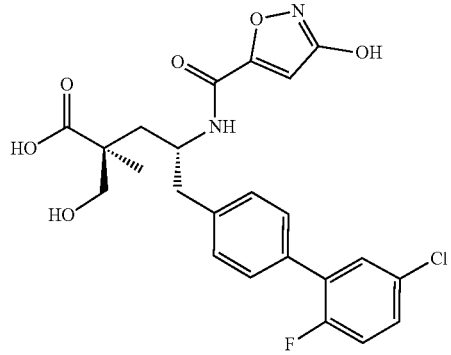 [SMILES: C[C@@](CO)(C[C@@H](Cc1ccc(-c2cc(Cl)ccc2F)cc1)NC(=O)c1cc(O)no1)C(=O)O]

6Q: (2S,4R)-5-(5'-Chloro-2'-fluorobiphenyl-4-yl)-4-[(3-ethylisoxazole-5-carbonyl)amino]-2-methoxymethyl-2-methylpentanoic Acid

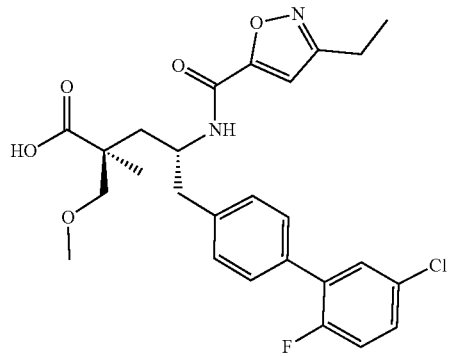 [SMILES: CCc1cc(C(=O)N[C@H](Cc2ccc(-c3cc(Cl)ccc3F)cc2)C[C@@](C)(COC)C(=O)O)on1]

Example 7

7A: (2S,4R)-5-(3'-Chlorobiphenyl-4-yl)-4-[(5-ethoxy-1H-pyrazole-3-carbonyl)amino]-2-hydroxymethyl-2-methylpentanoic Acid

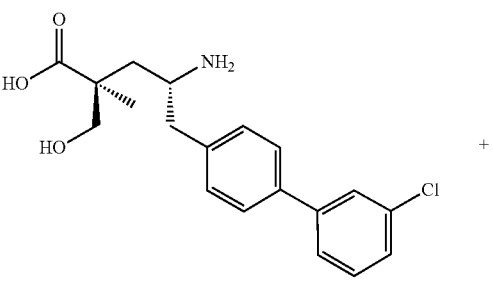

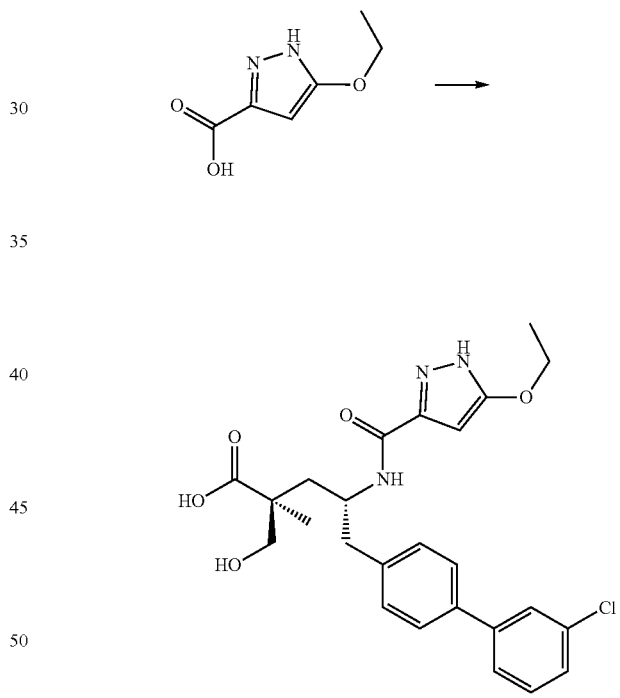

5-Ethoxy-1H-pyrazole-3-carboxylic acid (10 mg, 32 µmol) was combined with HATU (12 mg, 32 µmol) in DMF (0.2 mL) and the resulting mixture was stirred for 5 minutes. DIPEA (17 µL, 96 µmol) and (2S,4R)-4-amino-5-(3'-chlorobiphenyl-4-yl)-2-hydroxymethyl-2-methylpentanoic acid (79 mg, 38 µmol) pre-dissolved in DMF were added and the resulting mixture was stirred for 15 minutes then concentrated. The residue was dissolved in AcOH and purified by preparative HPLC to yield the title compound as a TFA salt (1 mg). MS m/z [M+H]$^+$ calc'd for $C_{25}H_{28}ClN_3O_5$, 486.17; found 486.2.

7B: (2S,4R)-5-(5'-Chloro-2'-fluorobiphenyl-4-yl)-4-[(5-ethoxy-H-pyrazole-3-carbonyl)-amino]-2-hydroxymethyl-2-methylpentanoic Acid

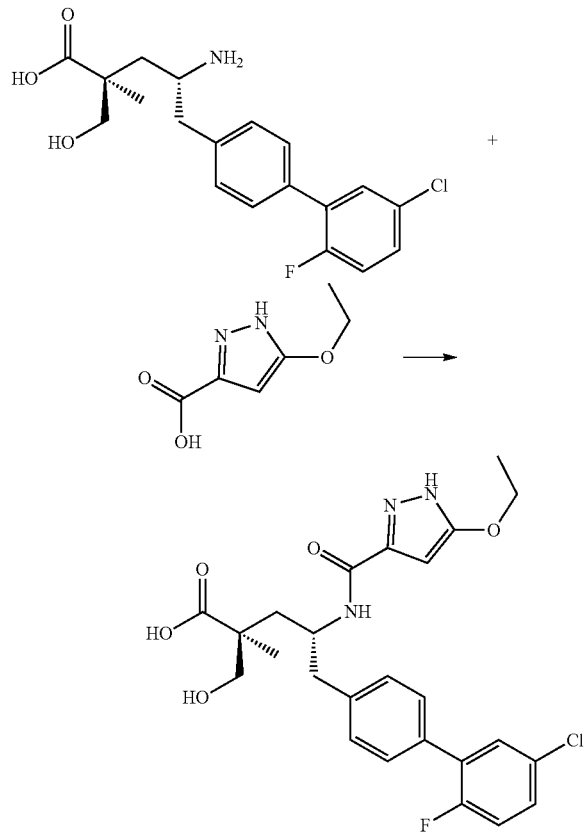

5-Ethoxy-1H-pyrazole-3-carboxylic acid (8.5 mg, 55 μmol) was combined with HATU (21 mg, 55 μmol) in DMF (0.3 mL) and the resulting mixture was stirred for 5 minutes. DIPEA (29 μL, 164 μmol) and (2S,4R)-4-amino-5-(5'-chloro-2'-fluorobiphenyl-4-yl)-2-hydroxymethyl-2-methylpentanoic acid (20 mg, 55 μmol) pre-dissolved in DMF (0.5 mL) were added and the resulting mixture was stirred for 10 minutes then concentrated. The residue was dissolved in AcOH and purified by preparative HPLC to yield the title compound as a TFA salt (2 mg). MS m/z [M+H]$^+$ calc'd for $C_{25}H_{27}ClFN_3O_5$, 504.16; found 503.9.

7C: (2S,4R)-5-(5'-Chloro-2'-fluoropheny-4-1)-2-hydroxymethyl-4-[(5-isopropyl-2H-pyrazole-3-carbonyl)amino]-2-methylpentanoic Acid

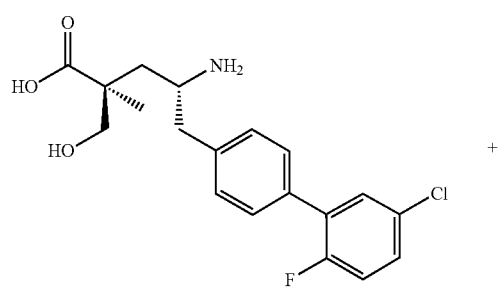

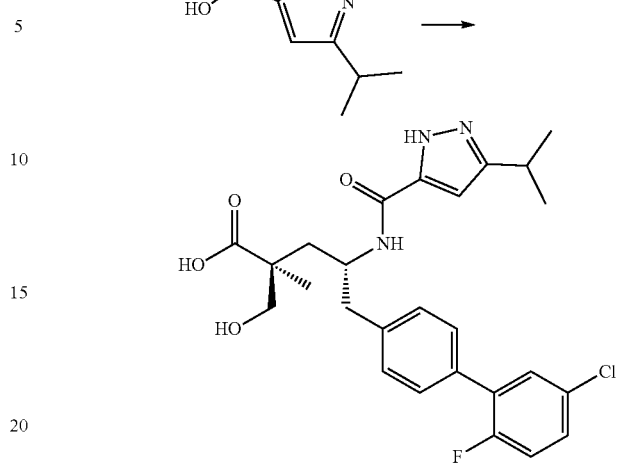

5-Isopropyl-2H-pyrazole-3-carboxylic acid (8 mg, 55 μmol) and HATU (20.8 mg, 55 μmol) were combined in DMF (0.2 mL) and allowed to stand at room temperature for 10 minutes. (2S,4R)-4-Amino-5-(5'-chloro-2'-fluorobiphenyl-4-yl)-2-hydroxymethyl-2-methylpentanoic acid (20 mg, 55 μmol) in DMF and DIPEA (28.6 μL, 164 μmol) were added, and the resulting mixture was stirred for 20 minutes at room temperature. The mixture was concentrated under reduced pressure and the residue was dissolved in AcOH and purified by preparative HPLC to yield the title compound as a TFA salt (2 mg). MS m/z [M+H]$^+$ calc'd for $C_{26}H_{29}ClFN_3O_4$, 502.18; found 503.2.

7D: (2S,4R)-5-(5'-Chloro-2'-fluorobiphenyl-4-yl)-4-[(5-ethoxy-2H-pyrazole-3-carbonyl)-amino]-2-methoxymethyl-2-methylpentanoic Acid

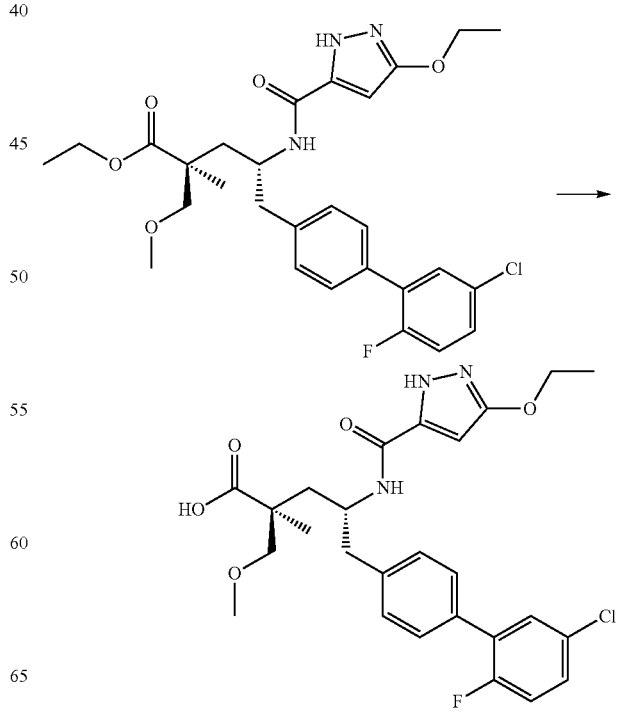

(2S,4R)-5-(5'-Chloro-2'-fluorobiphenyl-4-yl)-4-[(5-ethoxy-2H-pyrazole-3-carbonyl)amino]-2-methoxymethyl-2-methylpentanoic acid ethyl ester (11 mg) in THF (1 mL) was combined with 1N NaOH (0.3 mL) and the resulting mixture was stirred at 60° C. for 3 hours. AcOH was added and the product was purified (reverse phase) to yield the title compound as a TFA salt (4 mg). MS m/z [M+H]$^+$ calc'd for $C_{26}H_{29}ClFN_3O_5$, 518.18; found 518.

7E: (2S,4R)-5-(5'-Chloro-2'-fluorobiphenyl-4-yl)-2-hydroxymethyl-4-[(5-methoxy-1H-pyrazole-3-carbonyl)amino]-2-methylpentanoic Acid

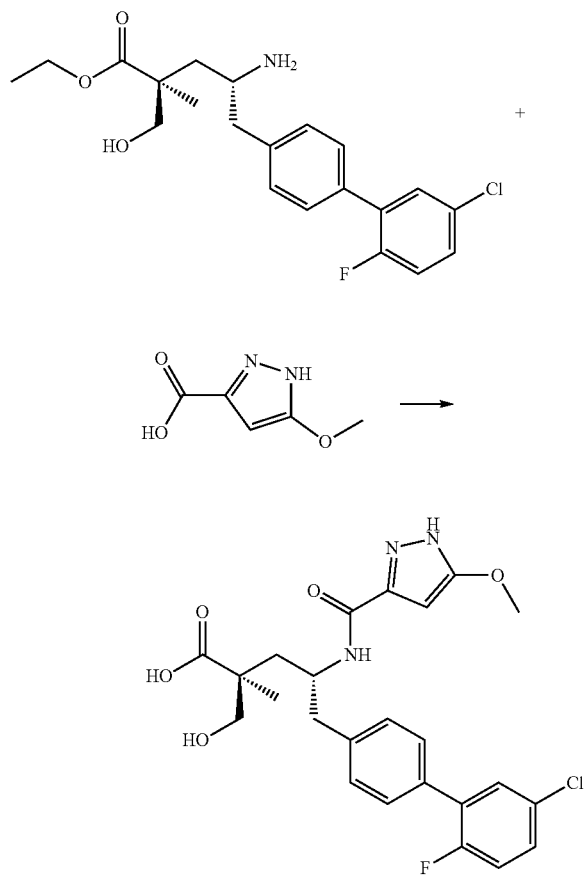

(2S,4R)-4-Amino-5-(5'-chloro-2'-fluorobiphenyl-4-yl)-2-hydroxymethyl-2-methylpentanoic acid ethyl ester (30 mg, 76 µmol), HATU (29.0 mg, 0.076 mmol), and DIPEA (39.9 µl, 0.228 mmol), were combined with 1 h-[1,2,4]triazole-3-carboxylic acid (8.61 mg, 0.076 mmol) in DMF (0.5 mL). The resulting mixture was stirred for 2 hours then concentrated under reduced pressure. The residue was combined with THF (1 mL) and NaOH (456 µL, 456 µmol) and stirred for 2 days at 40° C. The reaction was quenched with AcOH and the material was purified by preparative HPLC to yield the title compound as a TFA salt (16.4 mg). MS m/z [M+H]$^+$ calc'd for $C_{24}H_{25}ClFN_3O_5$, 490.15; found 490.2.

7F: (2S,4R)-5-(5'-Chloro-2'-fluorobiphenyl-4-yl)-2-hydroxymethyl-4-[(5-isobutyl-2H-pyrazole-3-carbonyl)amino]-2-methylpentanoic Acid

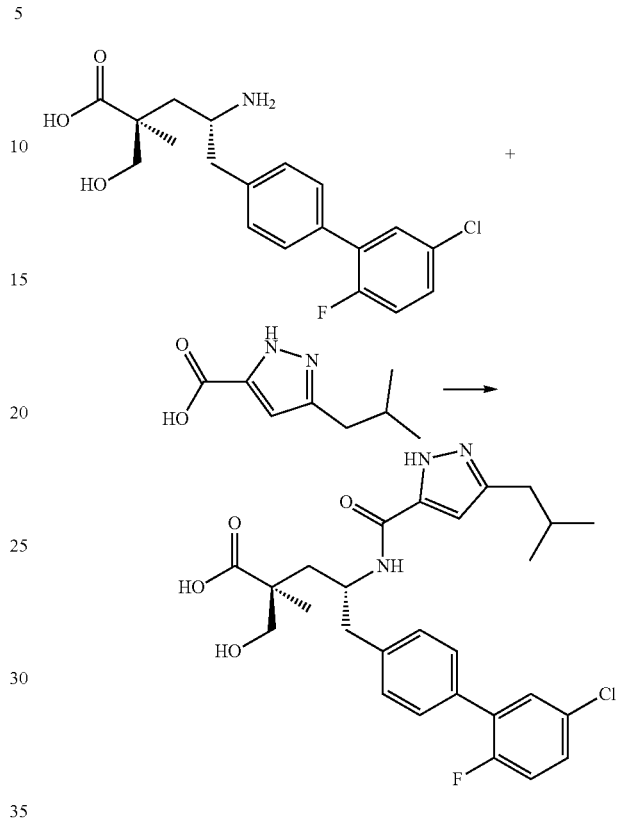

5-Isobutyl-2H-pyrazole-3-carboxylic acid (10.1 mg, 60 µmol) and HATU (22.9 mg, 60 µmol) were combined then stirred in DMF (1 mL) for 15 minutes at room temperature. (2S,4R)-4-Amino-5-(5'-chloro-2'-fluorobiphenyl-4-yl)-2-hydroxymethyl-2-methylpentanoic acid (20 mg, 55 µmol) and Et$_3$N (38 µL, 273 µmol) were premixed together and then added to the reaction solution. The resulting mixture was stirred for 1 hour at room temperature. The solvent was removed in vacuo and the residue was purified by preparative HPLC to yield the title compound as a TFA salt (13.3 mg). MS m/z [M+H]$^+$ calc'd for $C_{27}H_{31}ClFN_3O_4$, 516.20; found 516.2.

Example 8

8A: (2S,4R)-4-[(5-Acetyl-2H-pyrazole-3-carbonyl)amino]-5-(5'-chloro-2'-fluorobiphenyl-4-yl)-2-hydroxymethyl-2-methylpentanoic Acid

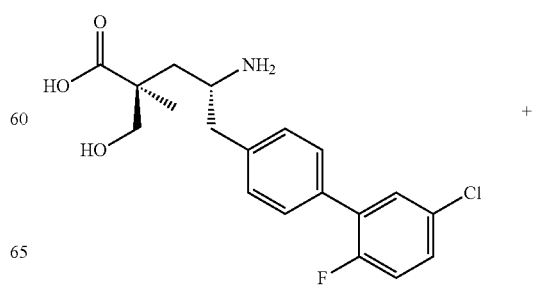

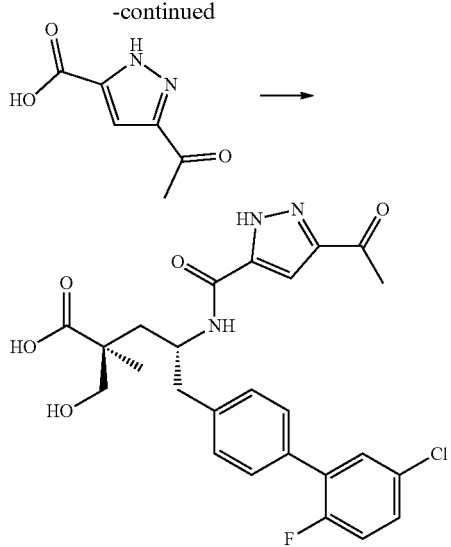

5-Acetyl-2H-pyrazole-3-carboxylic acid (8 mg, 55 µmol) and HATU (20.8 mg, 55 µmol) were combined in DMF (0.2 mL) and allowed to stand at room temperature for 10 minutes. (2S,4R)-4-Amino-5-(5'-chloro-2'-fluorobiphenyl-4-yl)-2-hydroxymethyl-2-methylpentanoic acid (20 mg, 55 µmol) in DMF and DIPEA (28.6 µL, 164 µmol) were added, and the resulting mixture was stirred for 20 minutes at room temperature. The mixture was concentrated under reduced pressure and the residue was dissolved in AcOH purified by preparative HPLC to yield the title compound as a TFA salt (2.1 mg). MS m/z [M+H]$^+$ calc'd for $C_{25}H_{25}ClFN_3O_5$, 502.15; found 503.2.

8B: (2S,4R)-4-[(5-Acetyl-2H-pyrazole-3-carbonyl)amino]-5-(5'-chloro-2'-fluorobiphenyl-4-yl)-2-methoxymethyl 1-2-methylpentanoic Acid

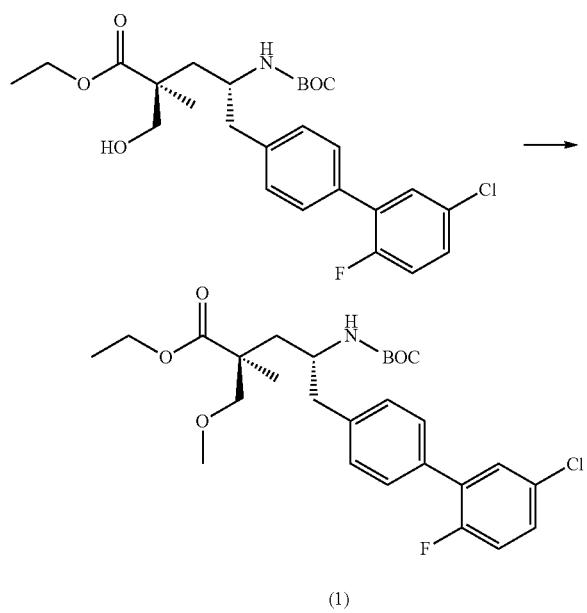

Into a vial was added (2S,4R)-4-t-butoxycarbonylamino-5-(5'-chloro-2'-fluoro-biphenyl-4-yl)-2-hydroxymethyl-2-methylpentanoic acid ethyl ester (415 mg, 840 µmol), tetrabutylammonium hydrogen sulfate (57 mg, 168 µmol), DCM (1 mL) and NaOH (588 µL, 5.9 mmol), followed by diethylsulfate (518 mg, 3.4 mmol). The reaction vessel was capped and stirred vigorously overnight. The mixture was extracted with DCM and water, purified (normal phase chromatography 0-60% EtOAc:hexanes), then concentrated under reduced pressure to yield Compound 1 (220 mg).

(1) ⟶

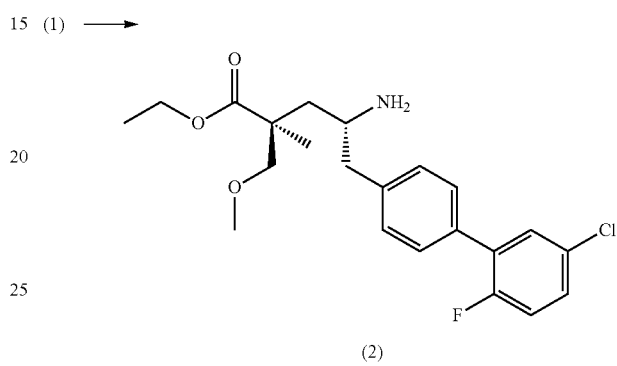

Compound 1 (88 mg, 173 µmol) in MeCN (1 mL) was combined with 4N HCl in dioxane (0.3 mL). The mixture was stirred for 10 minutes then concentrated under reduced pressure to yield Compound 2.

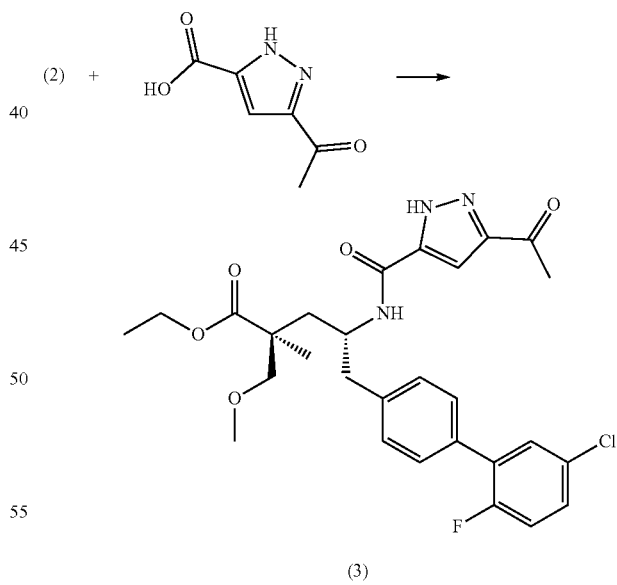

Compound 2 (10 µg, 0.03 µmol) in DMF (0.5 mL) was combined with HATU (11 µg, 0.03 µmol) and 5-acetyl-2H-pyrazole-3-carboxylic acid (4 µg, 0.03 µmol), and the resulting mixture was stirred for 5 minutes. DIPEA (0.01 µl, 0.07 µmol) was added and the mixture was stirred for 20 minutes. The solvent was evaporated to yield Compound 3, which was used without further purification.

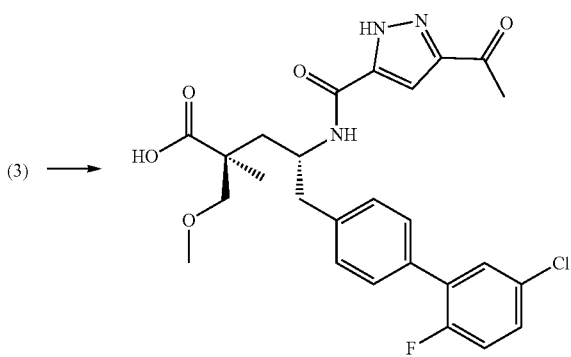 [SMILES: COC[C@](C)(C[C@@H](Cc1ccc(-c2cc(Cl)ccc2F)cc1)NC(=O)c1cc(C(C)=O)n[nH]1)C(=O)O]

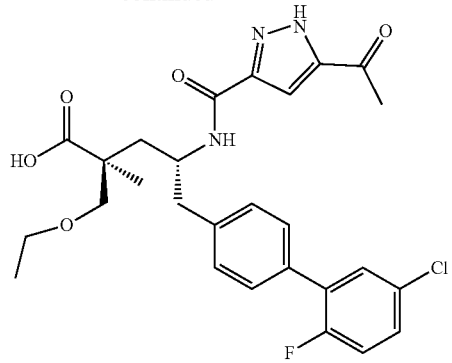

Compound 3 (11 mg, 20 µmol) was combined with THF (1 mL) and 1N NaOH (0.3 mL). The resulting mixture was stirred at 60° C. for 3 hours. AcOH was added and the product was purified by reverse phase HPLC to yield the title compound as a TFA salt (2 mg). MS m/z [M+H]$^+$ calc'd for $C_{26}H_{27}ClFN_3O_5$, 516.16; found 516.

8C: (2S,4R)-4-[(5-Acetyl-1H-pyrazole-3-carbonyl)amino]-5-(5'-chloro-2'-fluorobiphenyl-4-yl)-2-ethoxymethyl-2-methylpentanoic Acid

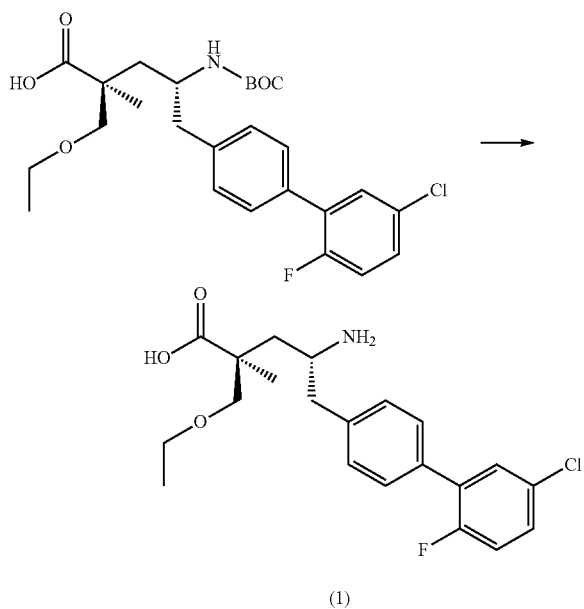

(2S,4R)-4-t-Butoxycarbonylamino-5-(5'-chloro-2'-fluorobiphenyl-4-yl)-2-ethoxymethyl-2-methylpentanoic acid (220 mg, 445 µmol) was combined with MeCN (5 mL), followed by the addition of 4N HCl in dioxane (4 mL). The resulting mixture was stirred for 10 minutes then concentrated under reduced pressure to yield Compound 1.

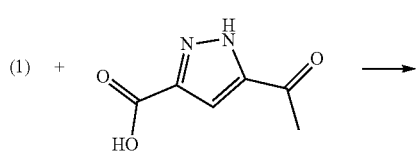

5-Acetyl-1H-pyrazole-3-carboxylic acid (6.5 mg, 42 µmol) was combined with HATU (16.1 mg, 42 µmol) and DMF (0.5 mL) and the resulting mixture was stirred for 10 minutes. N-ethyl-N-isopropylpropan-2-amine (1 eq.) was added and the resulting mixture was stirred for 1 minute. Compound 1 (20 mg, 51 µmol) pre-dissolved in DMF (0.5 mL) and DIPEA (22.2 µL, 127 µmol) was then added the resulting mixture was stirred for 30 minutes. The mixture was then concentrated under reduced pressure, removing about half of the solvent. AcOH was added to the residue, and the material was purified by preparative HPLC to yield the title compound as a TFA salt (3.1 mg). MS m/z [M+H]$^+$ calc'd for $C_{27}H_{29}ClFN_3O_5$, 530.18; found 531.2.

ASSAY

In vitro Assays for the Quantitation of Inhibitor Potencies (IC$_{50}$) at Human and Rat NEP, and Human ACE The inhibitory activities of compounds at human and rat neprilysin (EC 3.4.24.11; NEP) and human angiotensin converting enzyme (ACE) were determined using in vitro assays as described below.

Extraction of NEP Activity from Rat Kidneys

Rat NEP was prepared from the kidneys of adult Sprague Dawley rats. Whole kidneys were washed in cold phosphate buffered saline (PBS) and brought up in ice-cold lysis buffer (1% Triton X-114, 150 mM NaCl, 50 mM tris(hydroxymethyl) aminomethane (Tris) pH 7.5; Bordier (1981) *J. Biol. Chem.* 256: 1604-1607) in a ratio of 5 mL of buffer for every gram of kidney. Samples were homogenized on ice using a polytron hand held tissue grinder. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with bovine serum albumin (BSA) as a standard.

Enzyme Inhibition Assays

Recombinant human NEP and recombinant human ACE were obtained commercially (R&D Systems, Minneapolis, Minn., catalog numbers 1182-ZN and 929-ZN, respectively). The fluorogenic peptide substrate Mca-D-Arg-Arg-Leu-Dap-(Dnp)-OH (Medeiros et al. (1997) *Braz. J Med. Biol. Res*. 30:1157-62; Anaspec, San Jose, Calif.) and Abz-Phe-Arg-Lys(Dnp)-Pro-OH (Araujo et al. (2000) *Biochemistry* 39:8519-8525; Bachem, Torrance, Calif.) were used in the NEP and ACE assays respectively.

The assays were performed in 384-well white opaque plates at 37° C. using the fluorogenic peptide substrates at a concentration of 10 µM in Assay Buffer (NEP: 50 mM HEPES, pH 7.5, 100 mM NaCl, 0.01% polyethylene glycol sorbitan monolaurate (Tween-20), 10 µM $ZnSO_4$; ACE: 50 mM HEPES, pH 7.5, 100 mM NaCl, 0.01% Tween-20, 1 µM $ZnSO_4$). The respective enzymes were used at concentrations that resulted in quantitative proteolysis of 1 µM of substrate after 20 minutes at 37° C.

Test compounds were assayed over the range of concentrations from 10 µM to 20 pM. Test compounds were added to the enzymes and incubated for 30 minute at 37° C. prior to initiating the reaction by the addition of substrate. Reactions were terminated after 20 minutes of incubation at 37° C. by the addition of glacial acetic acid to a final concentration of 3.6% (v/v).

Plates were read on a fluorometer with excitation and emission wavelengths set to 320 nm and 405 nm, respectively. Inhibition constants were obtained by nonlinear regression of the data using the equation (GraphPad Software, Inc., San Diego, Calif.):

$$v = v_0/[1+(I/K')]$$

where v is the reaction rate, $v_0$ is the uninhibited reaction rate, I is the inhibitor concentration and K' is the apparent inhibition constant.

The compound of formula I' where $R^a$ and $R^b$ are H was tested in this assay and found to have a $pK_i$ value at human NEP of ≥9.0. The following compounds were found to have $pK_i$ values at human NEP as follows:

| Ex. | $pK_i$ |
| --- | --- |
| 1A | n.d. |
| 1B | n.d. |
| 1C | n.d. |
| 1D | ≥9.0 |
| 1E | ≥9.0 |
| 1F | ≥9.0 |
| 1G | n.d. |
| 1H | n.d. |
| 1I | 8.5-9.0 |
| 1J | 8.5-9.0 |
| 2A | 8.5-9.0 |
| 2B | ≥9.0 |
| 2C | ≥9.0 |
| 2D | ≥9.0 |
| 2E | 8.5-9.0 |
| 2F | ≥9.0 |
| 2G | ≥9.0 |
| 2H | 8.0-8.5 |
| 2I | n.d. |
| 2J | 8.5-9.0 |
| 2K | ≥9.0 |
| 2L | ≥9.0 |
| 2M | ≥9.0 |
| 2N | ≥9.0 |
| 2O | ≥9.0 |
| 2P | ≥9.0 |
| 2Q | 8.5-9.0 |
| 2R | ≥9.0 |
| 2S | 8.0-8.5 |

The remaining compounds were not tested (n.d.) since activity would not be expected in this in vitro assay; however, based upon the activity of the active forms, the corresponding prodrugs are expected to have in vivo NEP activity.

The compound of formula I' where $R^a$ is H and $R^b$ is F (Example 3A) and the compound of formula I' where $R^a$ is F and $R^b$ is H (Example 3B) were both tested in this assay and found to have a $pK_i$ value at human NEP of ≥9.0. Based upon the activity of these active forms, the corresponding prodrug compounds are expected to have in vivo NEP activity.

The compound of formula II where $R^a$ is F, $R^b$ is H, $R^2$ is H, and $R^7$ is H (Example 4A) was tested in this assay and found to have a $pK_i$ value at human NEP of ≥9.0. Based upon the activity of this active form, the corresponding prodrug compounds are expected to have in vivo NEP activity. The following compounds were also found to have $pK_i$ values at human NEP:

| Ex. | $pK_i$ |
| --- | --- |
| 4B | ≥9.0 |
| 4C | ≥9.0 |

The compound of formula IIIa, where $R^a$ is F, $R^b$ is H, $R^2$ is H, and $R^7$ is H (Example 5A), and the compounds of formula IIIb, where $R^a$ is F, $R^b$ is H, $R^2$ is H, and $R^7$ is H (Example 5B) were both tested in this assay and found to have a $pK_i$ value at human NEP of ≥9.0. Based upon the activity of these active forms, the corresponding prodrug compounds are expected to have in vivo NEP activity. In addition, the following compounds were also found to have $pK_i$ values at human NEP:

| Ex. | $pK_i$ |
| --- | --- |
| 5C | ≥9.0 |
| 5D | ≥9.0 |

The compound of formula V, where $R^a$ is H, $R^b$ is Cl, $R^2$ is H, $R^3$ is —$OCH_3$, and $R^7$ is H (Example 6A) and the compound of formula V' (where $R^a$ and $R^b$ are H and $R^3$ is —OH; Example 6D) were both tested in this assay and found to have a $pK_i$ value at human NEP of ≥9.0. Based upon the activity of these active forms, the corresponding prodrug compounds are expected to have in vivo NEP activity. In addition, the following compounds were also found to have $pK_i$ values at human NEP:

| Ex. | $pK_i$ |
| --- | --- |
| 6B | 7.0-8.0 |
| 6C | n.d. |
| 6E | n.d. |
| 6F | n.d. |
| 6G | ≥9.0 |
| 6H | ≥9.0 |
| 6I | ≥9.0 |
| 6J | ≥9.0 |
| 6K | 8.5-9.0 |
| 6L | ≥9.0 |
| 6M | ≥9.0 |
| 6N | ≥9.0 |
| 6O | ≥9.0 |

The remaining compounds were either not tested or did not show activity in this in vitro assay (n.d.) since activity would not be expected; however, based upon the activity of the active forms, these corresponding prodrugs are expected to have in vivo NEP activity.

Compounds of formula VI were tested in this assay and found to have $pK_i$ values at human NEP as follows:

| Ex. | $pK_i$ |
|---|---|
| 7A | ≥9.0 |
| 7B | ≥9.0 |
| 7C | ≥9.0 |
| 7D | 8.5-9.0 |
| 7E | ≥9.0 |
| 7F | ≥9.0 |

Based upon the activity of these active forms, the corresponding prodrug compounds are expected to have in vivo NEP activity.

Compounds of formula VII were tested in this assay and found to have $pK_i$ values at human NEP as follows:

| Ex. | $pK_i$ |
|---|---|
| 8A | ≥9.0 |
| 8B | 8.5-9.0 |
| 8C | ≥9.0 |

Based upon the activity of this active form, the corresponding prodrug compounds are expected to have in vivo NEP activity.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety to the same extent as if each document had been individually incorporated by reference herein.

What is claimed is:

1. A compound of formula V:

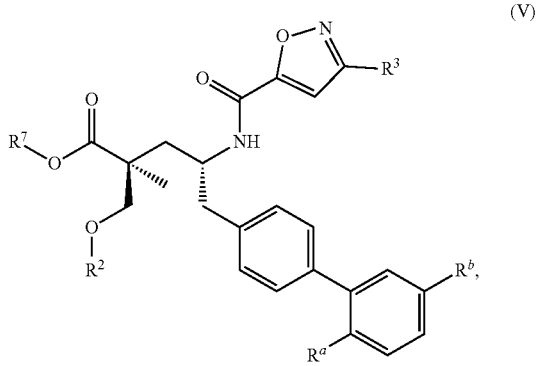

(V)

or a salt or stereoisomer thereof, wherein:
$R^a$ is selected from Cl and F and $R^b$ is H; or $R^a$ is H and $R^b$ is selected from Cl and F; or $R^a$ is F and $R^b$ is Cl;
$R^2$ is selected from H, —$C_{1-6}$alkyl, —$(CH_2)_{2-3}OR^e$, and —$(CH_2)_{2-3}NR^eR^e$;
$R^3$ is selected from —OH, —$OCH_3$, —$OCH_2CH_3$, and —$C_{1-4}$alkyl;
$R^7$ is selected from H, —$C_{1-6}$alkyl, —$[(CH_2)_2O]_{1-3}CH_3$, —$CHR^cOC(O)$—$C_{1-4}$alkyl, —$CH_2OC(O)CHR^d$—$NH_2$, —$CH_2OC(O)CHR^d$—$NHC(O)O$—$C_{1-6}$alkyl, —$CHR^cOC(O)O$—$C_{2-4}$alkyl, —$CHR^cOC(O)O$-cyclohexyl, —$CH_2CH(NH_2)C(O)OCH_3$, —$C_{2-4}$alkylene-N$(CH_3)_2$, —$C_{0-6}$alkylenemorpholinyl, and

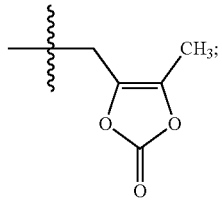 [SMILES: *Cc1oc(=O)oc1C]

$R^c$ is selected from H and —$C_{1-3}$alkyl;
$R^d$ is selected from H, —$CH_3$, —$CH(CH_3)_2$, phenyl, and benzyl; and
each $R^e$ is independently selected from H and —$CH_3$.

2. The compound, salt or stereoisomer of claim 1, wherein $R^2$ is —$C_{1-6}$alkyl.

3. The compound, salt or stereoisomer of claim 1, wherein $R^2$ is selected from —$CH_3$ and —$CH_2CH_3$.

4. The compound, salt or stereoisomer of claim 1, wherein $R^2$ is —$CH_2CH_3$.

5. The compound, salt or stereoisomer of claim 1, wherein $R^3$ is —OH.

6. The compound, salt or stereoisomer of claim 4, wherein $R^3$ is —OH.

7. The compound, salt or stereoisomer of claim 1, wherein $R^7$ is H or —$C_{1-6}$alkyl.

8. The compound, salt or stereoisomer of claim 1, wherein $R^7$ is H.

9. The compound, salt or stereoisomer of claim 4, wherein $R^7$ is H.

10. The compound, salt or stereoisomer of claim 6, wherein $R^7$ is H.

11. The compound, salt or stereoisomer of claim 4, wherein $R^a$ is F and $R^b$ is Cl.

12. The compound, salt or stereoisomer of claim 6, wherein $R^a$ is F and $R^b$ is Cl.

13. The compound, salt or stereoisomer of claim 9, wherein $R^a$ is F and $R^b$ is Cl.

14. A pharmaceutical composition comprising the compound, salt or stereoisomer of claim 1 and a pharmaceutically acceptable carrier.

15. A pharmaceutical composition comprising the compound, salt or stereoisomer of claim 10 and a pharmaceutically acceptable carrier.

16. A pharmaceutical composition comprising the compound, salt or stereoisomer of claim 13 and a pharmaceutically acceptable carrier.

17. The pharmaceutical composition of claim 15, wherein the pharmaceutically acceptable carrier is magnesium stearate.

18. The pharmaceutical composition of claim 16, wherein the pharmaceutically acceptable carrier is magnesium stearate.

19. An oral dosage form comprising the compound, salt or stereoisomer of claim 10.

20. An oral dosage form comprising the compound, salt or stereoisomer of claim 13.

* * * * *